(12) United States Patent
Robertson et al.

(10) Patent No.: US 10,883,145 B2
(45) Date of Patent: Jan. 5, 2021

(54) COMPOSITIONS AND METHODS FOR METAGENOME BIOMARKER DETECTION

(71) Applicant: THE TRUSTEES OF THE UNIVERSITY OF PENNSYLVANIA, Philadelphia, PA (US)

(72) Inventors: Erle S. Robertson, Wynnewood, PA (US); James Alwine, Media, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/301,539

(22) PCT Filed: Apr. 10, 2015

(86) PCT No.: PCT/US2015/025415
§ 371 (c)(1),
(2) Date: Oct. 3, 2016

(87) PCT Pub. No.: WO2015/157696
PCT Pub. Date: Oct. 15, 2015

(65) Prior Publication Data
US 2017/0022573 A1    Jan. 26, 2017

Related U.S. Application Data

(60) Provisional application No. 61/978,333, filed on Apr. 11, 2014.

(51) Int. Cl.
| | | |
|---|---|---|
| *C12Q 1/68* | (2018.01) | |
| *C12Q 1/6888* | (2018.01) | |
| *G16B 25/00* | (2019.01) | |
| *G16B 20/00* | (2019.01) | |

(52) U.S. Cl.
CPC ........... *C12Q 1/6888* (2013.01); *G16B 20/00* (2019.02); *G16B 25/00* (2019.02); *C12Q 2600/158* (2013.01)

(58) Field of Classification Search
None
See application file for complete search history.

(56) References Cited

U.S. PATENT DOCUMENTS

| | | | | |
|---|---|---|---|---|
| 6,387,652 B1 * | 5/2002 | Haugland | ............... | C12Q 1/689 435/254.1 |
| 7,052,836 B2 * | 5/2006 | Morrison | ............. | C12Q 1/6895 435/6.13 |
| 2002/0064792 A1 * | 5/2002 | Lincoln | .................. | G16B 50/00 435/6.11 |
| 2005/0037393 A1 | 2/2005 | Gunderson et al. | | |
| 2006/0194223 A1 * | 8/2006 | Andreoli | ............. | C12Q 1/6813 435/6.11 |
| 2006/0216723 A1 | 9/2006 | Diaz et al. | | |
| 2010/0120098 A1 | 5/2010 | Grunenwald et al. | | |
| 2012/0065088 A1 | 3/2012 | Danielsen et al. | | |
| 2012/0165215 A1 * | 6/2012 | Andersen | ............. | C12Q 1/6837 506/9 |
| 2013/0196323 A1 * | 8/2013 | Hall | ........................ | C12Q 1/689 435/6.11 |
| 2013/0261196 A1 | 10/2013 | Diamond et al. | | |

FOREIGN PATENT DOCUMENTS

| | | | | |
|---|---|---|---|---|
| WO | WO2009069843 | * | 6/2009 | |
| WO | WO-2013086201 A1 * | 6/2013 | | ............. C12Q 1/689 |
| WO | 2013173774 A2 | 11/2013 | | |

OTHER PUBLICATIONS

Sebat et al.( Applied and environmental microbiology 69.8 (2003): 4927-4934).*
Lee et al. (The ISME Journal (2013) 7, 1974-1984).*
Evans et al. (p. 126-127, Catalogue of Research Projects in the Fifth Frame Programme, European Commission, 2003).*
International Search Report and Written Opinion dated Jul. 22, 2015—PCT/US2015/025415.
The Human Microbiome Project Consortium, Nature, 2012; 486(7402)207-214.
Baldwin, et al., "Metagenomic assay for identification of microbial pathogens in tumor tissues", Mbio 2014: 5: e01714-14.
Brodie, "Application of a High-Density Oligonucleotide Microarray Approach To Study Bacterial Population Dynamics during Uranium Reduction and Reoxidation", Appl Environ Microbial 2006; 72(9):6288-6298.
Chen, et al., "Using a Pan-Viral Microarray Assay (Virochip) to Screen Clinical Samples for Viral Pathogens", J Vis Exp 2011 (50), e2536-e2536.
Cox, et al., "Sequencing the human microbiome in health and disease", Hum Mol Genet 2013; 22(R1):R88-94.
De Martel, et al., "Global burden of cancers attributable to infections in 2008: a review and synthetic analysis", Lancet Oncol 2012; 13(6):607-615.
Gjymishka, et al., "Influence of host immunoregulatory genes, ER stress and gut microbiota on the shared pathogenesis of inflammatory bowel disease and Type 1 diabetes", Immunotherapy 2013; 5(12):1357-1366.
Iida, et al., "Commensal Bacteria Control Cancer Response to Therapy by Modulating the Tumor Microenvironment", Science 2013; 342(6161):967-970.
Kamada, et al., "Control of pathogens and pathobionts by the gut microbiota", Nat Immunol. Jul. 2013 ; 14(7): 685-690.
Koboziev, et al., "Role of the Enteric Microbiota in Intestinal Homeostasis and Inflammation", Free Radic Biol Med. Mar. 2014; 0: 122-133.

(Continued)

*Primary Examiner* — Tracy Vivlemore
*Assistant Examiner* — Sahana S Kaup
(74) *Attorney, Agent, or Firm* — Saul Ewing Arnstein & Lehr, LLP; Kathryn Doyle; Justin Crotty

(57) ABSTRACT

The present invention provides compositions and methods for the multiplex detection of biomarkers in an environmental, non-biological or biological sample. Compositions and methods are provided for simultaneously detecting and identifying multiple pathogens, including viruses, bacteria, fungi, protozoa and helminths, present in a sample.

6 Claims, 44 Drawing Sheets

(56) References Cited

OTHER PUBLICATIONS

Laass, et al., "Diagnosis and classification of Crohn's disease", 2014, Autoimmun Rev 13(4-5):467-471 (abstract).
Major, et al., "Irritable bowel syndrome, inflammatory bowel disease and the microbiome", CurrOpin Endocrinol Diabetes Obes 2014; 21(1):15-21.
Martinez, et al., "Significance of the Microbiome in Chronic Obstructive Pulmonary Disease", Ann Am Thorac Soc 2013; 10 Suppl: S170-179.
Norman, et al., "Kingdom-agnostic Metagenomics and the Importance of Complete Characterization of Enteric Microbial Communitie", Gastroenterology. May 2014 ; 146(6): 1459-1469.
Ooi, et al., "Dominant Effects of the Diet on the Microbiome and the Local and Systemic Immune Response in Mice", PLoS One, Jan. 2014, 9:(1):e86366.
Scallan, et al., "Foodborne illness acquired in the United States—major pathogens", Emerg Infect Dis. 2011; 17(1): 7-15.
Scharschmidt, et al., "What Lives on Our Skin: Ecology, Genomics and Therapeutic Opportunities Of the Skin Microbiome", Drug Discov Today Dis Mech 2013; 10(3-4).
Schwarzberg, et al., "The Personal Human Oral Microbiome Obscures the Effects of Treatment on Periodontal Disease", PLoS One 2014; 9(1):e86708, Jan. 2014.
Segal, et al., "Lung Microbiome for Clinicians: New Discoveries about Bugs in Healthy and Diseased Lungs", Ann Am Thorac Sac 2014; 11(1):108-116.
Sze, et al., "The Host Response To The Bacterial Lung Tissue Microbiome In Chronic Obstructive Pulmonary Disease", Ann Am Thorac Soc 2014; 11 Suppl 1:577 (Abstract).
Tu, et al., "GeoChip 4: a functional gene-array-based high-throughput environmental technology for microbial community analysis", Mol Ecol Resour 2014; doi: 10.1111/1755-0998.12239.
Wong, et al., "Optimization and clinical validation of a pathogen detection microarray", Genome Biol 2007; 8 (5):R93.
Xuan, et al., "Microbial dysbiosis is associated with human breast cancer", PLoS One, Jan. 2014; 9(1):e83744.
Extended European Search Report for European Patent Application No. 15776225.3 dated Jan. 23, 2018.
Lee, et al.,"The PathoChip, a functional gene array for assessing pathogenic properties of diverse microbial communities," ISME J. 7(10) ,2013 ,1974-1984.
Li, et al.,"Selection of optimal oligonucleotide probes for microarrays using multiple criteria, global alignment and parameter estimation," Nucleic Acids Res. 33(19) ,2005 ,6114-6123.

* cited by examiner

Current Testing Options

Sample

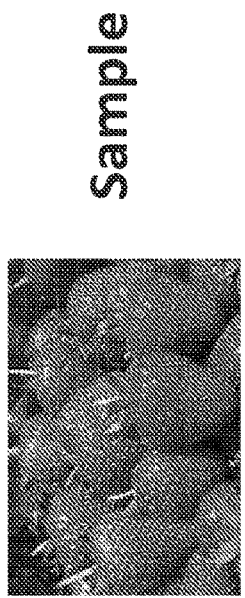

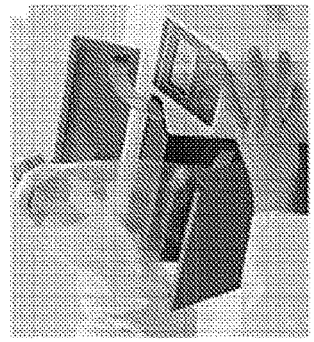

Ab-bead capture, PCR
(Life Tech Pathatrix, MicroSEQ)
DNA-bead capture
(Roka Atlas)
Immunoassay (3M Tecra)
DNA probe amplification
(Neogen ANSR)

Enrichment culture
6-12 hrs, non-selective medium or
12-24 hrs, selective medium

Culture isolate
12-24 hrs, selective medium

Colony counting
PCR (VNTR, etc.)
Restriction digest map

Detect and quantify
Only one targeted organism per test,
poor to no coverage of viruses

Figure 1A

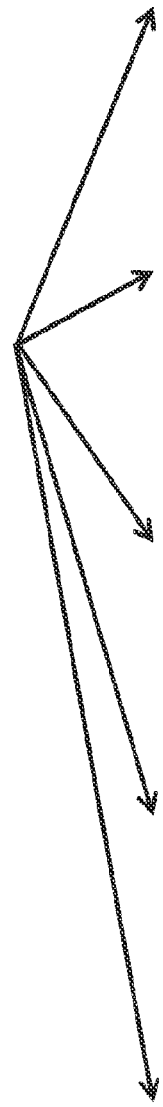

| Name: | MicroSEQ | Tecra VIA | Atlas | ANSR | NeoSEEK lab service |
|---|---|---|---|---|---|
| Vendor: | Life Technologies | 3M | Roka Bioscience | Neogen | Neogen |
| Targets per test: | 1 | 1 | 1 | 1 | same as ANSR |
| Targets available: | 8 | 9 | 2 | 2 (+1 in dev) | |
| Input culture vol: | 1 ml | | 400 ul (food), 12 ul (swabs) | 50 ul | |
| Step 2: | DNA purification (2 hrs) | Antigen capture | Sample lysis | Sample lysis (10 min) | |
| Step 3: | TaqMan PCR (40 min - 2 hrs) | Enzyme-antibody binding | Magnetic bead DNA capture | Probe primed isothermal amplification (20 min) | |
| Step 4: | Data analysis | Colorimetric detection | Transcription amplification | DNA beacon fluorescence detection (10-18 min) | |
| Step 5: | | Data analysis | Hybridization protection assay | Data analysis | |
| Step 6: | | | Data analysis (total time 3 hrs after sample prep, 300 samples/day) | | |
| List price per test: | $14.45 | $8.33 | $9 to $16 | $9.38 or $10.41 | $35 |
| Equipment: | Real-time thermocycler | Plate reader | Atlas robot ($175,000) | ANSR Reader ($10,500) | Collection kit ($25/sample) |

Figure 1B

Figure 4. PathoChip v3 includes foodborne pathogens
76 organisms, multiple sequences targeted Astrovirus MLB1
Astrovirus VA1
Astrovirus: HMO Astrovirus A
Astrovirus: Human astrovirus
Astrovirus: Mink astrovirus (Mamastrovirus 10)
Astrovirus: Mouse astrovirus M-52/USA/2008
Astrovirus: Ovine astrovirus (Mamastrovirus 13)
Bacillus anthracis str. 'Ames Ancestor'
Bacillus mycoides gene for 16S rRNA, strain: BGSC1-DN3
Brucella canis ATCC 23365
Brucella cetaceae partial 16S rRNA gene, strain NCTC 12891
Brucella melitensis 16M
Brucella melitensis biovar Abortus 2308
Brucella neotomae 16S ribosomal RNA gene
Brucella ovis ATCC 25840
Brucella pinnipediae partial 16S rRNA gene, strain NCTC 12890
Brucella suis ATCC 23445
Campylobacter fetus subsp. fetus 82-40
Campylobacter jejuni subsp. jejuni NCTC 11168
Clostridium botulinum B str. Eklund 17B
Clostridium perfringens SM101
Clostridium septicum 16S ribosomal RNA gene
Clostridium tetani E88
Cryptosporidium hominis 18S ribosomal RNA gene
Cryptosporidium parvum strain Koala K1 18S ribosomal RNA gene
Cryptosporidium parvum strain SPYZ 18S ribosomal RNA gene Cyclospora cayetanensis strain CY19 clone 6 small subunit rRNA
Escherichia coli O157:H7 str. TW14359
Escherichia coli SMS-3-5
Escherichia coli str. K-12 substr. W3110
Giardia lamblia ATCC 50803 Cytochrome B5 mRNA
Hepatitis A virus
Listeria monocytogenes str. 4b F2365
Murine norovirus 1
Mycobacterium bovis BCG str. Pasteur 1173P2
Norwalk virus
Rotavirus A
Rotavirus C
Rotavirus: Adult diarrheal rotavirus strain J19
Salmonella choleraesuis strain DSM 14846 16S ribosomal RNA gene
Salmonella enterica subsp. enterica serovar Paratyphi A str. ATCC 9150
Salmonella enterica subsp. enterica serovar Paratyphi B str. SPB7
Salmonella enteritidis SE22 16S ribosomal RNA gene
Salmonella typhi 16S ribosomal RNA gene
Salmonella typhimurium LT2
Sapovirus C12 strain C12
Sapovirus Hu/Dresden/pJG-Sap01/DE
Sapovirus Mc10
Shigella boydii CDC 3083-94
Shigella dysenteriae Sd197
Shigella flexneri 5 str. 8401
Shigella sonnei Ss046

Staphylococcus aureus subsp. aureus USA300_TCH1516
Streptococcus pyogenes NZ131
Toxoplasma gondii 18S ribosomal RNA
Toxoplasma gondii 18S ribosomal RNA gene
Toxoplasma gondii cytochrome b mRNA
Trichinella britovi 18S ribosomal RNA gene
Trichinella murrelli 18S ribosomal RNA gene
Trichinella nativa 18S ribosomal RNA gene
Trichinella nelsoni 18S ribosomal RNA gene
Trichinella papuae 18S ribosomal RNA gene
Trichinella pseudospiralis 18S ribosomal RNA gene
Trichinella sp. T6 18S ribosomal RNA gene
Trichinella sp. T8 18S ribosomal RNA gene
Trichinella spiralis 18S ribosomal RNA gene
Trichinella spiralis 5.8S ribosomal RNA gene
Trichinella spiralis mitochondrion
Trichinella spiralis strain ISS10 18S ribosomal RNA gene
Trichinella zimbabwensis 18S ribosomal RNA gene
Vibrio cholerae O395
Vibrio parahaemolyticus strain CT11 16S ribosomal RNA gene
Vibrio vulnificus strain L1 16S ribosomal RNA gene
Yersinia enterocolitica subsp. enterocolitica 8081
Yersinia pestis Pestoides F
Yersinia pseudotuberculosis PB1/+ figure 4

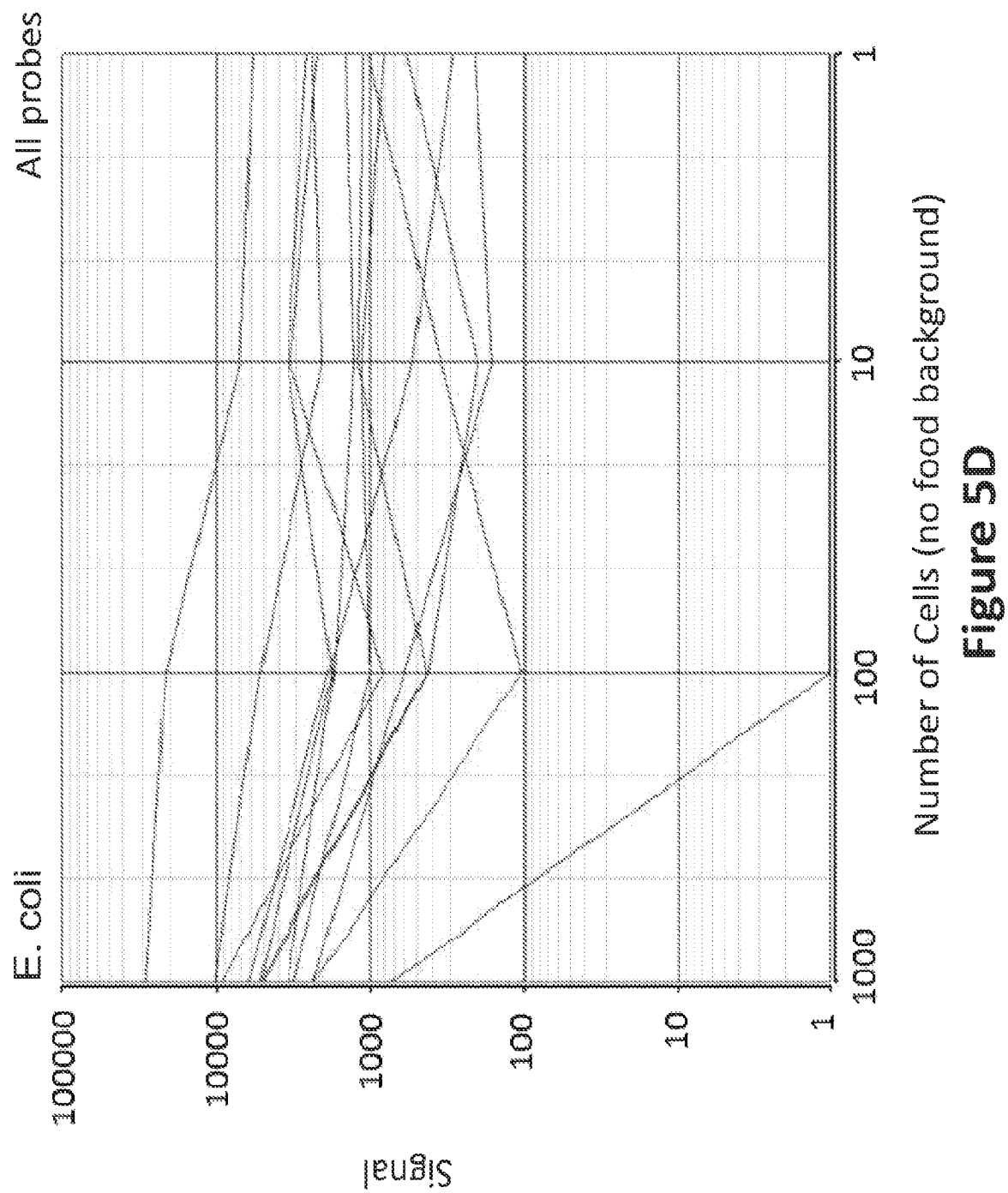

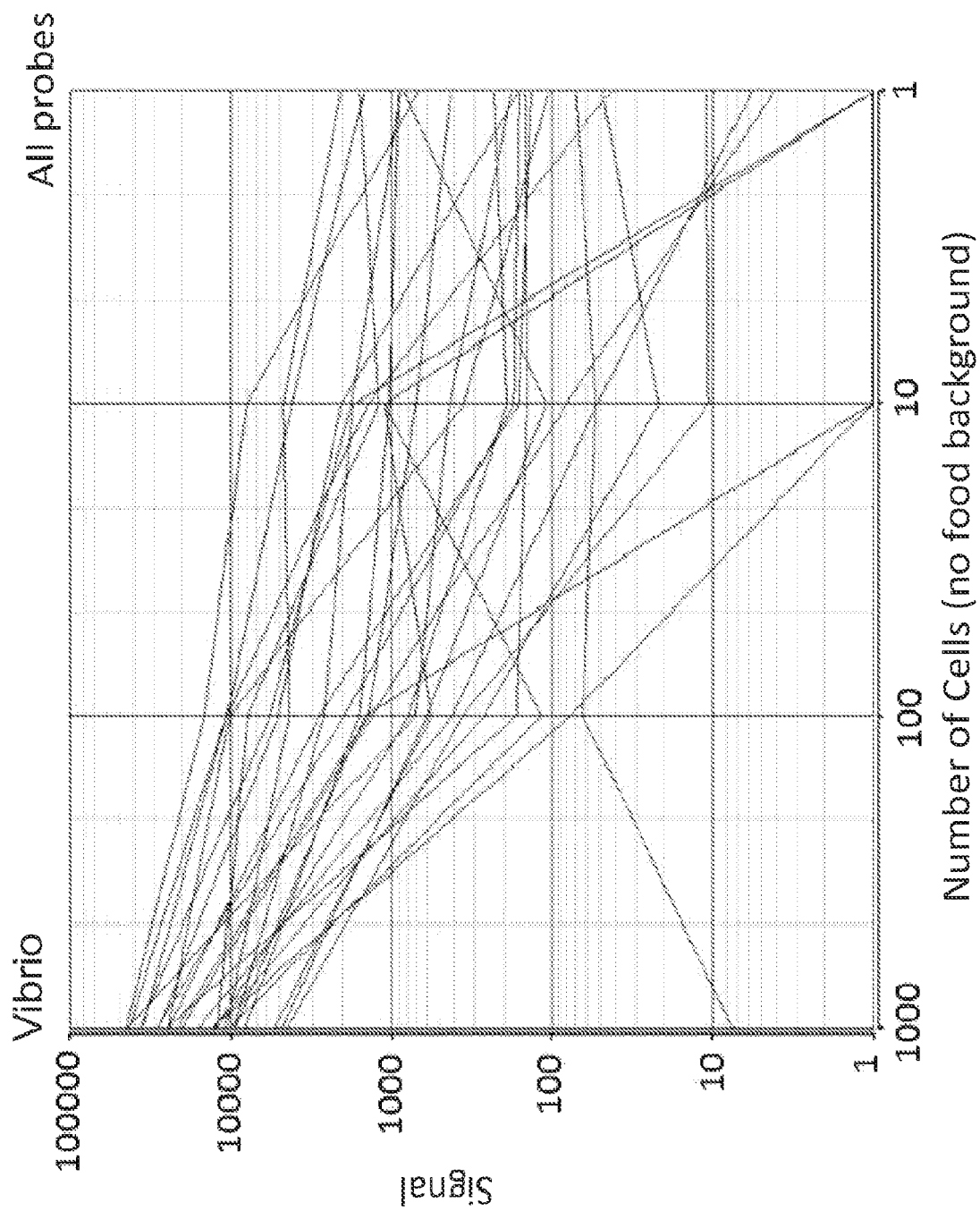

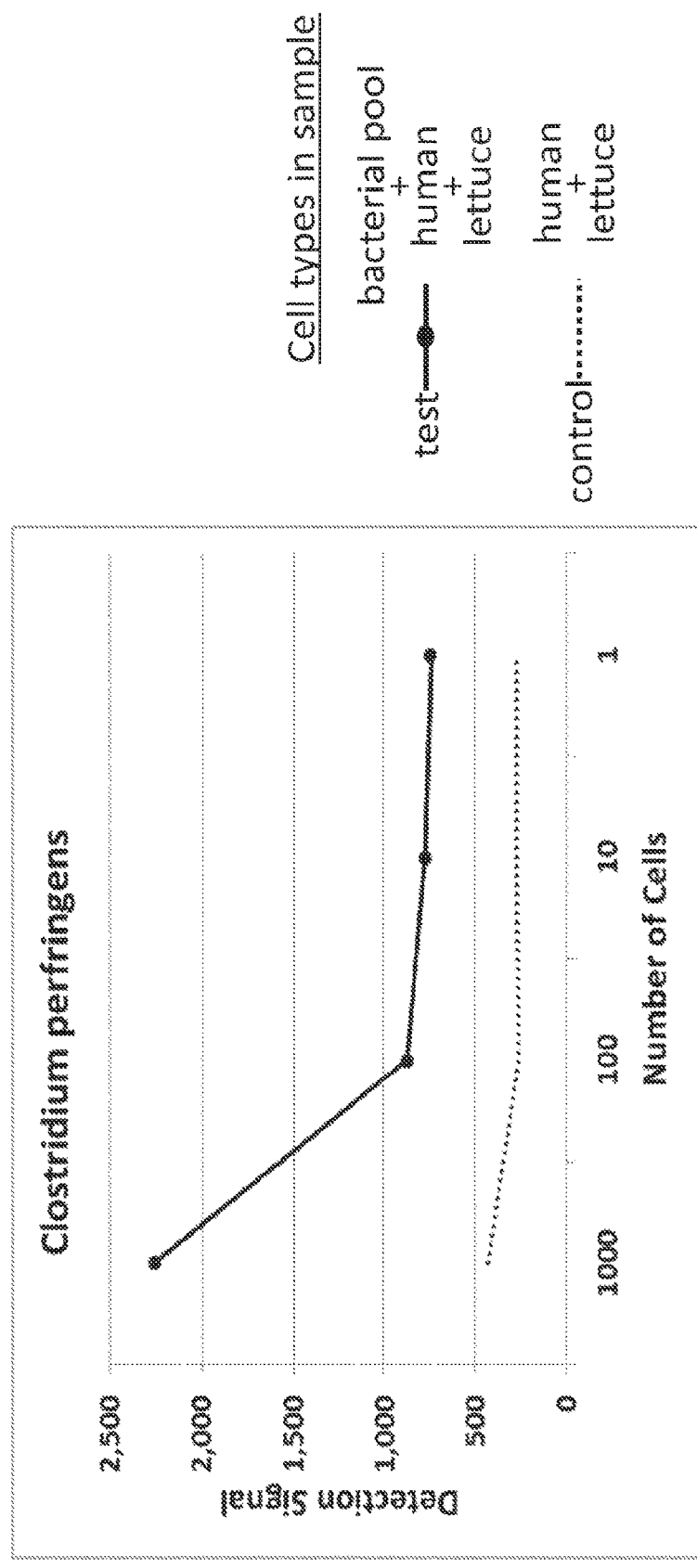

Figure 7

A small number of pathogen cells in a background of a large number of host cells can still be detected, but with less absolute signal compared to pure pathogen cultures (see phase 1). The difference between test signal and host-only control signal indicates detection ability. Ability to quantify the amount of pathogen requires more cells than ability to just call presence or absence.

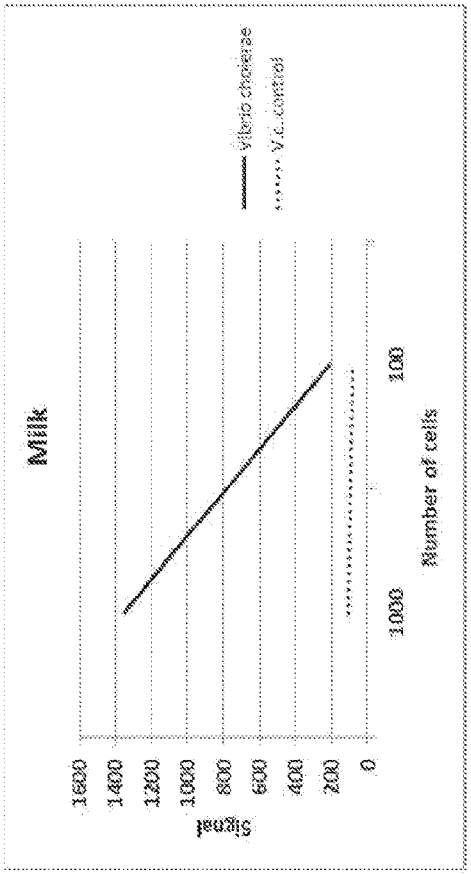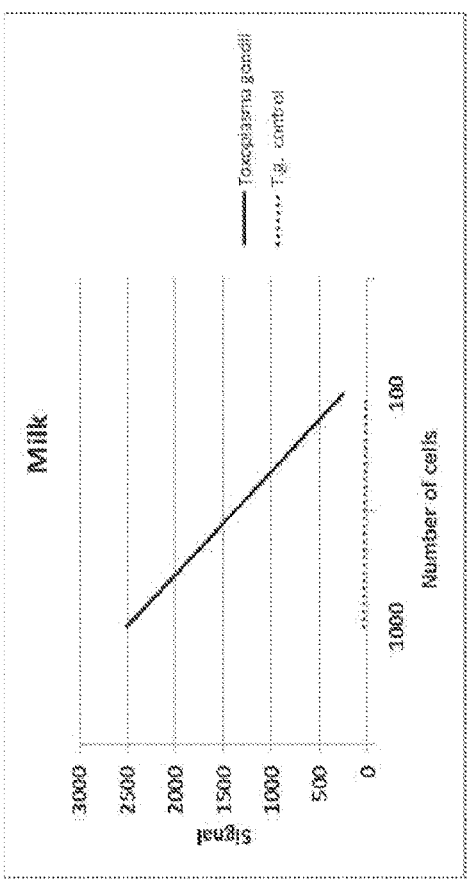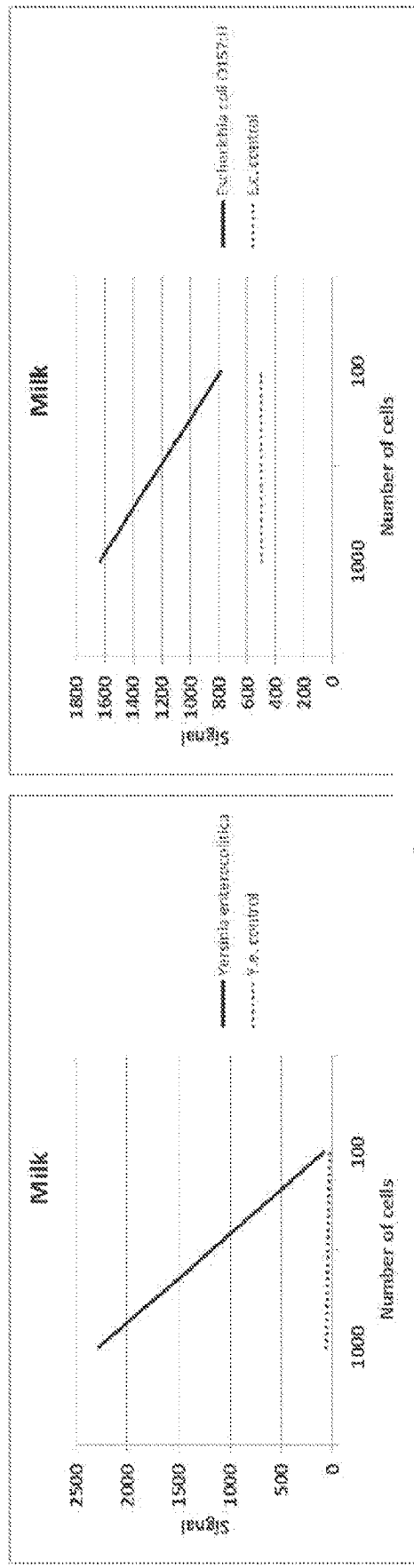
Figure 8

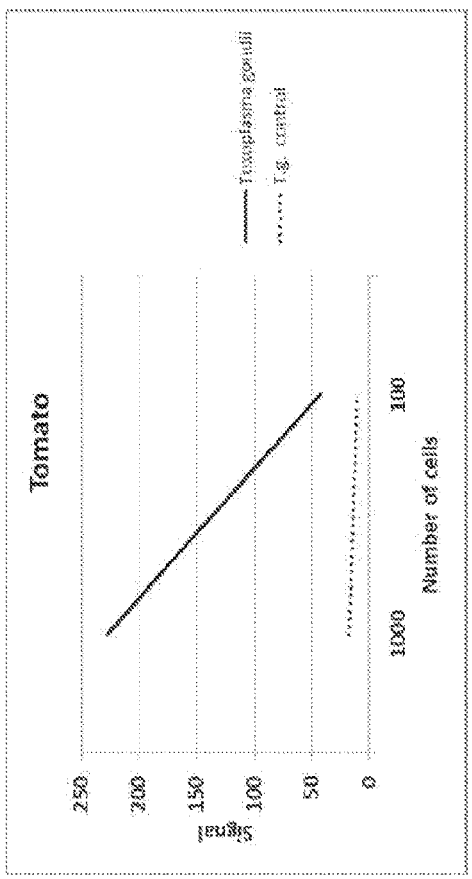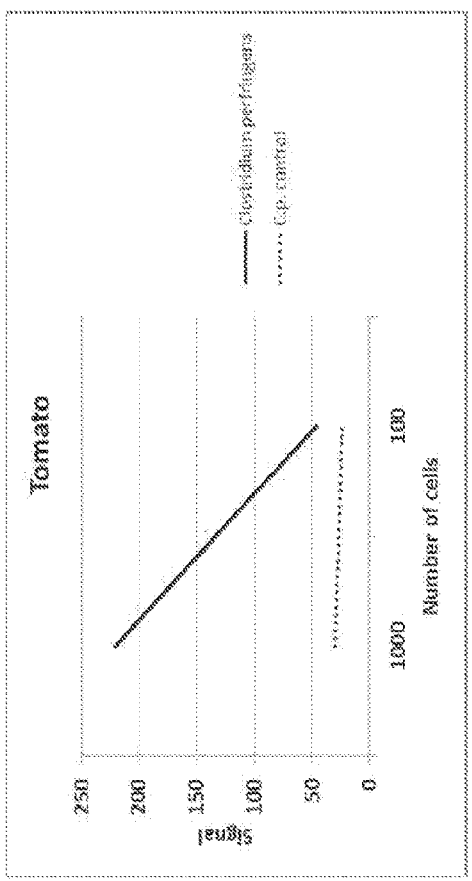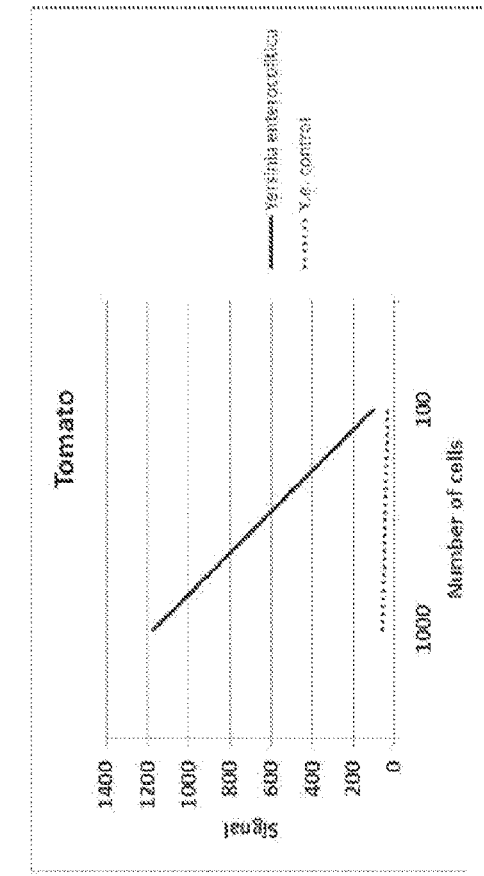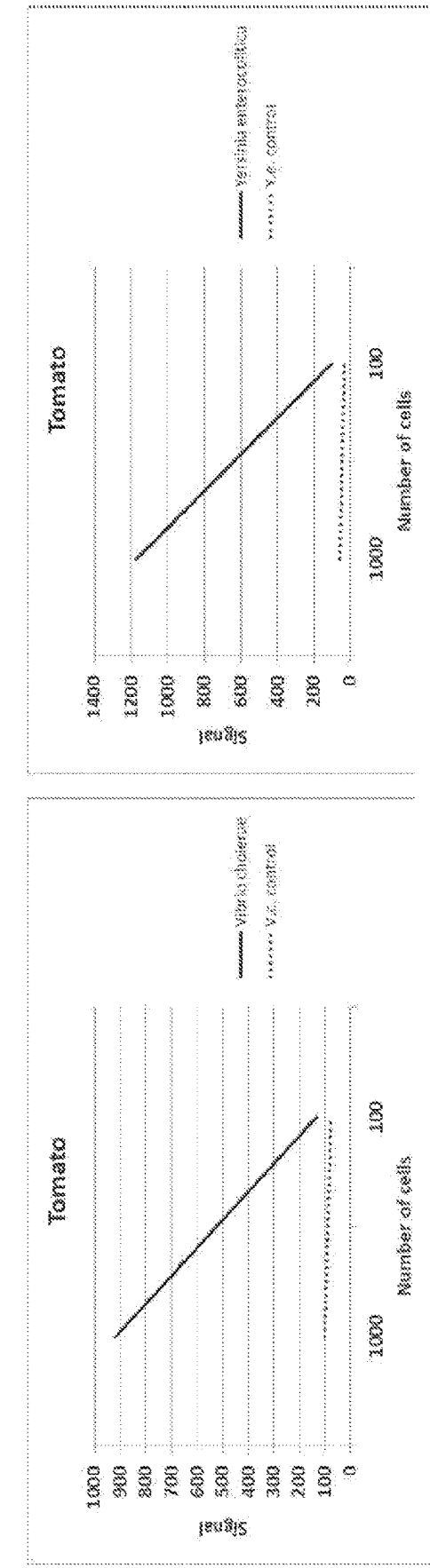
Figure 9

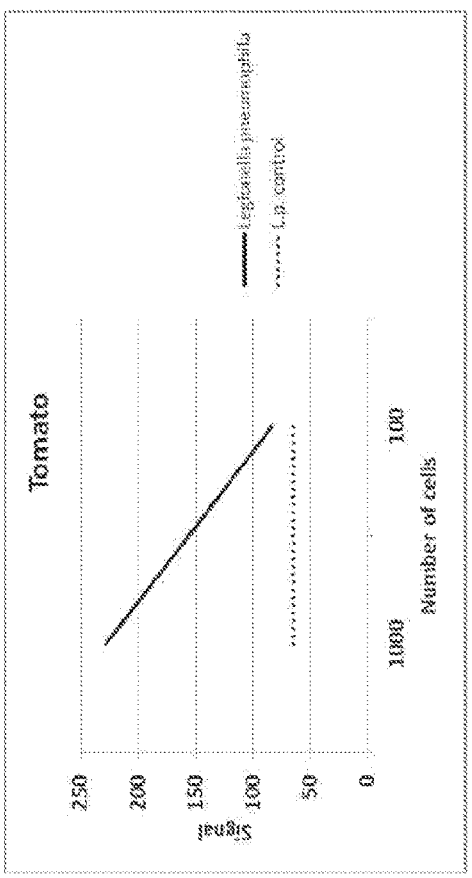
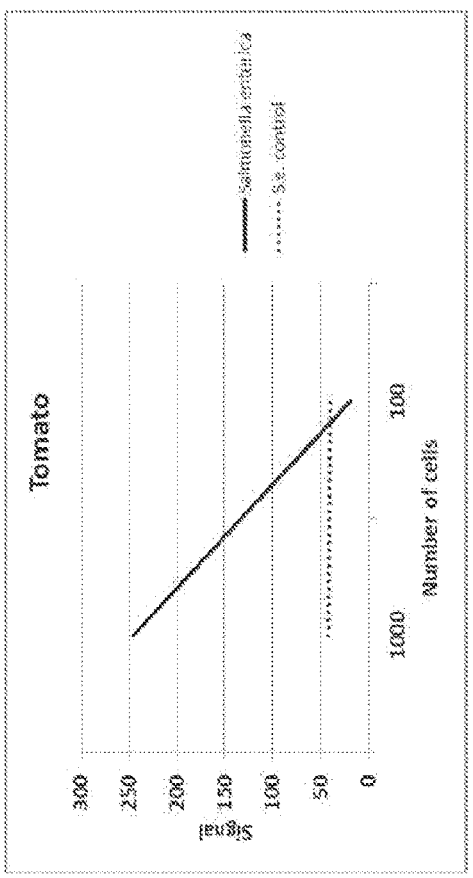
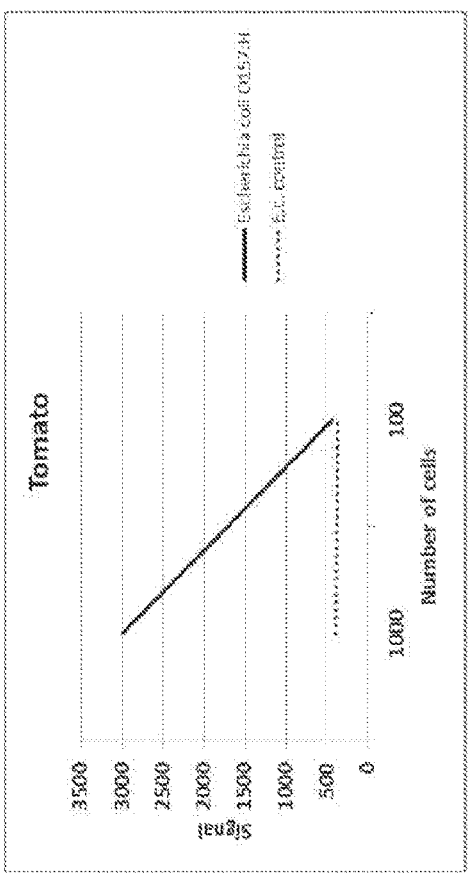
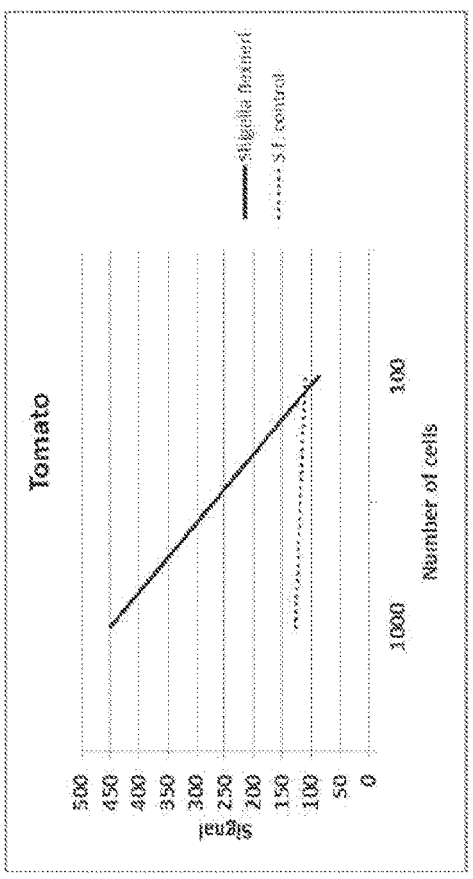
Figure 9

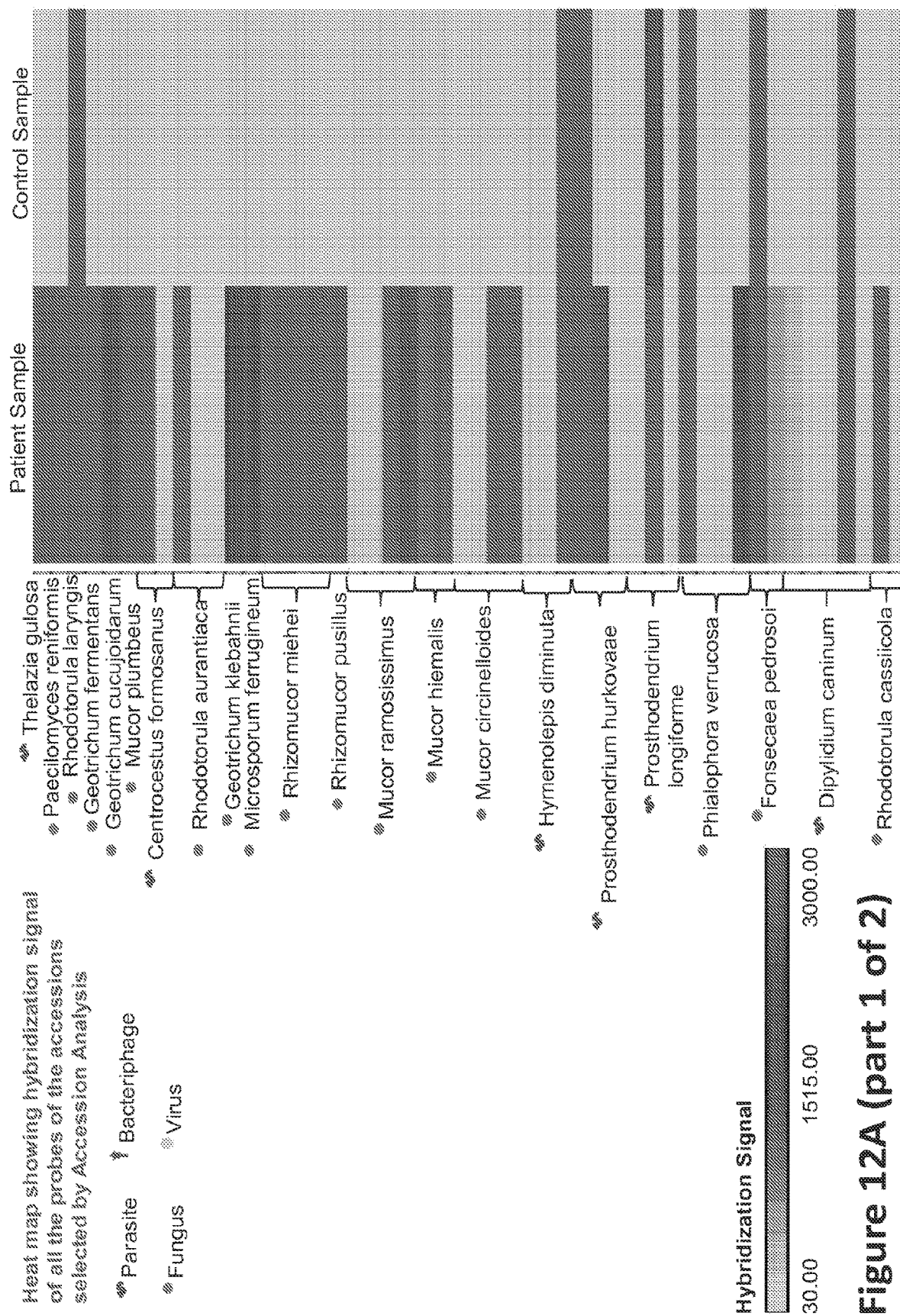
Figure 12A (part 1 of 2)

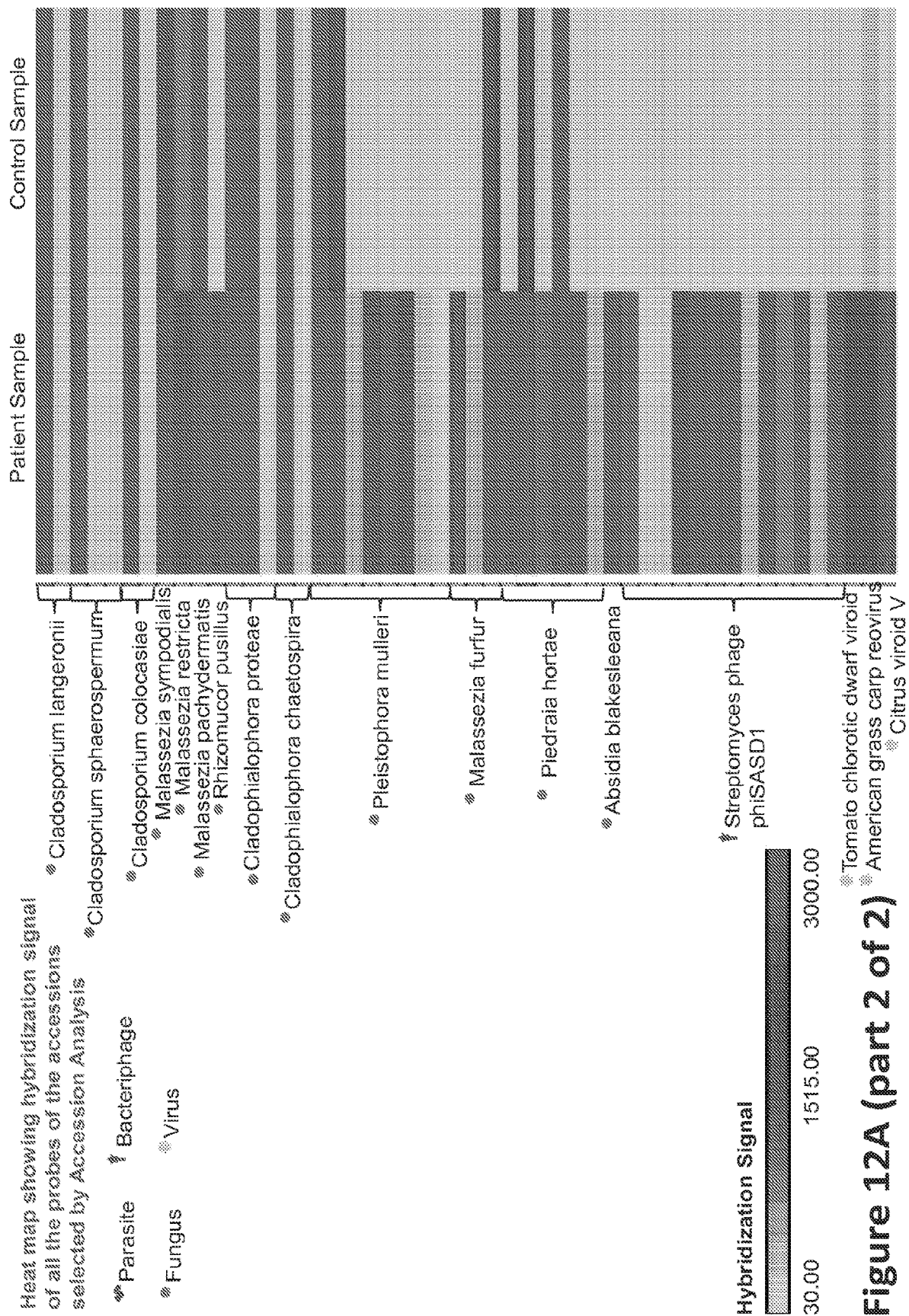
Figure 12A (part 2 of 2)

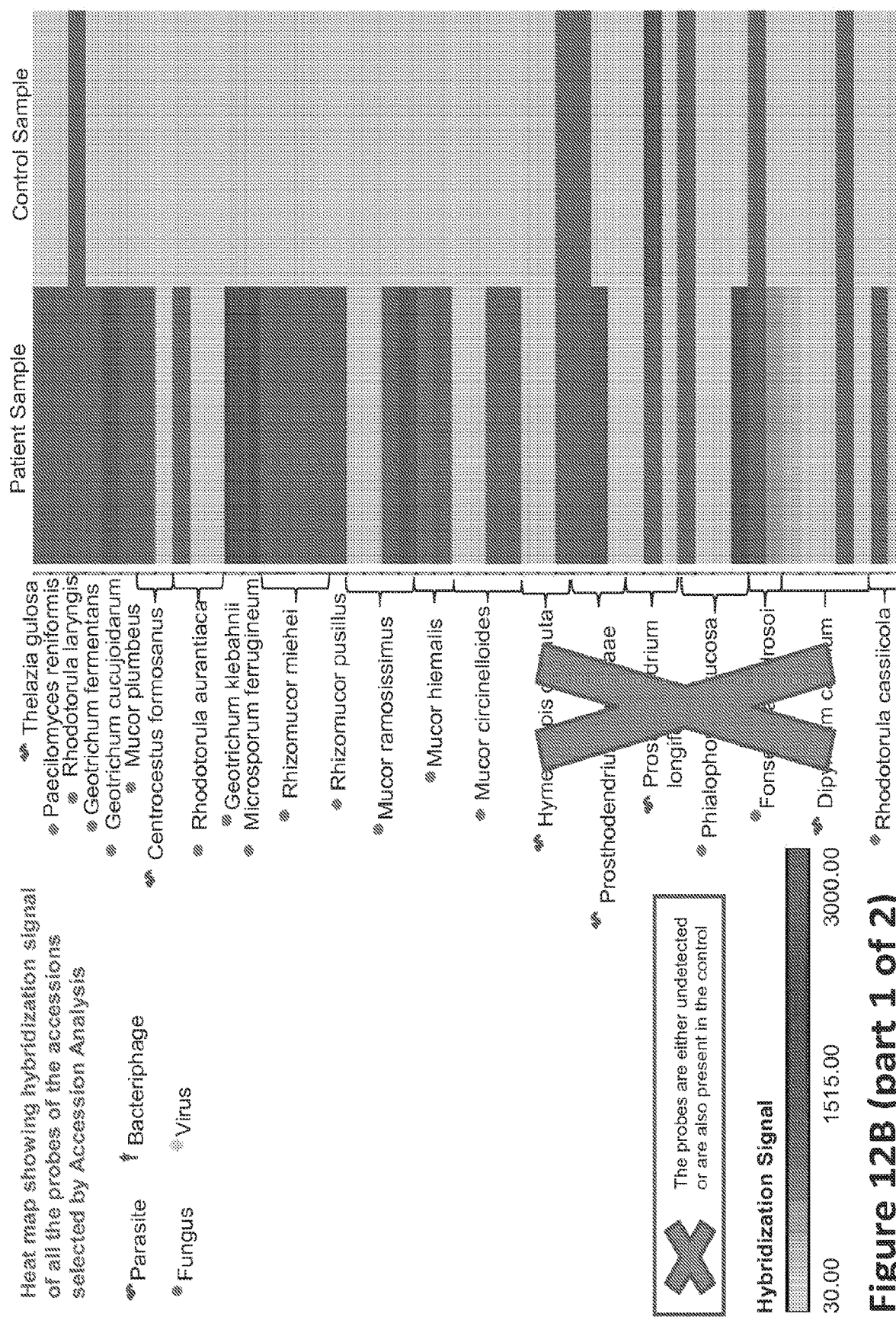
Figure 12B (part 1 of 2)

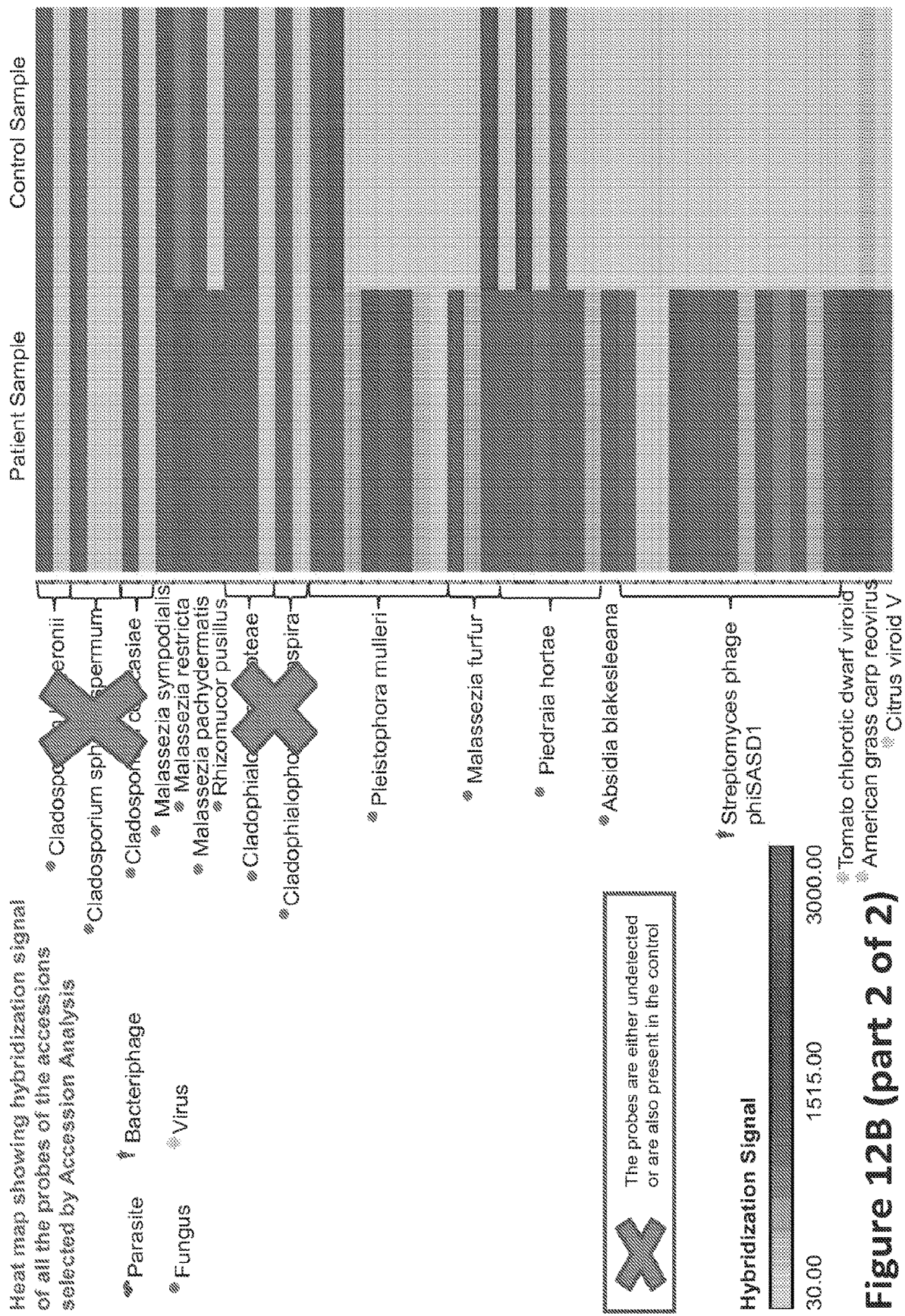
Figure 12B (part 2 of 2)

COMPOSITIONS AND METHODS FOR METAGENOME BIOMARKER DETECTION

CROSS-REFERENCE TO RELATED APPLICATIONS

This application is a 35 U.S.C. § 371 national phase application from, and claims priority to, International Application No. PCT/US2015/025415, filed Apr. 10, 2015, and published under PCT Article 21(2) in English, which claims priority to and the benefit of U.S. Provisional Application No. 61/978,333, filed Apr. 11, 2014, all of which applications are incorporated herein by reference in their entireties.

BACKGROUND OF THE INVENTION

The need to identify pathogenic organisms, including viruses, bacteria, fungi, helminths, and protozoa, has grown more acute in recent years. The complexity associated with the identification of pathogens linked to disease is daunting and the ability to detect these agents is of utmost importance to medical, veterinary and agricultural science. An important factor in the clinical management of infectious diseases lies in the establishment of the identity of the etiologic agent or pathogen responsible for the infection. In most instances, the identification of the infecting microbe is central to making decisions for appropriate therapy and care. In this regard, the attending physician necessarily relies upon the clinical microbiology laboratory to provide the essential information required to initiate a rational regimen of treatment. Challenges relating to current procedures for detecting pathogens in a clinical setting include the need to perform assays directly from clinical specimens or samples, the time required for detection, a possible inability to cultivate the infectious agent, difficulties regarding the detection of rare or unknown infectious agents, and difficulties associated with identifying an infectious agent among others that present similar symptoms.

In another example, there remain considerable challenges in food safety due to continual pathogen exposures in the food chain (Scallan et. al., "Foodborne illness acquired in the United States—major pathogens." Emerg Infect Dis. 2011; 17(1): 7-15). There are 48 million cases of foodborne illness reported each year in the US, resulting in approximately 128,000 hospitalizations and 3,000 deaths. The economic and healthcare impact is significant, estimated at $152 billion. Food safety testing has become important for identifying and removing sources of food that have been contaminated by pathogen exposure. The market for food safety testing was $3.3 billion in 2011 and is projected to continue experiencing compelling growth through 2017. The large number of pathogens linked to disease in animals and plants is extensive, and current screening assays are not capable of expeditiously and simultaneously screening for a large number of pathogens in a single assay.

As de novo cataloging expands the count of species in the human microbiome and characterizes their distributions, metagenomic tools are needed to efficiently identify an agent strongly associated with a disease. The ability to assess a microbiome will be necessary to understand interactions between pathogens, and pathogen interactions with commensal organisms, host genetics, and environmental factors. In 2008, over 2 million cases of cancer worldwide (20% of all tumors) were associated with one of ten infectious agents: seven viruses (papillomavirus, hepatitis B or C, Epstein-Barr virus, human herpesvirus 8, and T-cell leukemia virus type 1), one bacterium (*Helicobacter pylori*), and two helminthes (schistosomes and liver flukes) which are major contributors to the cancers as etiological agents (de Martel et al. *Lancet Oncol* 2012; 13(6):607-615). Considering the thousands of species that comprise the normal human microbiome (Relman. *Nature* 2012; 486(7402):194-195), it is likely that microorganism communities substantially influence normal physiology as well as the causes of and responses to diseases (Laass et al. *Autoimmun Rev* 2014), including cancer. These effects are the subject of intense investigation in tissues known to have resident microbiomes such as the gastrointestinal tract (Laass et al. *Autoimmun Rev* 2014; Major and Spiller. *Curr Opin Endocrinol Diabetes Obes* 2014; 21(1):15-21; Schwarzberg et al. *PLoS One* 2014; 9(1):e86708; Scharschmidt and Fischbach. *Drug Discov Today Dis Mech* 2013; 10(3-4)), skin (Scharschmidt and Fischbach. *Drug Discov Today Dis Mech* 2013; 10(3-4)) and airway (Martinez et al. *Ann Am Thorac Soc* 2013; 10 Suppl:S170-179; Segal et al. *Ann Am Thorac Soc* 2014; 11(1):108-116; Sze et al. H *Ann Am Thorac Soc* 2014; 11 Suppl 1:S77) and in immune and inflammatory responses (Gjymishka et al. *Immunotherapy* 2013; 5(12): 1357-1366; Kamada and Nunez. *Gastroenterology* 2014; Koboziev et al. *Free Radic Biol Med* 2013; 68C:122-133; Ooi et al. *PLoS One* 2014; 9(1):e86366). Microbiome profiling is also uncovering less obvious roles for microbes and their presence in unexpected locations; examples relevant to cancer include modulation of tumor microenvironments (Iida et al. *Science* 2013; 342(6161):967-970) and dysbiosis of bacterial populations in breast cancer tissues (Xuan et al, *PLoS One* 2014; 9(1):e83744).

Existing strategies for detecting pathogens associated with disease require that samples be obtained from the infected subject, and a number of techniques utilized to identify the pathogen (see, e.g., FIGS. 1A and 1B). These techniques typically include enzyme linked immuno-absorbent assays (ELISA), specific antibodies against a specific protein of the suspected pathogen, culture of the pathogen in vitro in the laboratory, and PCR amplification strategies. PCR amplification using universal 16S ribosomal RNA primers, followed by amplicon sequencing, is the most widely used strategy for microbiome studies and provides an effective discovery tool (Cox et al. *Hum Mol Genet* 2013; 22(R1):R88-94), but only for bacterial species with amplicons that survive population PCR and not for viruses or eukaryotic microorganisms. 16S rRNA sequencing can also be used to screen large sets of samples, but may not discriminate between strains or report the presence of genomic variants or pathogenicity factors. Deep sequencing of the total DNA from a sample can identify bacterial, viral and other microbiome members (The Human Microbiome Project Consortium. *Nature* 2012; 486(7402):207-214; Cox et al. *Hum Mol Genet* 2013; 22(R1):R88-94; Ma et al. *J Virol* 2014), but with a severe penalty in efficiency. Even at the as-yet unrealized goal of $1000 per genome, total DNA sequencing is an expensive method for screening hundreds or thousands of test and control samples to detect associations of pathogens with disease. Depending on the specimen sampled, the data may overwhelmingly be from host human sequences, creating an unnecessarily large search space for locating pathogen signatures and resulting in the majority of sequence reads being discarded.

DNA microarrays have been used for metagenomics. The Lawrence Berkeley Lab/Affymetrix PhyloChip is based on ribosomal RNA sequences (Brodie et al. *Appl Environ Microbiol* 2006; 72(9):6288-6298). An academically developed Virochip has probes for 1500 viruses (Chen et al. *J Vis Exp* 2011 (50)) and has successfully detected viruses in pathology samples. The Virochip platform is limited to viruses and assays RNA that is reversed transcribed to cDNA for PCR amplification (Chen et al. *J Vis Exp* 2011 (50)). The Glomics GeoChip 4.0 focuses on RNA expression by bacteria in the human microbiome (Tu et al. *Mol Ecol Resour* 2014), and covers bacteriophage but no other viruses nor any eukaryotic microorganisms. PathGen Dx has launched a PathChip Kit that features an Affymetrix microarray for all known viruses and a broad selection of bacteria (Wong et al. *Genome Biol* 2007; 8 (5):R93), but no eukaryotic pathogens. These and other array-based tools illustrate the demand for methods to quickly and economically screen sets of samples for broad microbial content, including species beyond bacteria (Norman et al., *Gastroenterology* 2014).

Because current methods for detecting and identifying pathogenic and etiological agents are inadequate, compositions and methods for expeditiously and simultaneously detecting and identifying multiple pathognes, including all currently known pathogens, are urgently required. Such compositions and methods are also useful for the diagnosis of pathogen-associated disease, including infectious diseases and cancer, and for gaining understanding of disease states resutling from co-infection by multiple pathogens. The current invention fulfills these needs.

SUMMARY OF THE INVENTION

As described herein, the present invention features compositions and methods for the detection of one or more biomarkers in a sample comprising genetic material from multiple sources and/or organisms (e.g., metagenomes, microbiomes). In particular, Applicants have developed methods for generating panels or sets of nucleotides for the detection of genetic material from multiple pathogenic organisms and agents (e.g. viruses), as well as methods for preparing samples for analysis comprising total nucleic acid extraction (e.g., DNA and RNA).

In certain embodiments, the invention features nucleotide arrays and methods for simultaneously detecting and identifying multiple types of pathogens, including viruses, bacteria, fungi, protozoa and helminths, present in a sample. Further, the arrays and methods of the invention can be used to detect heretofore unknown pathogens present in a sample, based on the presence of a region of conserved nucleic acid sequence in the heretofore unknown pathogen. In one embodiment, the pathogen's nucleic acid is derived from a sample obtained from an individual suspected to be or known to be infected with a pathogen. Detection of an infectious agent can be used to guide patient care and treatment selection (e.g., antimicrobial, antiviral, antifungal, antibacterial, or antiparasitic therapy).

The arrays and methods disclosed herein can be used to expeditiously screen a sample for the presence of both known and as-yet unknown pathogens by comparing the pathogen's nucleic acid sequence in a sample to characteristic regions of sequence common among a related group of pathogens.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

A "biomarker" or "marker" as used herein generally refers to a nucleic acid molecule, clinical indicator, protein, or other analyte that is associated with a disease. In certain embodiments, a nucleic acid biomarker is indicative of the presence in a sample of a pathogenic organism, including but not limited to, viruses, viroids, bacteria, fungi, helminths, and protozoa. In various embodiments, a marker is differentially present in a biological sample obtained from a subject having or at risk of developing a disease (e.g., an infectious disease) relative to a reference. A marker is differentially present if the mean or median level of the biomarker present in the sample is statistically different from the level present in a reference. A reference level may be, for example, the level present in an environmental sample obtained from a clean or uncontaminated source. A reference level may be, for example, the level present in a sample obtained from a healthy control subject or the level obtained from the subject at an earlier timepoint, i.e., prior to treatment. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. The differential presence of a marker of the invention in a subject sample can be useful in characterizing the subject as having or at risk of developing a disease (e.g., an infectious disease), for determining the prognosis of the subject, for evaluating therapeutic efficacy, or for selecting a treatment regimen.

By "agent" is meant any nucleic acid molecule, small molecule chemical compound, antibody, or polypeptide, or fragments thereof.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

By "biologic sample" is meant any tissue, cell, fluid, or other material derived from an organism.

By "capture reagent" is meant a reagent that specifically binds a nucleic acid molecule or polypeptide to select or isolate the nucleic acid molecule or polypeptide.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

By "detectable moiety" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "fragment" is meant a portion of a nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 5, 10, 15, 20, 30, 40, 50, 60, 70, 80, 90, or 100 nucleotides.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "reference" is meant a standard of comparison. As is apparent to one skilled in the art, an appropriate reference is where an element is changed in order to determine the effect of the element. In one embodiment, the level of a target nucleic acid molecule present in a sample may be compared to the level of the target nucleic acid molecule present in a clean or uncontaminated sample. For example, the level of a target nucleic acid molecule present in a sample may be compared to the level of the target nucleic acid molecule present in a corresponding healthy cell or tissue or in a diseased cell or tissue (e.g., a cell or tissue derived from a subject having a disease, disorder, or condition).

By "Marker profile" is meant a characterization of the signal, level, expression or expression level of two or more markers (e.g., polynucleotides).

As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring. Nucleic acid molecules useful in the methods of the invention include any nucleic acid molecule that specifically binds a target nucleic acid (e.g., a nucleic acid biomarker). Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95%, 96%, 97%, 98%, or even 99% or more identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the term "sample" includes a biologic sample such as any tissue, cell, fluid, or other material derived from an organism.

By "specifically binds" is meant a compound (e.g., nucleic acid probe or primer) that recognizes and binds a molecule (e.g., a nucleic acid biomarker), but which does not substantially recognize and bind other molecules in a sample, for example, a biological sample.

By "subject" is meant a mammal, including, but not limited to, a human or non-human mammal, such as a bovine, equine, canine, ovine, or feline. The term "subject" may refer to an animal, which is the object of treatment, observation, or experiment (e.g., a patient).

By "target nucleic acid molecule" is meant a polynucleotide to be analyzed. Such polynucleotide may be a sense or antisense strand of the target sequence. The term "target nucleic acid molecule" also refers to amplicons of the original target sequence. In various embodiments, the target nucleic acid molecule is one or more nucleic acid biomarkers As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein. It is also to be understood that the terminology used herein is for the purpose of describing particular embodiments only, and is not intended to be limiting.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other features and advantages of the invention will be apparent from the following description of the desirable embodiments thereof, and from the claims.

BRIEF DESCRIPTION OF THE DRAWINGS

FIG. 1, comprising FIG. 1A and FIG. 1B, depicts several current options for testing for the presence of a microorganism (e.g., a pathogenic microorganism). FIG. 1A depicts features involved in current testing options. In particular, current testing options require culturing for subsequent analysis by antibody bead capture, DNA-bead capture, polymerase chain reaction, immunoassay, DNA probe amplification, colony counting, and restriction digest mapping. Current testing options are also limited to one targeted organism analyzed per test. FIG. 1B is a table comparing specific features of current testing options.

FIG. 2, comprising FIG. 2A depicts use of a metagenome for probe selection for the PathoChip. Sequence accessions for all viruses and selected human pathogenic microorganisms were retrieved from the NCBI DNA sequence databases and concatenated to form a metagenome. Wherever possible, regions of target sequence unique to the accession (a, c) were used to select multiple 60 nt probes (1, 2, 4-6 in figure) for microarray synthesis, and probes to target regions that share similar sequences in at least two viral accessions (b) were also identified. Probes to prokaryotic and eukaryotic pathogens may map to intergenic, gene or ribosomal RNA sequences, or a mixture of target types, depending on the availability of sequence data. FIG. 2B is a schematic of the process for designing the PathoChip. Parallel and iterative design processes were used to assemble the PathoChip probe collection that covers unique and conserved target regions, supplemented with high-resolution probe tiling for known cancer-associated microorganisms.

FIG. 3, comprising FIG. 3A depicts that a culturing step is not required to prepare a sample for use with the PathoChip. FIG. 3B depicts a nucleic acid extraction method for the preparation of a sample containing both DNA and RNA.[1] It is unknown what bacterial/viral materials may be lost during xylene de-paraffinization,[2] The pellet from this spin should contain large genomic DNA, cells that remain intact, and cellular debris. The spin is probably not sufficient to pellet intact viral particles,[3] Viral DNA here is only from unpelleted intact particles. Viral DNA released from lysed host cells should be in pellet. Viral RNA is from intact particles or lysed host cells,[4] 80 or 90° C. reverses formalin crosslinking.[5] A small aliquot to retain the chance of recovering nucleic acid from any unpelleted, intact particles or cells.

FIG. 4 lists foodborne pathogens the panel of probes in PathoChip v3 is capable of detecting, including 76 organisms using multiple targeting sequences.

FIG. 5, comprising FIGS. 5A through FIG. 5I, depicts identification of probes used for detecting a targeted species. FIG. 5A is a graph depicting selection and discarding of probes (e.g., for detecting *Clostridium perfringens*). FIG. 5B is a graph depicting probe selection for detecting *Legionella pneumophila*. FIG. 5C is a graph depicting probe selection for detecting *Yersinia enterocolitica*. FIG. 5D is a graph depicting probe selection for detecting *Escherichia coli*. FIG. 5E is a graph depicting probe selection for detecting *Vibrio cholerae*. FIG. 5F is a graph depicting probe selection for detecting *Clostridium perfringens*. FIG. 5G is a graph depicting probe selection for detecting *Salmonella enterica*. FIG. 5H is a graph depicting probe selection for detecting *Shigella flexneri*. FIG. 5I is a graph depicting probe selection for detecting *Listeria monocytogenes*. All probes for each target were analyzed to identify probe subsets with high sensitivity, using aliquots of diluted stock containing 1000, 100, 10 or 1 cell of each target for DNA+RNA extraction, amplification, and hybridization to PathoChip v3. For each targeted organism, probes were selected that demonstrated appropriate detection response. Subsets of probes selected in this manner were used as an assay panel in subsequent studies.

FIG. 6, comprising FIG. 6A is a graph depicting summation of signal from selected probes to detect *Salmonella enterica*. FIG. 6B is a graph depicting summation of signal from selected probes to detect *Listeria monocytogenes*. FIG. 6C is a graph depicting summation of signal from selected probes to detect *Shigella flexneri*. FIG. 6D is a graph depicting summation of signal from selected probes to detect *Clostridium perfringens*. FIG. 6E is a graph depicting summation of signal from selected probes to detect *Yersinia enterocolitica*. FIG. 6F is a graph depicting summation of signal from selected probes to detect *Vibrio cholerae*. FIG. 6G is a graph depicting probe selection for detecting *Escherichia coli* O157:H7. FIG. 6H is a graph depicting probe selection for detecting *Legionella pneumophila*.

FIGS. 7A through FIG. 7H, shows detection signals of selected probe sets specific for various bacteria when mixed with human and lettuce cells. FIG. 7A is a graph depicting detection signal computed as sum of selected probes for each test sample (solid line) and the control sample background (dotted line) (e.g., for detecting *Clostridium perfringens* mixed with human and lettuce cells). FIG. 7B is a graph depicting detection signals for selected probe sets to assay samples containing various numbers of *Escherichia coli* O157:H7 cells mixed with human and lettuce cells. FIG. 7C is a graph depicting detection signals for selected probe sets to assay samples containing various numbers of *Legionella pneumophila* cells mixed with human and lettuce cells. FIG. 7D is a graph depicting detection signals for selected probe sets to assay samples containing various numbers of *Listeria monocytogenes* cells mixed with human and lettuce cells. FIG. 7E is a graph depicting detection signals for selected probe sets to assay samples containing various numbers of *Salmonella enterica* cells mixed with human and lettuce cells. FIG. 7F is a graph depicting detection signals for selected probe sets to assay samples containing various numbers of *Shigella flexneri* cells mixed with human and lettuce cells. FIG. 7G is a graph depicting detection signals for selected probe sets to assay samples containing various numbers of *Vibrio cholerae* cells mixed with human and lettuce cells. FIG. 7H is a graph depicting detection signals for selected probe sets to assay samples containing various numbers of *Yersinia enterocolitica* cells mixed with human and lettuce cells. A small number of pathogen cells in a background of a large number of host cells can be detected, but with less absolute signal compared to pure pathogen cultures (see FIG. 6). The difference between test signal and host-only control signal indicates detection ability. The ability to quantify the amount of pathogen requires more cells than ability to detect merely presence or absence.

FIGS. 8A through FIG. 8H, shows detection signals of selected probe sets specific for various bacteria when mixed with milk. FIG. 8A is a graph depicting detection signal computed as sum of selected probes for each test sample (solid line) and the control sample background (dotted line) (e.g., for detecting *Clostridium perfringens* in milk). FIG. 8B is a graph depicting detection signals for selected probe sets to assay samples containing various numbers of *Toxoplasma gondii* cells in milk. FIG. 8C is a graph depicting detection signals for selected probe sets to assay samples containing various numbers of *Vibrio cholerae* cells in milk. FIG. 8D is a graph depicting detection signals for selected probe sets to assay samples containing various numbers of *Yersinia enterocolitica* cells in milk. FIG. 8E is a graph depicting detection signals for selected probe sets to assay samples containing various numbers of *Escherichia coli* O157:H7 cells in milk. FIG. 8F is a graph depicting detection signals for selected probe sets to assay samples containing various numbers of *Legionella pneumophila* cells in milk. FIG. 8G is a graph depicting detection signals for selected probe sets to assay samples containing various numbers of *Salmonella enterica* cells in milk. FIG. 8H is a graph depicting detection signals for selected probe sets to assay samples containing various numbers of *Shigella flexneri* cells in milk.

FIG. 9, comprising FIGS. 9A through FIG. 9H, shows detection signals of selected probe sets specific for various bacteria when mixed with tomato. FIG. 9A is a graph depicting detection signals for selected probe sets to assay samples containing various numbers of *Clostridium perfringens* cells mixed with tomato. FIG. 9B is a graph depicting detection signals for selected probe sets to assay samples containing various numbers of *Toxoplasma gondii* cells mixed with tomato. FIG. 9C is a graph depicting detection signals for selected probe sets to assay samples containing various numbers of *Vibrio cholerae* cells mixed with tomato. FIG. 9D is a graph depicting detection signals for selected probe sets to assay samples containing various numbers of *Yersinia enterocolitica* cells mixed with tomato. FIG. 9E is a graph depicting detection signals for selected probe sets to assay samples containing various numbers of *Escherichia coli* O157:H7 cells mixed with tomato. FIG. 9F is a graph depicting detection signals for selected probe sets to assay samples containing various numbers of *Legionella pneumophila* cells mixed with tomato. FIG. 9G is a graph depicting detection signals for selected probe sets to assay samples containing various numbers of *Shigella flexneri* cells mixed with tomato. FIG. 9H is a graph depicting detection signals for selected probe sets to assay samples containing various numbers of *Salmonella enterica* cells mixed with tomato.

FIG. 10A through FIG. 10D, shows detection signals of selected probe sets specific for various bacteria when mixed with clam. FIG. 10A is a graph depicting detection signals for selected probe sets to assay samples containing various numbers of *Clostridium perfringens* cells mixed with clam. FIG. 10B is a graph depicting detection signals for selected probe sets to assay samples containing various numbers of *Toxoplasma gondii* cells mixed with clam. FIG. 10C is a graph depicting detection signals for selected probe sets to assay samples containing various numbers of *Vibrio cholerae* cells mixed with clam. FIG. 10D is a graph depicting detection signals for selected probe sets to assay samples containing various numbers of *Yersinia enterocolitica* cells mixed with clam.

FIG. 12, comprising FIGS. 12A and 12B, are heat map data showing hybridization signal of all the probes of the accessions selected by Accession Analysis. FIG. 12A are heat maps generated from analysis of patient and control samples using the PathoChip. FIG. 12B shows the heat maps after eliminating probes that were either undetected or were also present in the control. The remaining probes indicated fungal hybridization signals.

DETAILED DESCRIPTION OF THE INVENTION

Figure 2A:
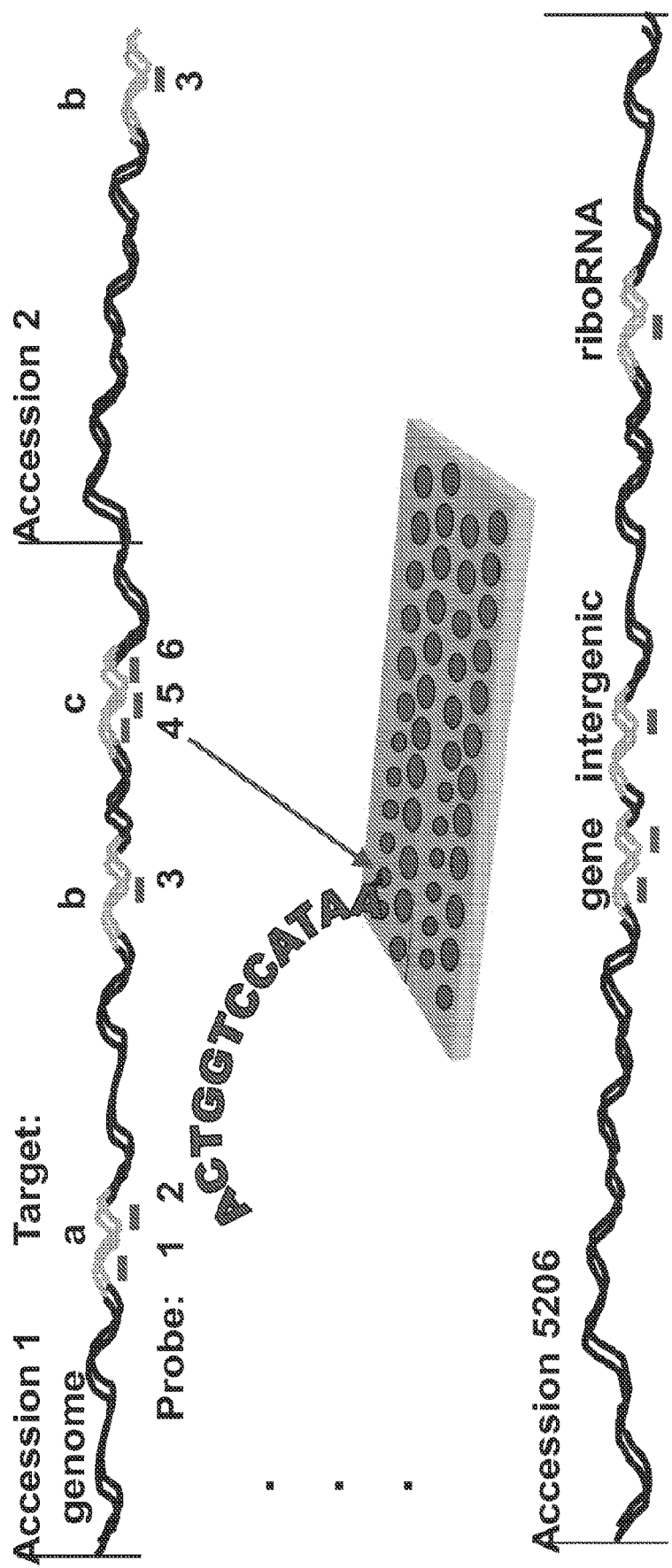
FIGS. 2A and FIG. 2B, depicts design of the PathoChip.

As described herein, the present invention features compositions and methods for the detection of one or more biomarkers in a sample comprising genetic material from multiple sources and/or organisms (e.g., metagenomes, microbiomes). In particular, Applicants have developed methods for generating panels or sets of nucleotides for the detection of genetic material from multiple pathogenic organisms and agents (e.g. viruses), as well as methods for preparing samples for analysis comprising total nucleic acid extraction (e.g., DNA and RNA).

As described herein, development of the PathoChip platform containing probes for all public virus sequences and hundreds of pathogenic bacteria, fungi, and helminthes, provides wide coverage of pathogens in an economical format. The PathoChip platform is differentiated from current technologies by providing faster results that are important to manufacturers and distributors challenged by product shelf life. In one aspect, the PathoChip platform can be used to perform clinical assays for patient diagnosis, thus having the potential to impact patient therapy and care. Where possible, multiple probes to independent regions of the target genome are used to improve opportunity for detection. While PathoChip content was developed from sequences to known targets, some ability to discover new strains or organisms is provided by the inclusion of probes to sequences that are conserved within and between viral families; a previously unknown virus with homology to a conserved sequence may produce a corresponding hybridization signal at such a probe, if not to a complete probe set. A supporting workflow is described for profiling biological and environmental samples, and includes simultaneous detection of DNA and RNA to expand the range of targets available for hybridization. The PathoChip platform has demonstrated success in non-food applications, as well as detection of major bacterial pathogens in food samples.

Target Nucleic Acid Molecules

Methods and compositions of the invention are useful for the identification of a target nucleic acid molecule in a test sample or material to be analyzed. Target sequences are amplified from any sample that comprises a target nucleic acid molecule, including but not limited to environmental, non-biological, and biological samples. Such samples may comprise fungi, spores, viruses, or cells (e.g., prokaryotes, eukaryotes). In specific embodiments, compositions and methods of the invention detect one or more pathogenic organisms, including viruses, viroids, bacteria, fungi, helminths, and/or protozoa.

Exemplary test samples include body fluids (e.g. blood, serum, plasma, amniotic fluid, sputum, urine, cerebrospinal fluid, lymph, tear fluid, feces, or gastric fluid), tissue extracts, culture media (e.g., a liquid in which a cell, such as a pathogen cell, has been grown), environmental samples, agricultural products or other foodstuffs, and their extracts, DNA identification tags. If desired, the sample is purified prior to detection using any standard method typically used for isolating a nucleic acid molecule from a biological sample. In one embodiment, a target nucleic acid of a pathogen is amplified by primer/template oligonucleotides to detect the presence of a pathogen in a sample. Exemplary pathogens include fungi, bacteria, viruses and yeast. Such pathogens may be detected by identifying a nucleic acid molecule encoding a pathogen nucleic acid sequence, in a test sample.

In one embodiment, a sample is a biological sample, such as a tissue sample. The level of one or more polynucleotide biomarkers (e.g., to detect or identify viruses, bacteria, fungi, helminths, and/or protozoa) is measured in different types of biologic samples. In one embodiment, the biologic sample is a tissue sample that includes cells of a tissue or organ, for example, from a biopsy. In another embodiment, the biologic sample is a biologic fluid sample. Biological fluid samples include cerebrospinal fluid blood, blood serum, plasma, urine, and saliva, or any other biological fluid useful in the methods of the invention.

In another embodiment, a sample is an environmental sample, such as soil, sediment water, or air. Environmental samples can be obtained from an industrial source, such as a farm, waste stream, or water source. For environmental applications, test samples may include water, liquid extracts of air filters, soil samples, building materials (e.g., drywall, ceiling tiles, wall board, fabrics, wall paper, and floor coverings), environmental swabs, or any other sample.

Target nucleic acid molecules include double-stranded and single-stranded nucleic acid molecules (e.g., DNA, RNA, and other nucleobase polymers known in the art capable of hybridizing with a nucleic acid molecule described herein). RNA molecules suitable for detection with a detectable oligonucleotide probe or detectable primer/template oligonucleotide of the invention include, but are not limited to, double-stranded and single-stranded RNA molecules that comprise a target sequence (e.g., messenger RNA, viral RNA, ribosomal RNA, transfer RNA, microRNA and microRNA precursors, and siRNAs or other RNAs described herein or known in the art). DNA molecules suitable for detection with a detectable oligonucleotide probe or primer/template oligonucleotide of the invention include, but are not limited to, double stranded DNA (e.g., genomic DNA, plasmid DNA, mitochondrial DNA, viral DNA, and synthetic double stranded DNA). Single-stranded DNA target nucleic acid molecules include, for example, viral DNA, cDNA, and synthetic single-stranded DNA, or other types of DNA known in the art. In general, a target sequence for detection is between about 30 and about 300 nucleotides in length (e.g., 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300 nucleotides). In a specific embodiment the target sequence is about 60 nucleotides in length. A target sequence for detection may also have at least about 70, 80, 90, 95, 96, 97, 98, 99, or even 100% identity to a probe sequence. Probe sequences may be longer or shorter than the target sequence. For example, a 60-nucleotide probe may hybridize to at least about 44 nucleotides of a target sequence.

In particular embodiments, a biomarker is a biomolecule (e.g., nucleic acid molecule) that is differentially present in a sample (e.g., a biological, non-biological, or environmental sample). For example, a biomarker is taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for characterizing a disease.

Probe Selection

The invention provides sets of probes are selected for detecting multiple target nucleic acid molecules (e.g., corresponding to multiple bioorganisms). In various embodiments, the invention provides a metagenome, its construction, and its use in the methods of the invention. As used herein "metagenome" refers to genetic material from more than one organism, e.g., in an environmental sample. The metagenome is used to select the sets of probes and/or to validate probe sets. In some embodiments, the metagenome comprises the sequences or genomes of about 20, 30, 40, 50, 60, 70, 80, 90, 100, 200, 300, 400, 500, 1000, 1500, 2000 or more organisms. In one example, the nucleic acid sequences of thousands of organisms were linked to generate a metagenome comprising 58 chromosomes.

Discrete Metagenome Probe Selection
A. Download individual genomes, genes and partial sequences into a local database of accessions
B. Mask low complexity sequences using bioinformatic tools. In one example, low complexity sequences are masked using mdust (http://doc.bioperl.org/bioperl-run/lib/Bio/Tools/Run/Mdust.html) followed by BLASTN 2.0MP-WashU31 identification of unique regions in viral accessions.
C. BLASTN sequence comparison of each accession against all other accessions
D. Identify specific target regions within each accession
  1. 250-300 bp regions
  2. No more than 50 contiguous nucleotides with 70% or greater sequence homology to any other accession or to the human genome
E. Supplement specific targets
  1. Identify any accessions with zero or one target region
  2. Relax stringency parameters to no more than 30 contiguous nucleotides with 50% or greater sequence homology to any other accession, but no more than 50 contiguous nucleotides with 70% or greater sequence homology to human genome
  3. Re-run target region identification on accession subset from 1.E.1.
F. Identify conserved target regions
  1. 70-300 bp regions that have 70% or greater homology with at least one other accession
  2. Remove conserved targets with 50 or more contiguous nucleotides with 70% or greater sequence homology to human genome
G. Choose probes
  1. Run Agilent array CGH probe selection algorithm on specific and conserved target regions
  2. Rank probes by Agilent design score
  3. Select 1-3 highest ranking probes from 1-5 specific target regions in each accession
  4. Select 1-3 highest ranking probes from each conserved target region Concatenated Metagenome Probe Selection
A. Download individual genomes, genes and partial sequences into a local database of accessions
B. Compile all accessions into a single concatenated metagenome to facilitate use of genomics bioinformatics tools
  1. Place 100 nonspecific nucleotides ("N") as spacers between each accession
  2. Join accessions and spacers into chromosomes of 6-10 million bases
C. Run Agilent array CGH probe selection algorithm for specificity within the metagenome
D. Filter probes for specificity against human, mouse, and/or other mammalian genomes
E. Choose specific probes
  1. Rank probes by Agilent design score
  2. Select 10-20 highest ranking probes from each accession
  3. Require at least 100 bp separation between probes
F. Choose conserved probes
  1. Identify conserved regions as in 1.F.
  2. Select 5-10 highest ranking probes from each conserved region
  3. Require at least 100 bp separation between probes
G. Empirical probe selection
  1. Manufacture microarrays containing all specific and conserved probes
  2. Hybridize microarrays to labeled human DNA
  3. Select 5-10 specific probes from each accession with lowest cross-hybridization signal
  4. Select 3-5 conserved probes from each conserved regions with lowest cross-hybridization signal Sample Preparation The invention also provides a means for analyzing multiple types of nucleic acids present in a sample, including DNA and RNA. In various embodiments, sample preparation involves extracting a mixture of nucleic acid molecules (e.g., DNA and RNA). In other embodiments, sample preparation involves extracting a mixture of nucleic acids from multiple organisms, cell types, infectious agents, or any combination thereof. In one embodiment, sample preparation involves the workflow below.
A. Fragment genomic DNA
B. Convert total RNA to first strand cDNA by random-primed reverse transcriptase C. Label genomic DNA with biotin or fluorescent dye by chemical or enzymatic incorporation
D. Label cDNA with biotin or fluorescent dye by chemical or enzymatic incorporation
E. Label a mixture of genomic DNA and cDNA in the same chemical or enzymatic reaction
F. Mix C+D and co-hybridize to microarray of probes
G. Hybridize E to microarray of probes
H. Amplify targeted genomic DNA
 1. Use whole-genome amplification (GE GenomiPhi, Sigma WGA, NuGEN Ovation DNA) to non-specifically amplify genomic DNA
 2. Use amplified products as input for 4.C, or 4.E.
I. Amplify targeted total RNA
 1. Use whole-transcriptome amplification (Sigma WTA, Ambion in vitro transcription, NuGEN Ovation RNA) to non-specifically amplify total RNA
 2. Use amplified products as input for 4.D. or 4.E.

The samples are hybridized to the microarray (e.g., PathoChip), and the microarrays are washed at various stringencies. Microarrays are scanned for detection of fluorescence. Background correction and inter-array normalization algorithms are applied. Detection thresholds are applied. The results are analyzed for statistical significance.

Nucleic Acid Amplification

Target nucleic acid sequences are optionally amplified before being detected. The term "amplified" defines the process of making multiple copies of the nucleic acid from a single or lower copy number of nucleic acid sequence molecule. The amplification of nucleic acid sequences is carried out in vitro by biochemical processes known to those of skill in the art. Prior to or concurrent with identification, the viral sample may be amplified by a variety of mechanisms, some of which may employ PCR. For example, primers for long range PCR may be designed to amplify regions of the sequence. For RNA viruses a first reverse transcriptase step may be used to generate double stranded DNA from the single stranded RNA. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675. The sample may be amplified on the array. See, for example, U.S. Pat. No. 6,300,070 and U.S. Ser. No. 09/513,300.

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed PCR (CP-PCR) (U.S. Pat. No. 4,437,975), arbitrarily primed PCR (AP-PCR) (U.S. Pat. Nos. 5,413,909, 5,861,245) and nucleic acid based sequence amplification (NABSA) (see, U.S. Pat. Nos. 5,409,818, 5,554,517, and 6,063,603). Other amplification methods that may be used are described in, U.S. Pat. Nos. 5,242,794, 5,494,810, 4,988,617 and in U.S. Ser. No. 09/854,317.

Additional methods of sample preparation and techniques for reducing the complexity of a nucleic sample are described in Dong et al., Genome Research 11, 1418 (2001), in U.S. Pat. Nos. 6,361,947, 6,391,592 and U.S. Ser. Nos. 09/916,135, 09/920,491 (US Patent Application Publication 20030096235), Ser. No. 09/910,292 (US Patent Application Publication 20030082543), and Ser. No. 10/013,598.

Detection of Biomarkers

The biomarkers of this invention can be detected by any suitable method. The methods described herein can be used individually or in combination for a more accurate detection of the biomarkers. Methods for conducting polynucleotide hybridization assays have been developed in the art. Hybridization assay procedures and conditions will vary depending on the application and are selected in accordance with the general binding methods known including those referred to in: Sambrook and Russell, Molecular Cloning: A Laboratory Manual ($3^{rd}$ Ed. Cold Spring Harbor, N.Y., 2001); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623. A data analysis algorithm (E-predict) for interpreting the hybridization results from an array is publicly available (see Urisman, 2005, Genome Biol 6:R78).

In one embodiment, the hybridized nucleic acids are detected by detecting one or more labels attached to, or incorporated within, the sample nucleic acids. The labels may be attached or incorporated by any of a number of means well known to those of skill in the art. In one embodiment, the label is simultaneously incorporated during the amplification step in the preparation of the sample nucleic acids. Thus, for example, PCR with labeled primers or labeled nucleotides will provide a labeled amplification product. In another embodiment, transcription amplification, as described above, using a labeled nucleotide (e.g. fluorescein-labeled UTP and/or CTP) incorporates a label into the transcribed nucleic acids. In another embodiment PCR amplification products are fragmented and labeled by terminal deoxytransferase and labeled dNTPs. Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing the nucleic acid and subsequent attachment (ligation) of a nucleic acid linker joining the sample nucleic acid to a label (e.g., a fluorophore). In another embodiment label is added to the end of fragments using terminal deoxytransferase.

Detectable labels suitable for use in the present invention include any composition detectable by spectroscopic, photochemical, biochemical, immunochemical, electrical, optical or chemical means. Useful labels in the present invention include, but are not limited to: biotin for staining with labeled streptavidin conjugate; anti-biotin antibodies, magnetic beads (e.g., Dynabeads™.); fluorescent dyes (e.g., fluorescein, texas red, rhodamine, green fluorescent protein, and the like); radiolabels (e.g., $^3H$, $^{125}I$, $^{35}S$, $^4C$, or $^{32}P$); phosphorescent labels; enzymes (e.g., horse radish peroxidase, alkaline phosphatase and others commonly used in an ELISA); and colorimetric labels such as colloidal gold or colored glass or plastic (e.g., polystyrene, polypropylene, latex, etc.) beads. Patents teaching the use of such labels include U.S. Pat. Nos. 3,817,837, 3,850,752, 3,939,350, 3,996,345, 4,277,437, 4,275,149 and 4,366,241.

Means of detecting such labels are well known to those of skill in the art. Thus, for example, radiolabels may be detected using photographic film or scintillation counters; fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Ser. Nos. 10/389, 194, 60/493,495 and in PCT Application PCT/US99/06097 (published as WO99/47964).

Detection by Biochip

In aspects of the invention, a sample is analyzed by means of a biochip (also known as a microarray). The nucleic acid molecules of the invention are useful as hybridizable array elements in a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. U.S. Pat. Nos. 5,800,992 and 6,040,138 describe methods for making arrays of nucleic acid probes that can be used to detect the presence of a nucleic acid containing a specific nucleotide sequence. Methods of forming high-density arrays of nucleic acids, peptides and other polymer sequences with a minimal number of synthetic steps are known. The nucleic acid array can be synthesized on a solid substrate by a variety of methods, including, but not limited to, light-directed chemical coupling, and mechanically directed coupling. For additional descriptions and methods relating to resequencing arrays see U.S. patent application Ser. Nos. 10/658,879, 60/417,190, 09/381,480, 60/409,396, and U.S. Pat. Nos. 5,861,242, 6,027,880, 5,837, 832, 6,723,503.

Detection by Nucleic Acid Biochip

In aspects of the invention, a sample is analyzed by means of a nucleic acid biochip (also known as a nucleic acid microarray). To produce a nucleic acid biochip, oligonucleotides may be synthesized or bound to the surface of a substrate using a chemical coupling procedure and an ink jet application apparatus, as described in PCT application WO95/251116 (Baldeschweiler et al.). Alternatively, a gridded array may be used to arrange and link cDNA fragments or oligonucleotides to the surface of a substrate using a vacuum system, thermal, UV, mechanical or chemical bonding procedure. Exemplary nucleic acid molecules useful in the invention include polynucleotides that specifically bind nucleic acid biomarkers to one or more pathogenic organisms, and fragments thereof.

A nucleic acid molecule (e.g. RNA or DNA) derived from a biological sample may be used to produce a hybridization probe as described herein. The biological samples are generally derived from a patient, e.g., as a bodily fluid (such as blood, blood serum, plasma, saliva, urine, ascites, cyst fluid, and the like); a homogenized tissue sample (e.g., a tissue sample obtained by biopsy); or a cell isolated from a patient sample. For some applications, cultured cells or other tissue preparations may be used. The mRNA is isolated according to standard methods, and cDNA is produced and used as a template to make complementary RNA suitable for hybridization. Such methods are well known in the art. The RNA is amplified in the presence of fluorescent nucleotides, and the labeled probes are then incubated with the microarray to allow the probe sequence to hybridize to complementary oligonucleotides bound to the biochip.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide Stringent temperature conditions will ordinarily include temperatures of at least about 30° C., of at least about 37° C., or of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In embodiments, hybridization will occur at 37° C. in 500 mM NaCl, 50 mM trisodium citrate, 1% SDS, 35% formamide, and 100 µg/ml denatured salmon sperm DNA (ssDNA). In other embodiments, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., of at least about 42° C., or of at least about 68° C. In embodiments, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In other embodiments, wash steps will occur at 68 C in 15 mM NaCl, 1.5 mM trisodium citrate, and 0.1% SDS. Additional variations on these conditions will be readily apparent to those skilled in the art.

Detection system for measuring the absence, presence, and amount of hybridization for all of the distinct nucleic acid sequences are well known in the art. For example, simultaneous detection is described in Heller et al., Proc. Natl. Acad. Sci. 94:2150-2155, 1997. In embodiments, a scanner is used to determine the levels and patterns of fluorescence.

Diagnostic Assays

The present invention provides a number of diagnostic assays that are useful for the identification or characterization of a disease or disorder (e.g., infectious disease), or a propensity to develop such a condition. In one embodiment, a disease, disorder, or condition is characterized by quantifying the level of one or more biomarkers from one or more pathogenic organisms, including viruses, viroids, bacteria, fungi, helminths, and protozoa. While the examples provided below describe specific methods of detecting levels of these markers, the skilled artisan appreciates that the invention is not limited to such methods. Marker levels are quantifiable by any standard method, such methods include, but are not limited to real-time PCR, Southern blot, PCR, and/or mass spectroscopy.

The level of any two or more of the markers described herein defines the marker profile of a disease, disorder, condition. The level of marker is compared to a reference. In one embodiment, the reference is the level of marker present in a control sample obtained from a patient that does not have the disease, disorder, or condition. In another embodiment, the reference is a baseline level of marker present in a biologic sample derived from a patient prior to, during, or after treatment for a disease, disorder, or condition. In yet another embodiment, the reference is a standardized curve. The level of any one or more of the markers described herein (e.g., a combination of viral, bacterial, fungal, helminth, and/or protozoan biomarkers) is used, alone or in combination with other standard methods, to characterize the disease, disorder, or condition.

Implementation in Hardware and/or Software

The methods described herein can be implemented on general-purpose or specially programmed hardware or software. For example, the methods can be implemented by a computer readable medium. Accordingly, the present invention also provides a software and/or a computer program product configured to perform the algorithms and/or methods according to any embodiment of the present invention. It is well-known to a skilled person in the art how to configure software which can perform the algorithms and/or methods provided in the present invention. The computer-readable medium can be non-transitory and/or tangible. For example, the computer readable medium can be volatile memory (e.g., random access memory and the like) or non-volatile memory (e.g., read-only memory, hard disks, floppy discs, magnetic tape, optical discs, paper table, punch cards, and the like). The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., $2^{nd}$ ed., 2001).

The present invention may also make use of various computer program products and software for a variety of purposes, such as probe design, management of data, analysis, and instrument operation. (See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.) Additionally, the present invention may have preferred embodiments that include methods for providing genetic information over networks such as the Internet as shown in U.S. Ser. Nos. 10/197,621, 10/063,559 (US Pub No 20020183936), Ser. Nos. 10/065,856, 10/065,868, 10/328,818, 10/328,872, 10/423,403, and 60/482,389.

Kits

The invention provides kits for the detection of a biomarker, which is indicative of the presence of one or more biological agents capable of causing a disease, disorder, or condition. The kits may be used for detecting the presence of multiple biological agents capable of causing one or more diseasesor disorders. The kits may be used for the diagnosis of the disease, disorder, or condition. In some embodiments, the kit comprises a panel or collection of probes to nucleic acid biomarkers (e.g., PathoChip).

In some embodiments, the kit comprises one or more sterile containers which contain the panel of probes to nucleic acid biomarkers, or microaray chip. Such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

The instructions will generally include information about the use of the composition for the detection or diagnosis of a disease or disorder. In other embodiments, the instructions include at least one of the following: description of the therapeutic agent; dosage schedule and administration for treatment or prevention of disease, disorder, or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Materials and Methods

Microarray Design

National Center for Biotechnology Information (NCBI) databases for Genome, Gene and Nucleotide accessions were queried (www.ncbi.nlm.nih.gov/pubmed) for all taxonomy=virus annotations, and for accessions from prokaryotic and eukaryotic human pathogen lists compiled by literature searches and web resources (www.niaid.nih.gov: Emerging and Re-emerging Infectious Diseases, Category A, B, and C Priority Pathogens). The resulting accessions were assembled into a non-redundant concatenation with 100 N nucleotide separators between accessions. This metagenome was divided into 58 "chromosomes" each around 5-10 million nucleotides in length, and submitted to Agilent Technologies (Santa Clara Calif., USA) as a custom design project. Probe sequences (50-60 nt) were selected using the Agilent array comparative genomic hybridization (aCGH) design algorithms, and then filtered for low likelihood of cross-hybridization to human genomic sequences.

Independently, low complexity regions in the metagenome were masked using mdust (http://doc.bioperl.org/bioperl-run/lib/Bio/Tools/Run/Mdust.html) followed by BLASTN 2.0MP-WashU[31] identification of unique regions in viral accessions. Unique region criteria were 250-300 bp and <50 contiguous by with >70% identity to a sequence in any other metagenome accession. Conserved viral regions were similarly identified using criteria of 70-300 bp and >70% identity to at least one other virus but not to human sequences.

All Agilent designed probes that mapped to unique or conserved viral regions, or any prokaryotic or eukaryotic pathogen accession, were added to the microarray design by default if fewer than 10 probes were available for the source accession. Otherwise, the probes were filtered for minimum inter-probe spacing of 100 bp and distribution that roughly covers the full length of each accession while limiting the number of probes to 10-20 per accession. The number of probes was not restricted for known oncogenic organisms, creating a saturation tiling set covering these accessions' entire sequences to the extent possible with all available Agilent designed probes. The microarray was supplemented with predesigned aCGH probes for 660 genes and 602 intergenic regions from the human genome, and probes for *Saccharomyces cerevisiae*. Probes and accession annotations are available in the Gene Expression Omnibus (http://www.ncbi.nlm.nih.gov/geo/).

Sample Preparation

Total nucleic acid was extracted from the samples. Whole-genome amplifications (WGA) of genomic DNA and/or cDNA from random primed, reverse transcribed total RNA were performed with the Illustra GenomiPhi v2 kit (GE Healthcare Bio-Sciences, Pittsburgh Pa., USA), Ovation WGA System (NuGEN, San Carlos Calif., USA), and GenomePlex or TransPlex kits (WGA2, WTA2, Sigma-Aldrich, St. Louis Mo., USA) using vendor recommended protocols and input amounts. Amplification products were purified with the QIAquick PCR Purification Kit (Qiagen), and 2 ug used for Cy3 dye labeling by the SureTag Labeling Kit (Agilent). Cy5 dye labeling was performed on 2 ug of Human Reference DNA from the Agilent SureTag kit, without prior WGA (experiment 1, Table 1) or after WGA (all other experiments), as a control to report probe cross-hybridization to human (xhh) DNA. Labeled DNA was purified with SureTag kit spin columns and specific activities were calculated.

Microarray Production and Processing

SurePrint glass slide microarrays (Agilent) were manufactured with 60 nt DNA oligomers synthesized in 60,000 features on eight replicate arrays per slide. PathoChip v2a and v2b contained 60,000 probes to unique target regions or conserved plus saturation target regions, respectively. PathoChip v3 contained 37,704 probes to unique targets and 23,627 probes for conserved targets or to saturate known oncogenic agents.

Labeled samples were hybridized to microarrays as described in the Agilent Oligonucleotide Array-Based CGH for Genomic DNA Analysis protocol (version 7.2, G4410-90010). Master mixes containing aCGH blocking agent, HI-RPM hybridization buffer, and Cot-1 DNA (pilot assays only) were added to a mixture of the entire labeled test sample and the xhh control sample, denatured, and hybridized to arrays under 8-chamber gasket slides at 65° C. with 20 rpm rotation for 40 hours in an Agilent Hybridization Oven. Arrays were processed using Wash Procedure A, and scanned on an Agilent SureScan G4900DA Microarray Scanner.

Microarray Data Analysis

Scanned microarray images were analyzed using Agilent Feature Extraction software to calculate average pixel intensity and subtract local background for each feature. Images were manually examined to note any arrays affected by high background, scratches or other technical artifacts. Feature intensity distribution and channel balance were not used for quality control because most features are expected to have no signal, except for the control human probes.

Feature intensities for Cy3 and Cy5 channels were imported into Partek Genomics Suite (Partek Inc., St. Louis Mo., USA). The average intensity for human intergenic control probes was calculated for co-hybridized test and xhh samples, and a scale factor determined which would make the Cy5 xhh average equal to the Cy3 average. The Cy5 intensities for all PathoChip probes were then multiplied by the scale factor to normalize for differences in dye performance Cy3/Cy5 ratios and Cy3-Cy5 subtractions were calculated for each probe to provide input for dual-channel or single-channel analysis pipelines respectively. Accession Average (AccAvg) was defined as the average Cy3 or Cy5 intensity across all probes for one accession, and Accession Signal (AccSig) was defined as AccAvg(Cy3)-AccAvg (Cy5).

Model-based Analysis of Tiling-arrays (MAT)[32] as implemented in Partek was used for sliding window analysis of probe signals (Cy3 minus Cy5) for each sample. MAT parameters were p-value cutoff 0.99, window 5000 bp, minimum number of positive probes 5, and discard 0%. Candidate regions were classified by MAT score 30-300, 300-3000, and >3000.

Partek ANOVA tools were used to perform paired t-tests with multiple testing correction using all samples as replicates of the test condition and co-hybridized xhh DNA replicates as the control condition. Comparisons were performed at the accession level using AccAvg(Cy3) vs. AccAvg(Cy5) and at the individual probe level using Cy3 vs. Cy5 intensity values. Significance thresholds were set at a stepup false discovery rate <0.05 and fold-difference >2. An outlier analysis was also performed at accession and probe levels by calculating the standard deviation of AccSig or probe signal, and filtering for any values that were two or more standard deviations higher than the population mean.

Example 2

Microarray Design

Figure 2B:
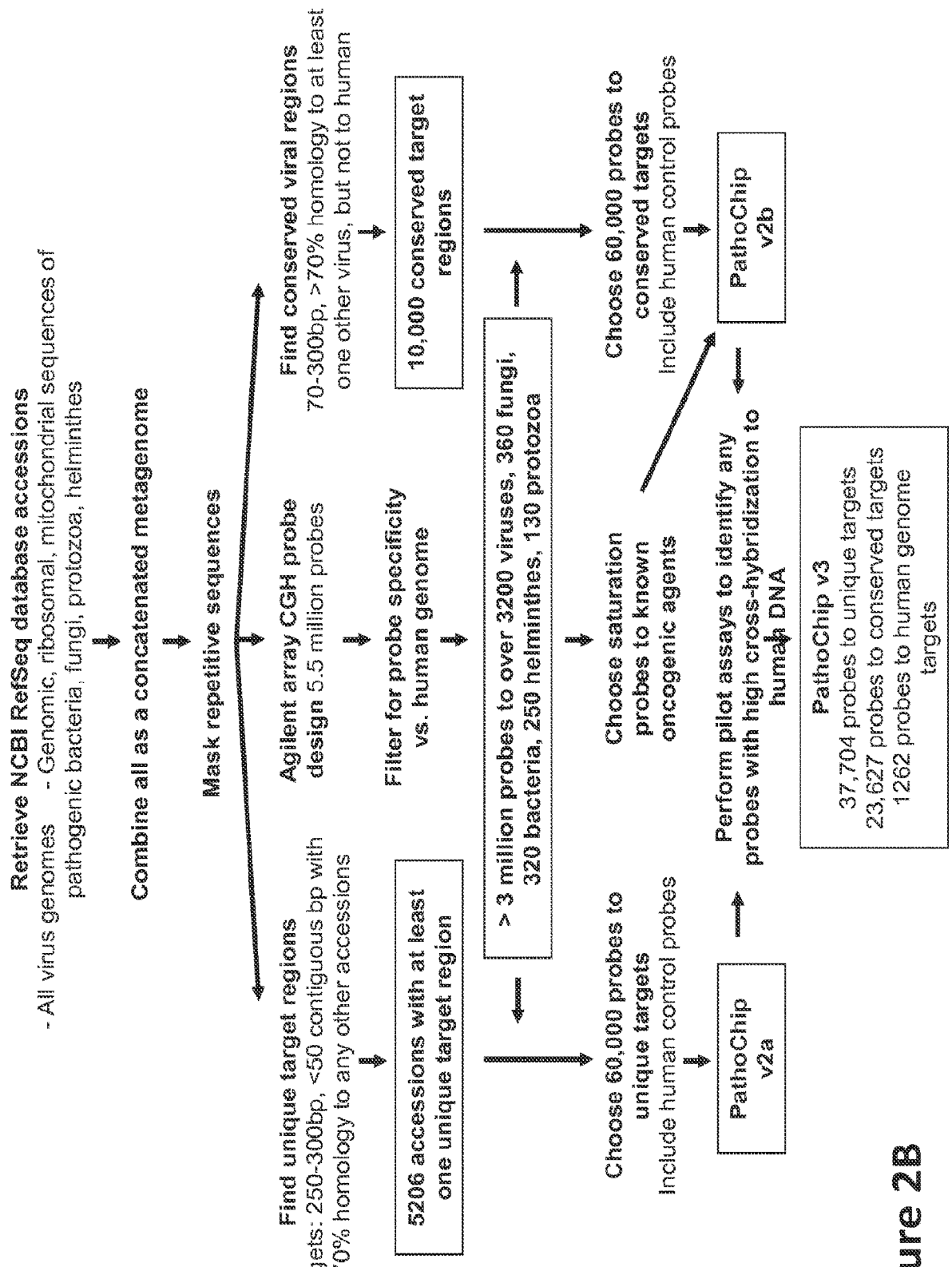
Figure 3A:
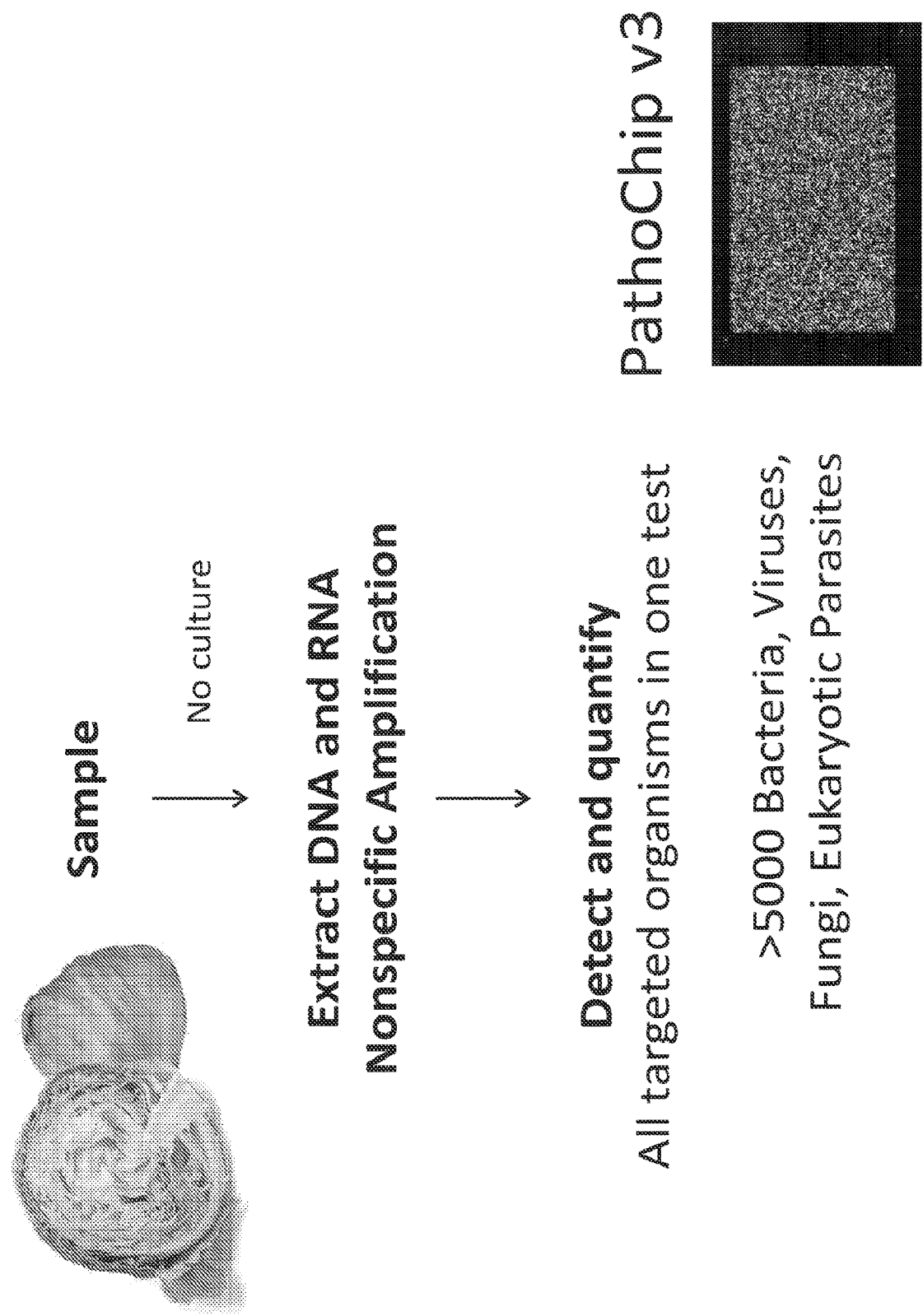
FIGS. 3A and 3B, depict a sample screening workflow using the PathoChip.
Figure 3B:
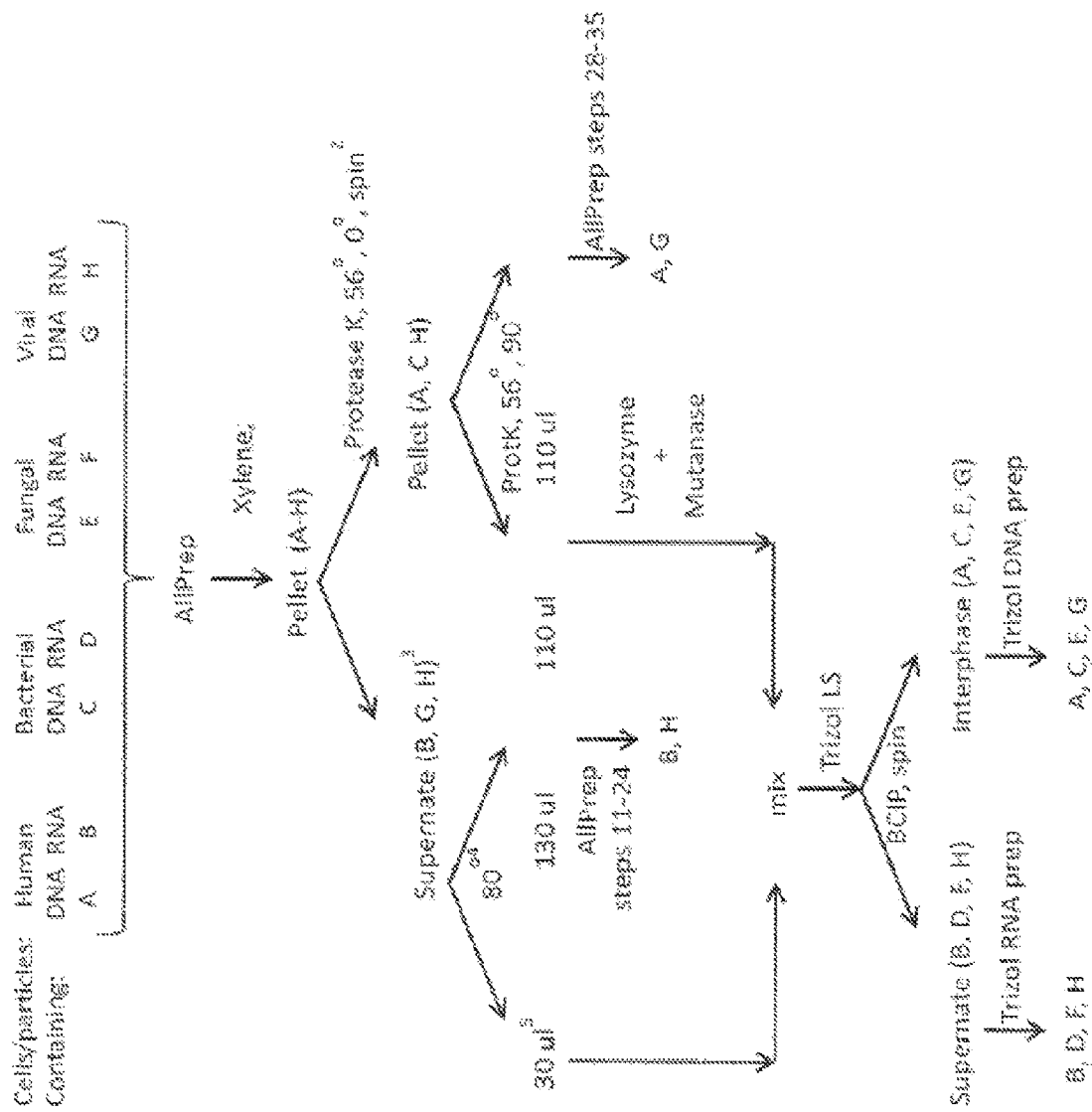
Figure 5A:
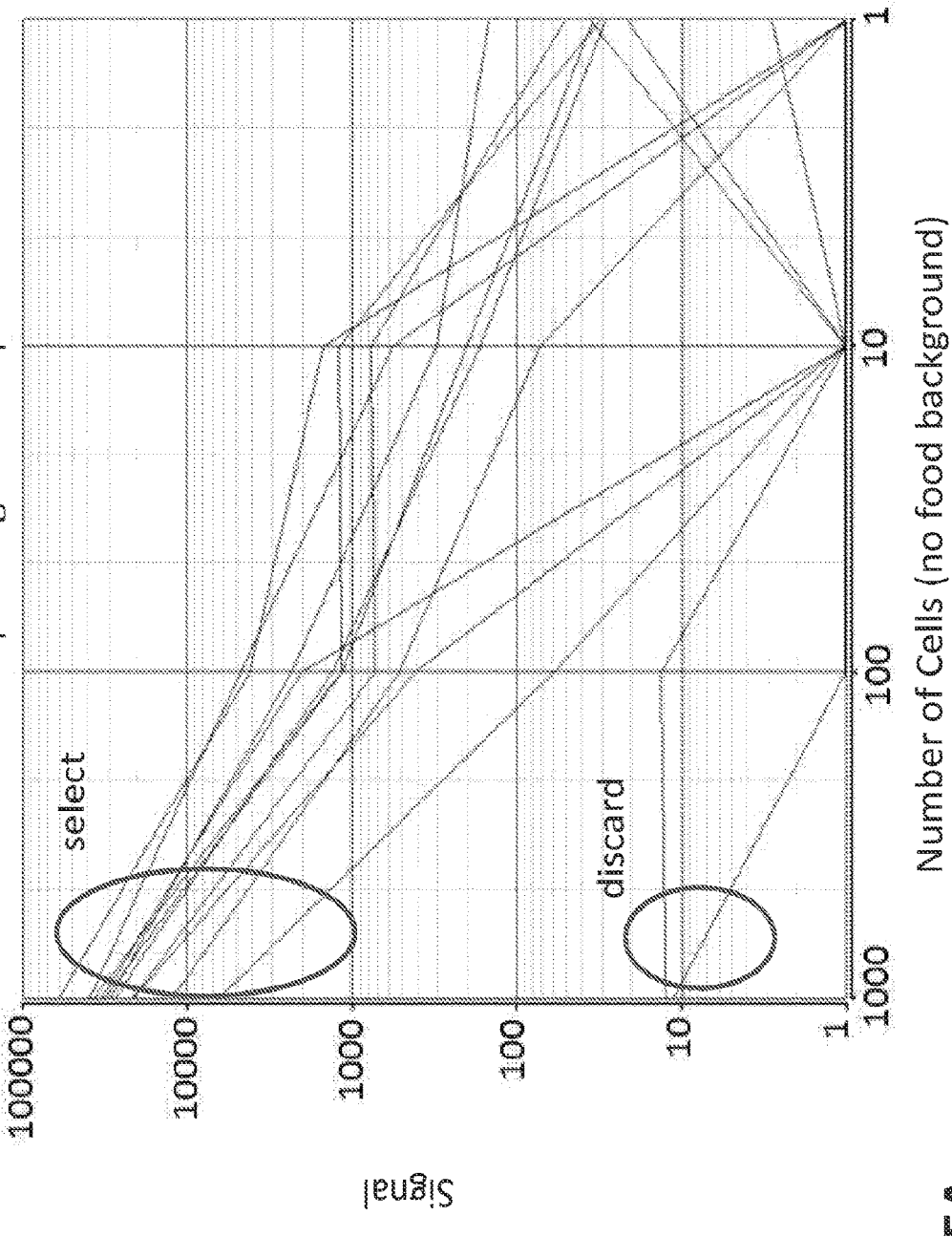
Figure 5B:
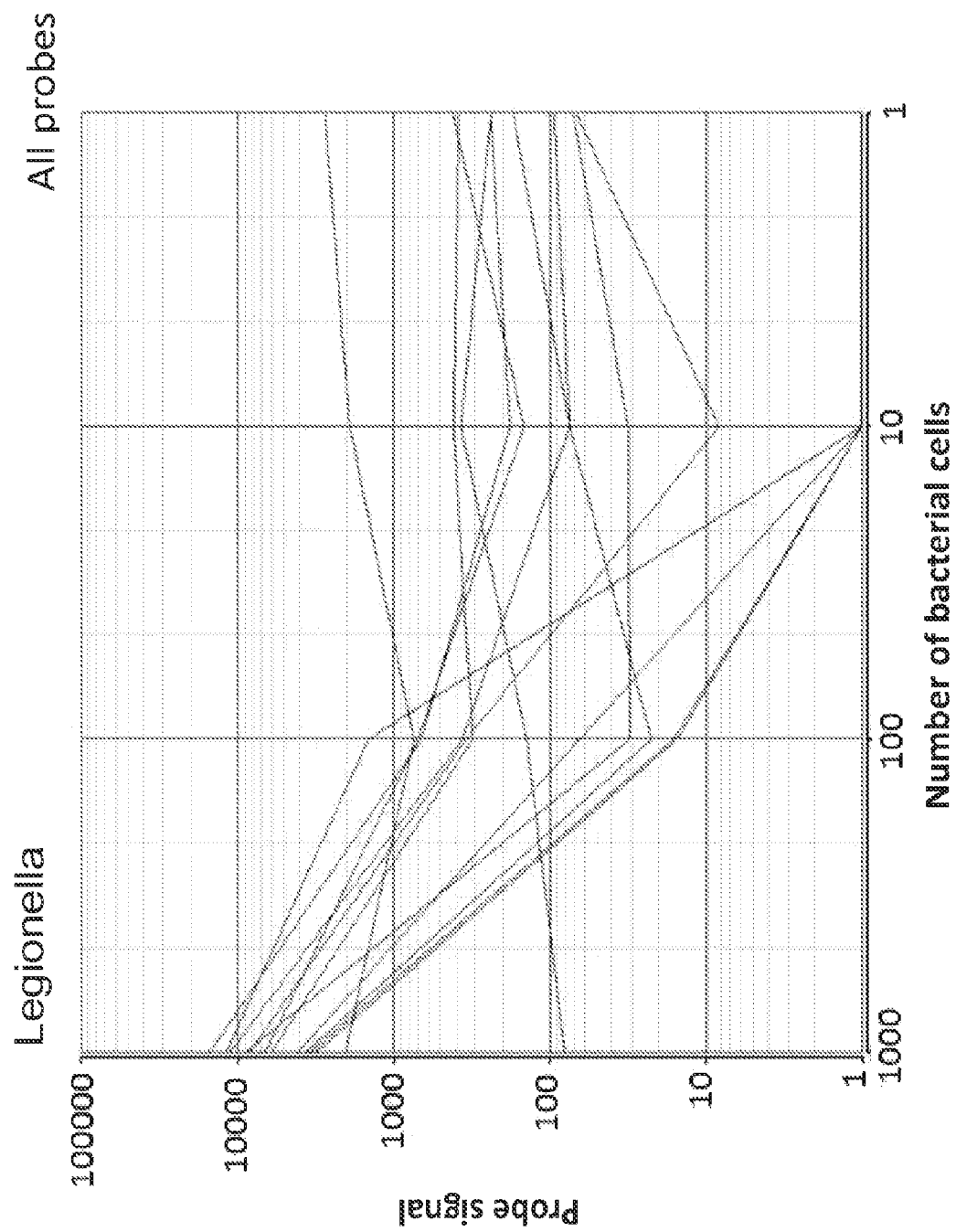
Figure 5C:
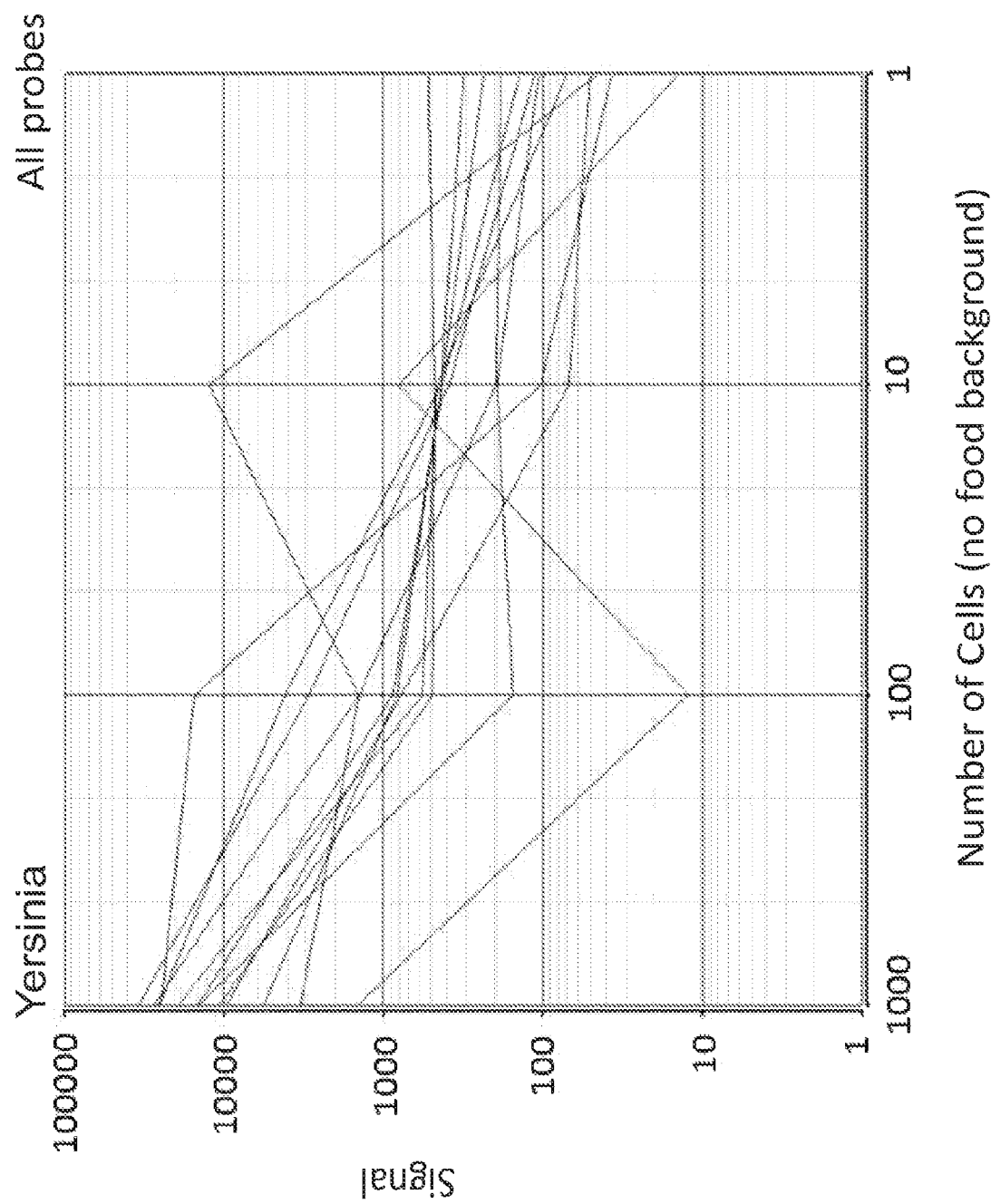
Figure 5F:
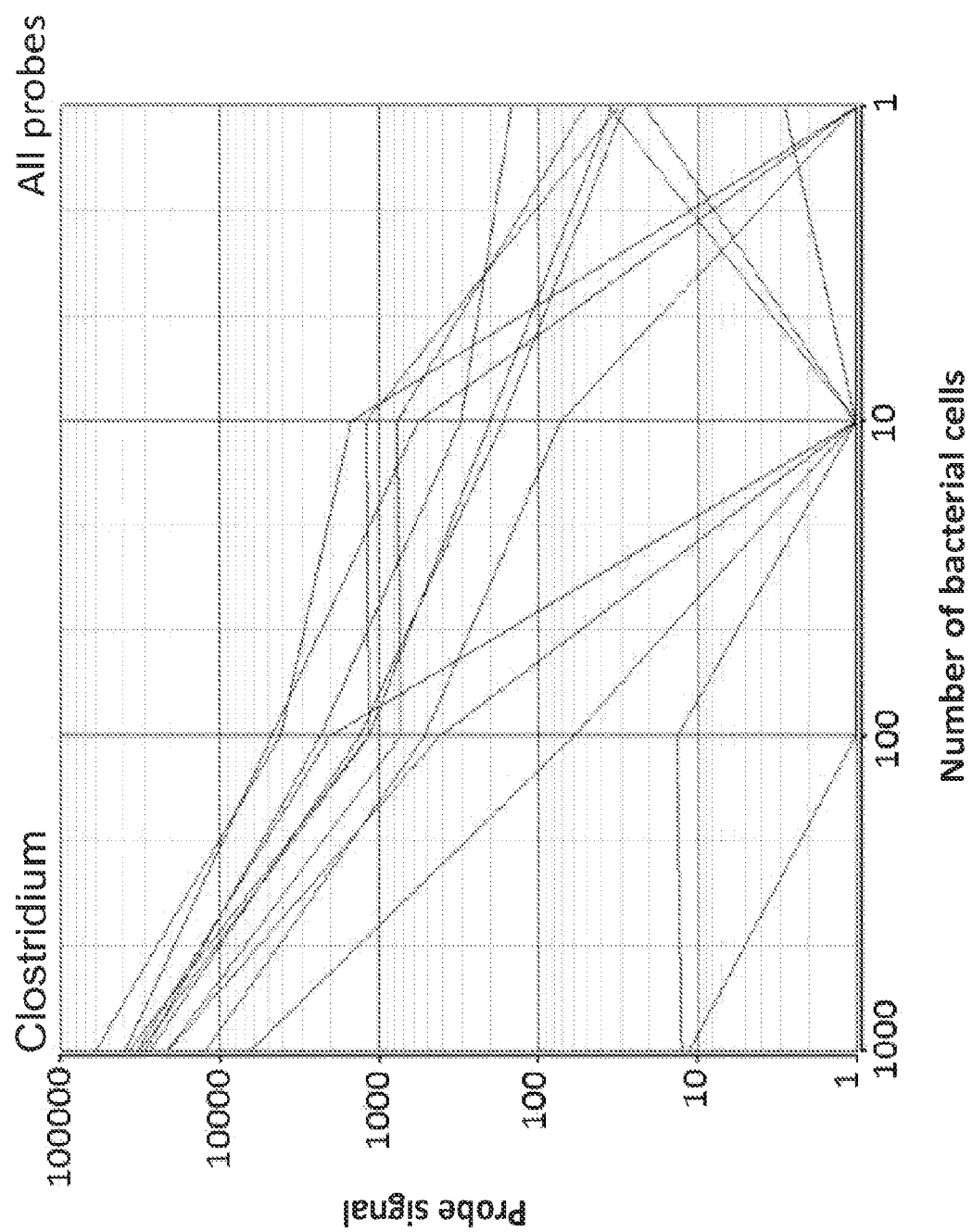
Figure 5G:
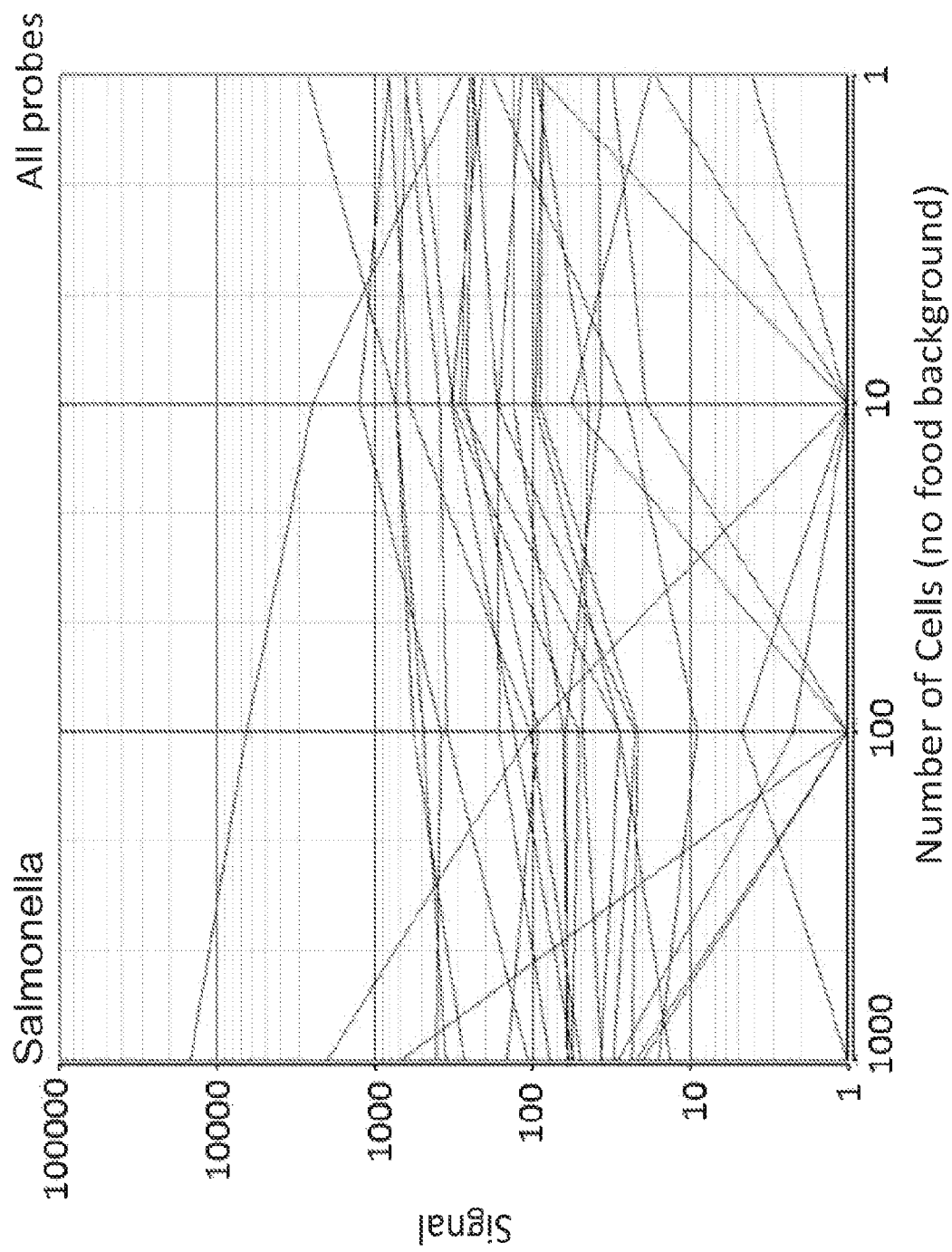
Figure 5H:
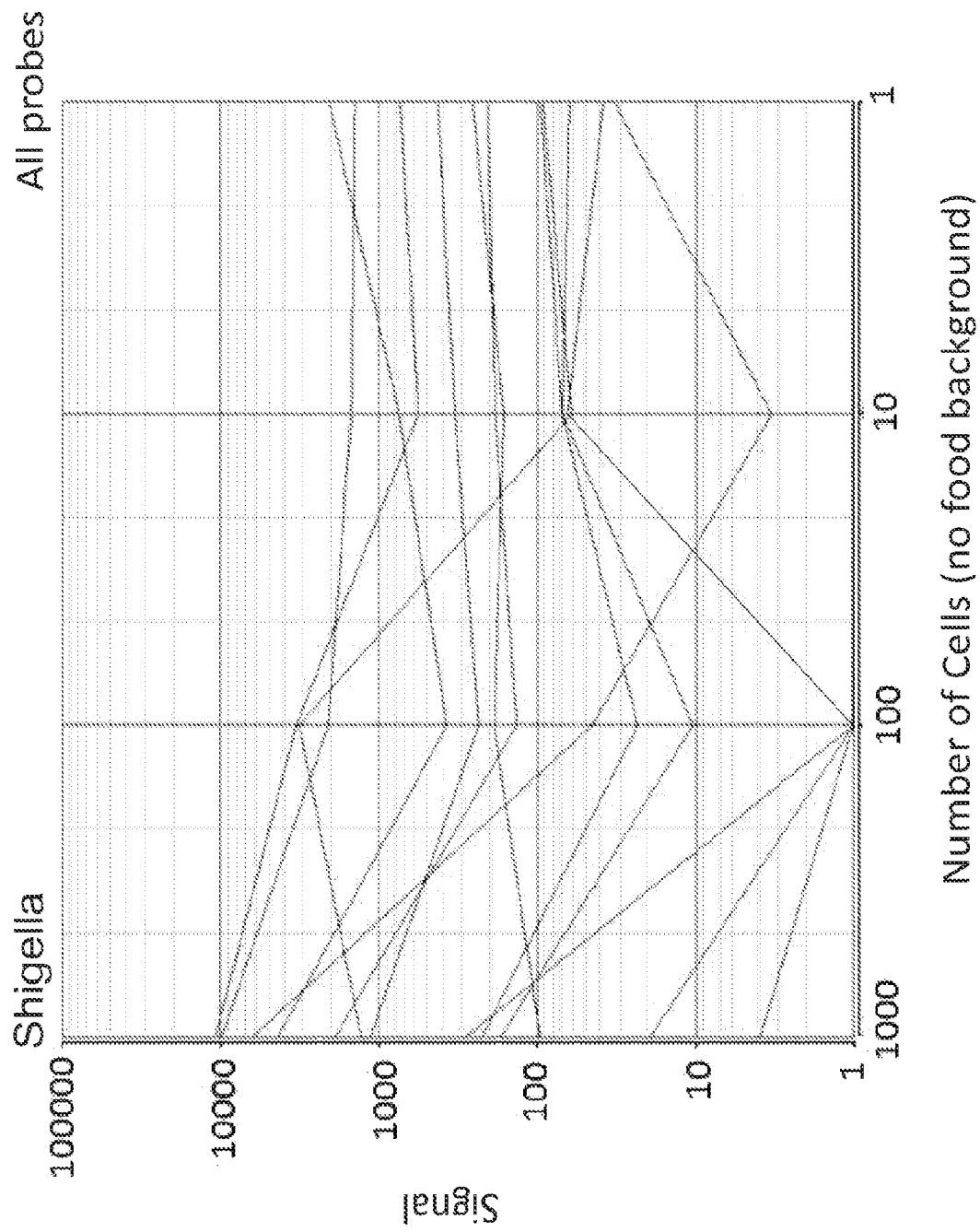
Figure 5I:
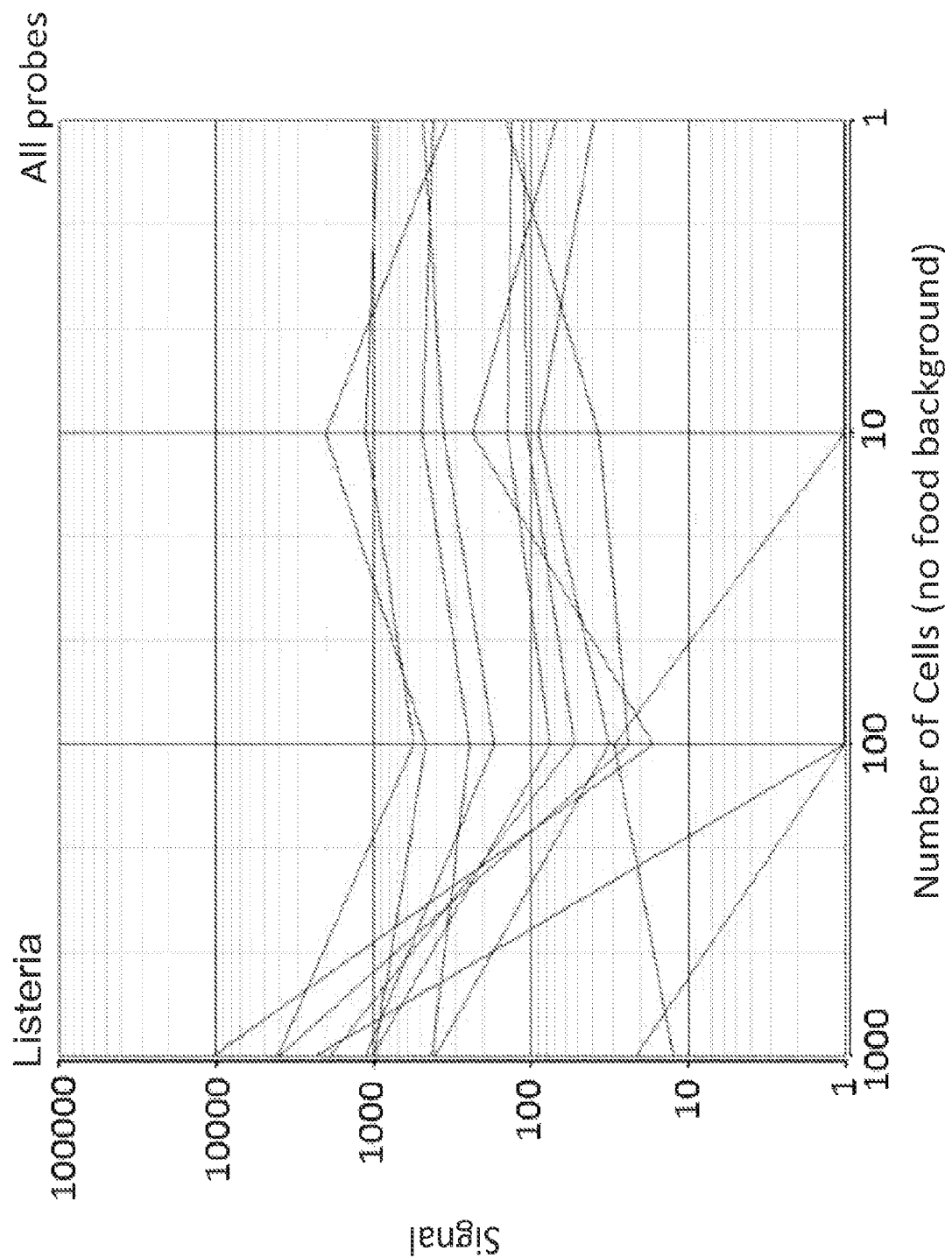
Figure 6A:
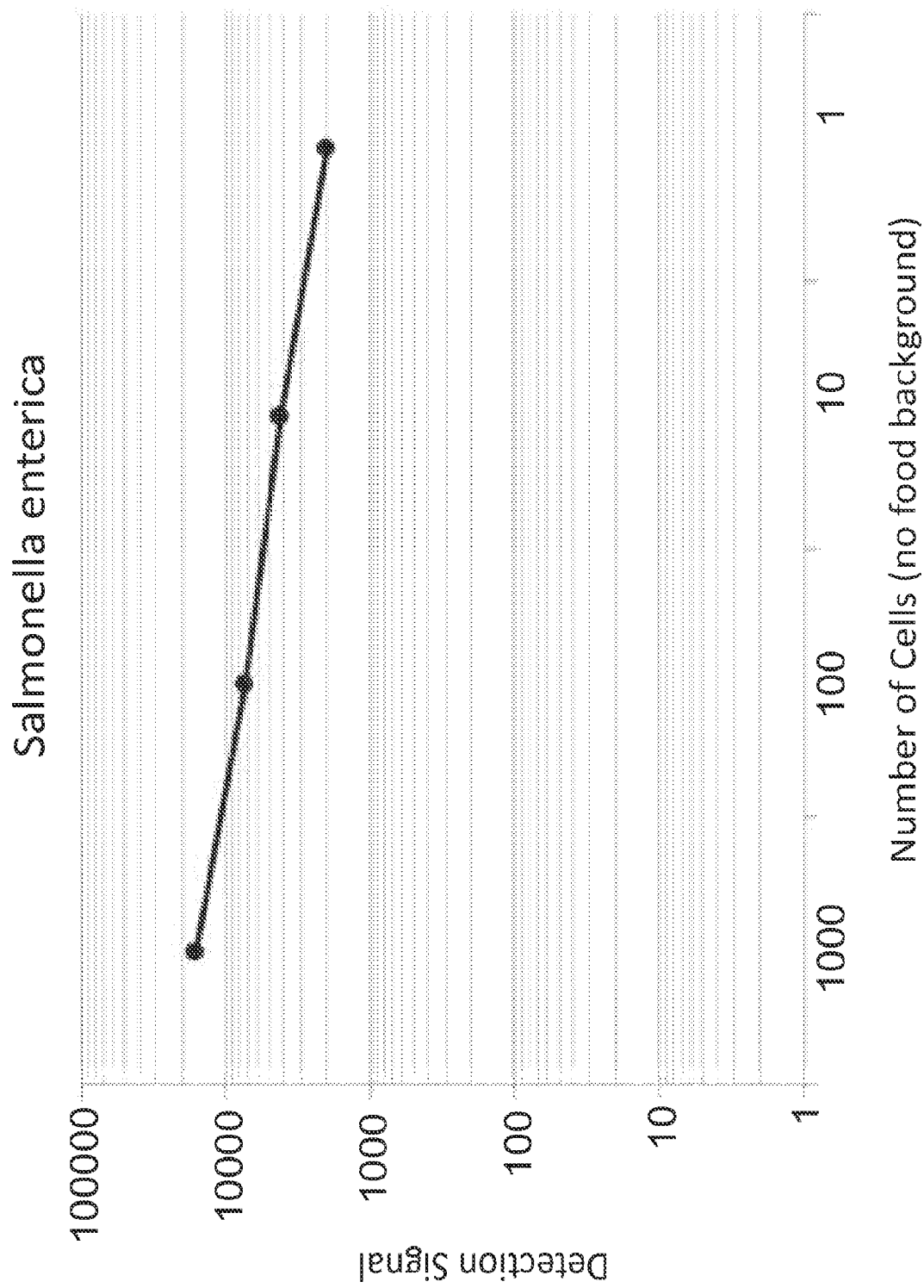
FIGS. 6A through FIG. 6H, show that selected probes were summed to report a single detection signal.
Figure 6B:
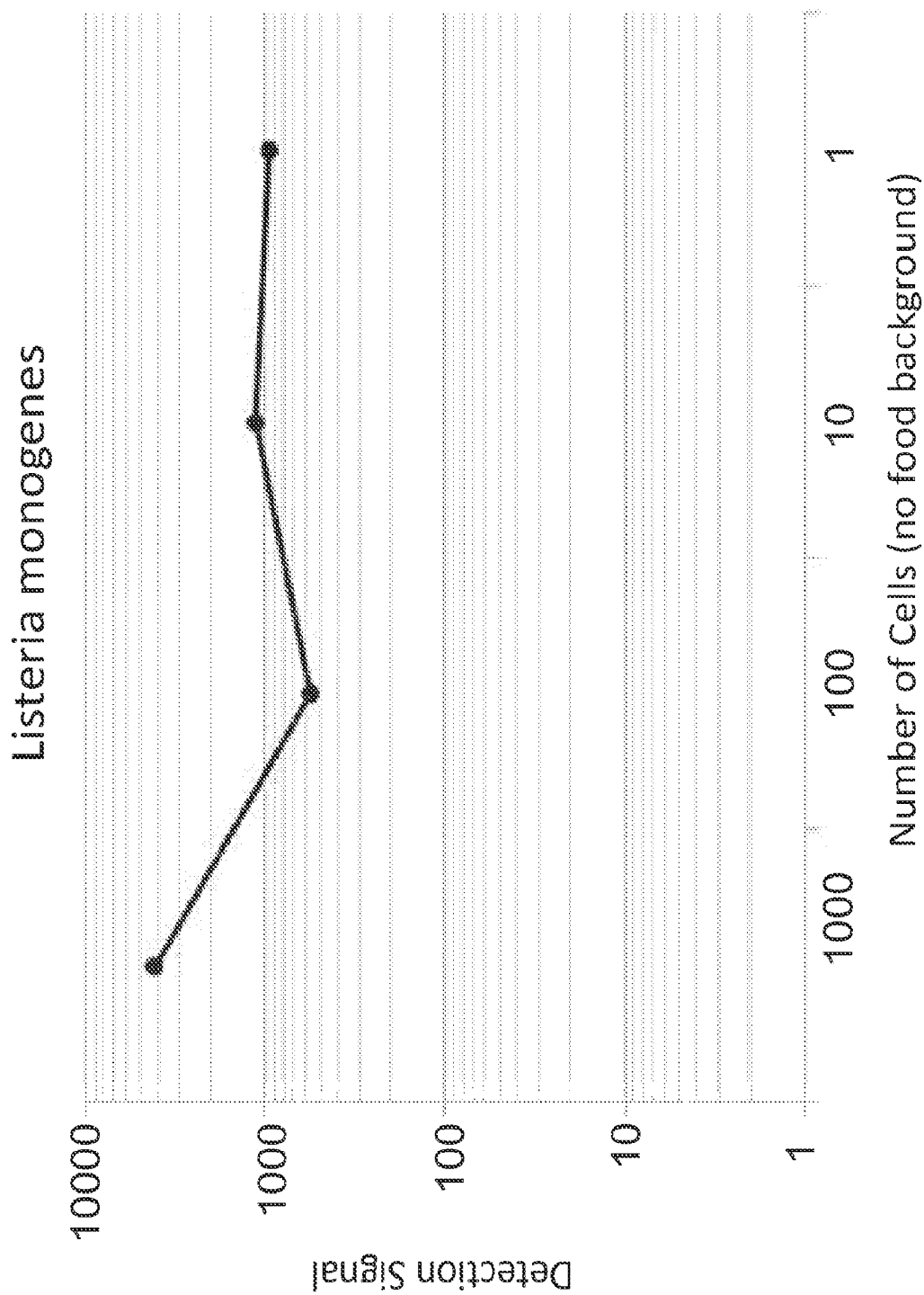
Figure 6C:
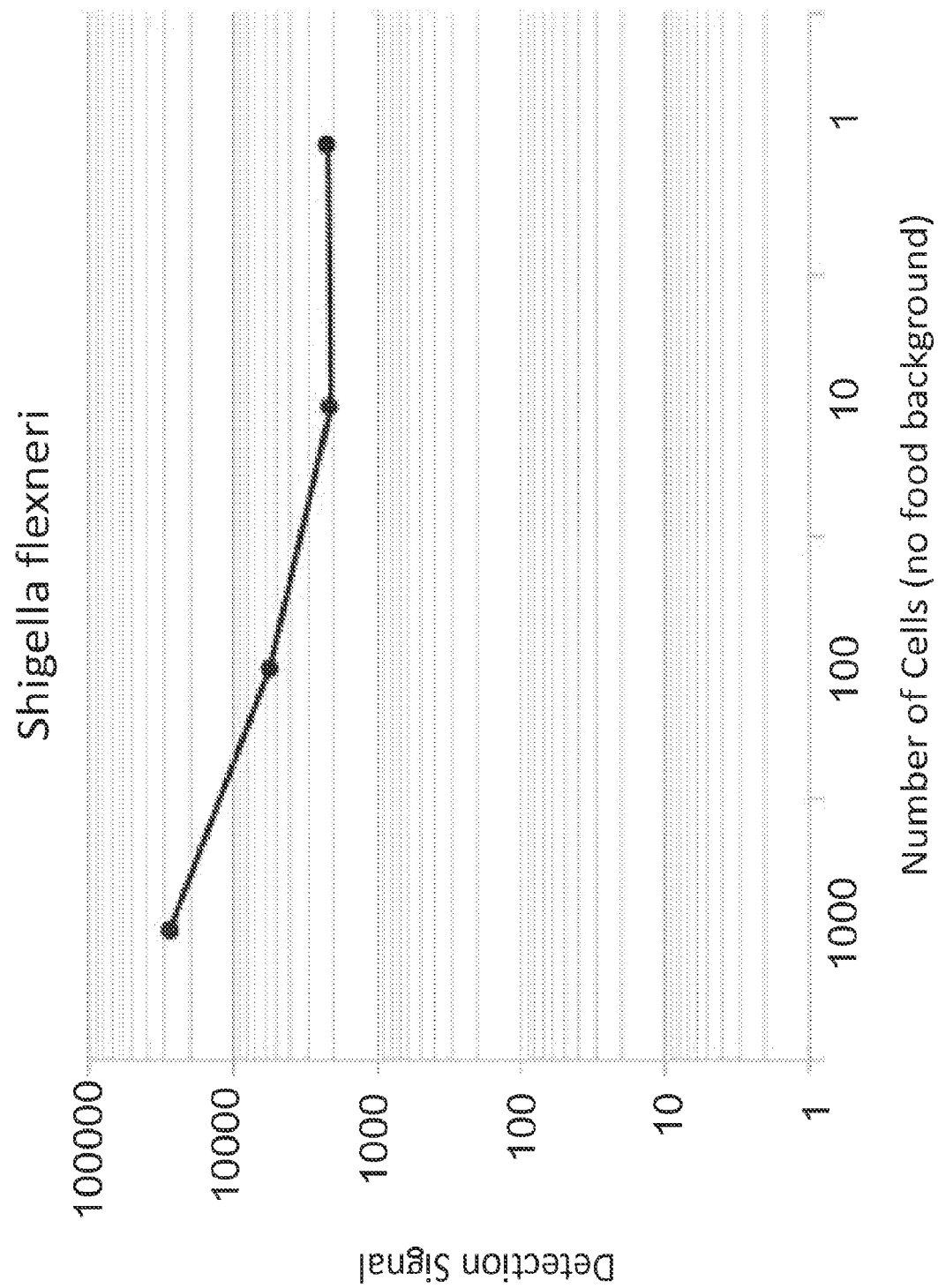
Figure 6D:
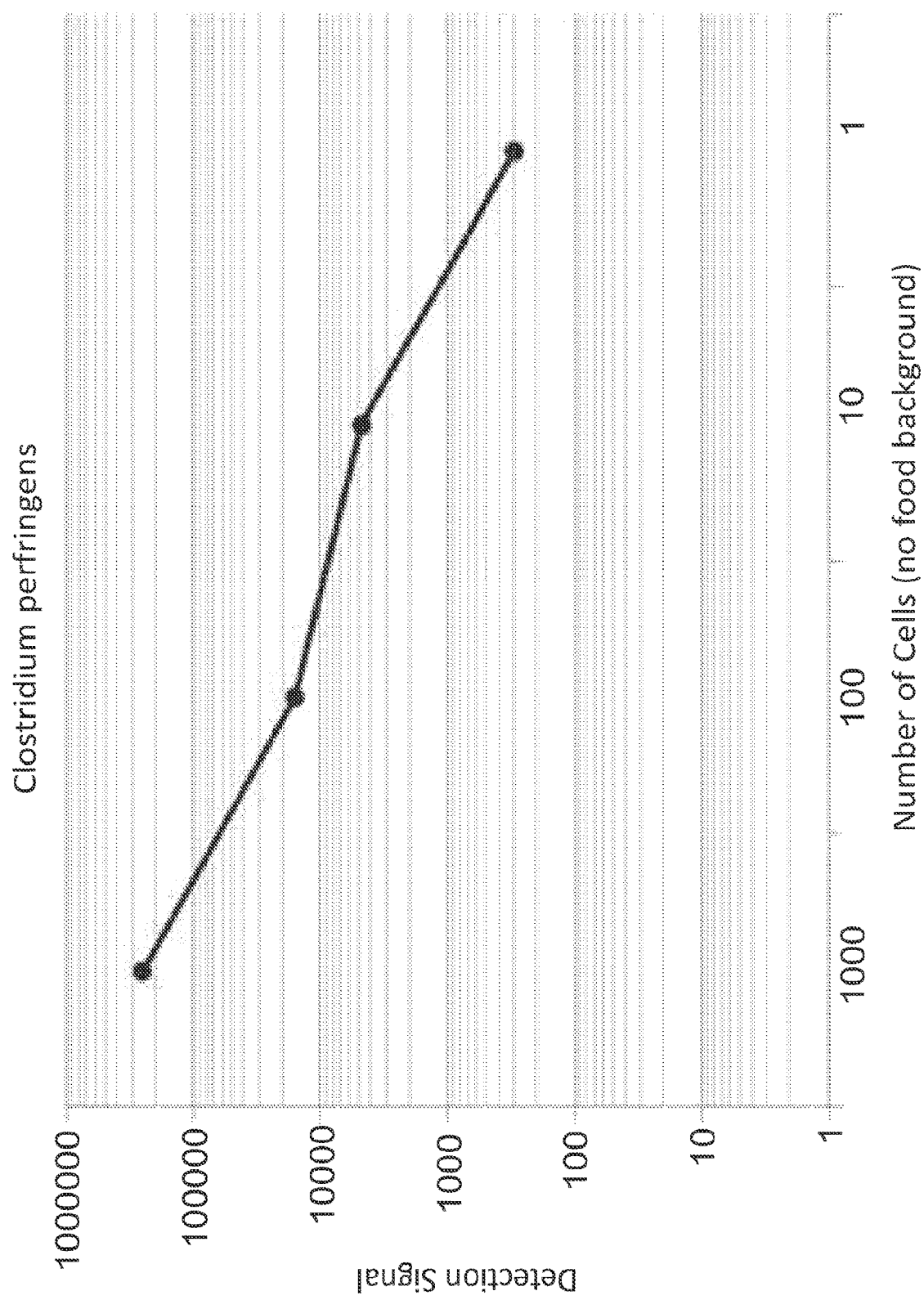
Figure 6E:
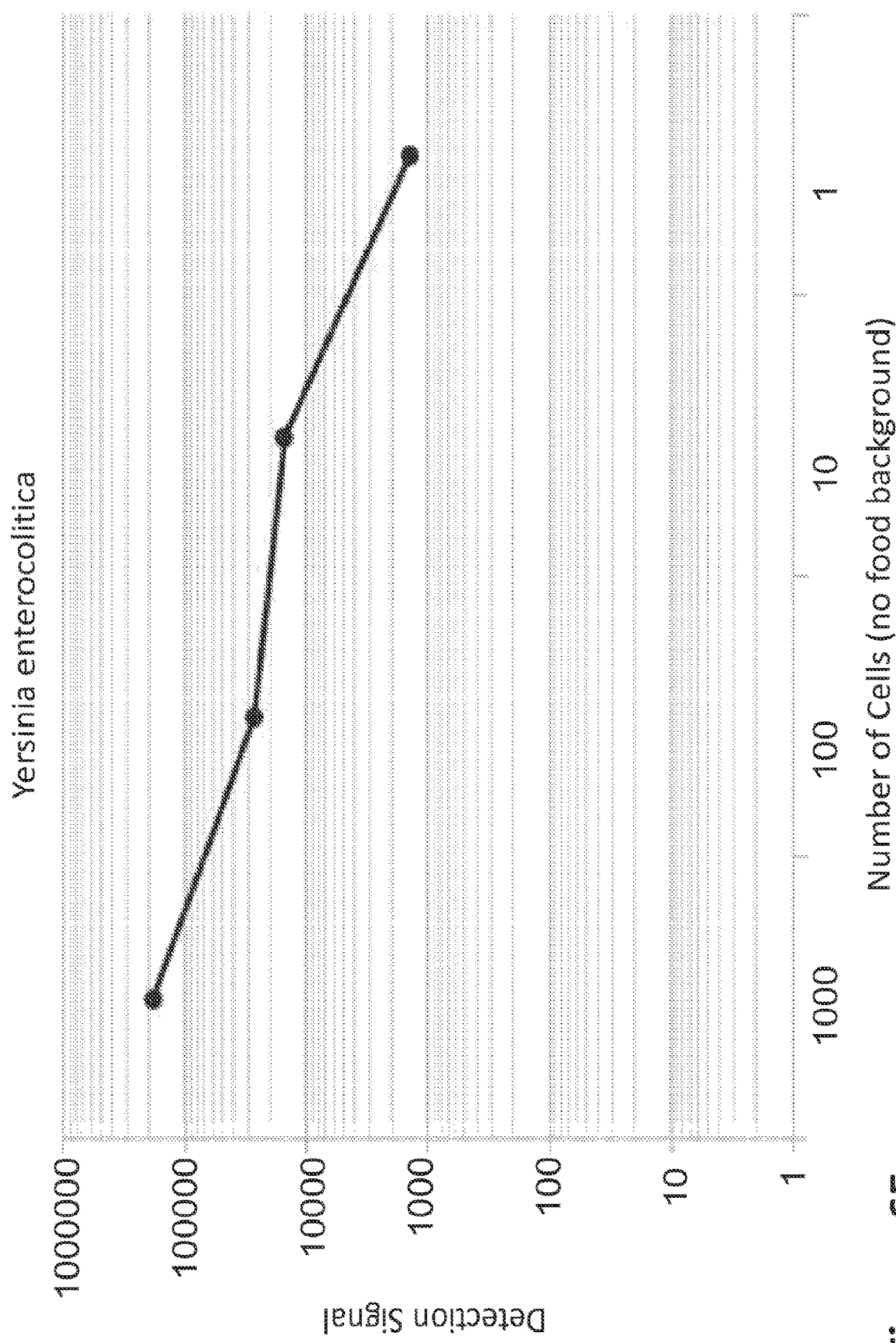
Figure 6F:
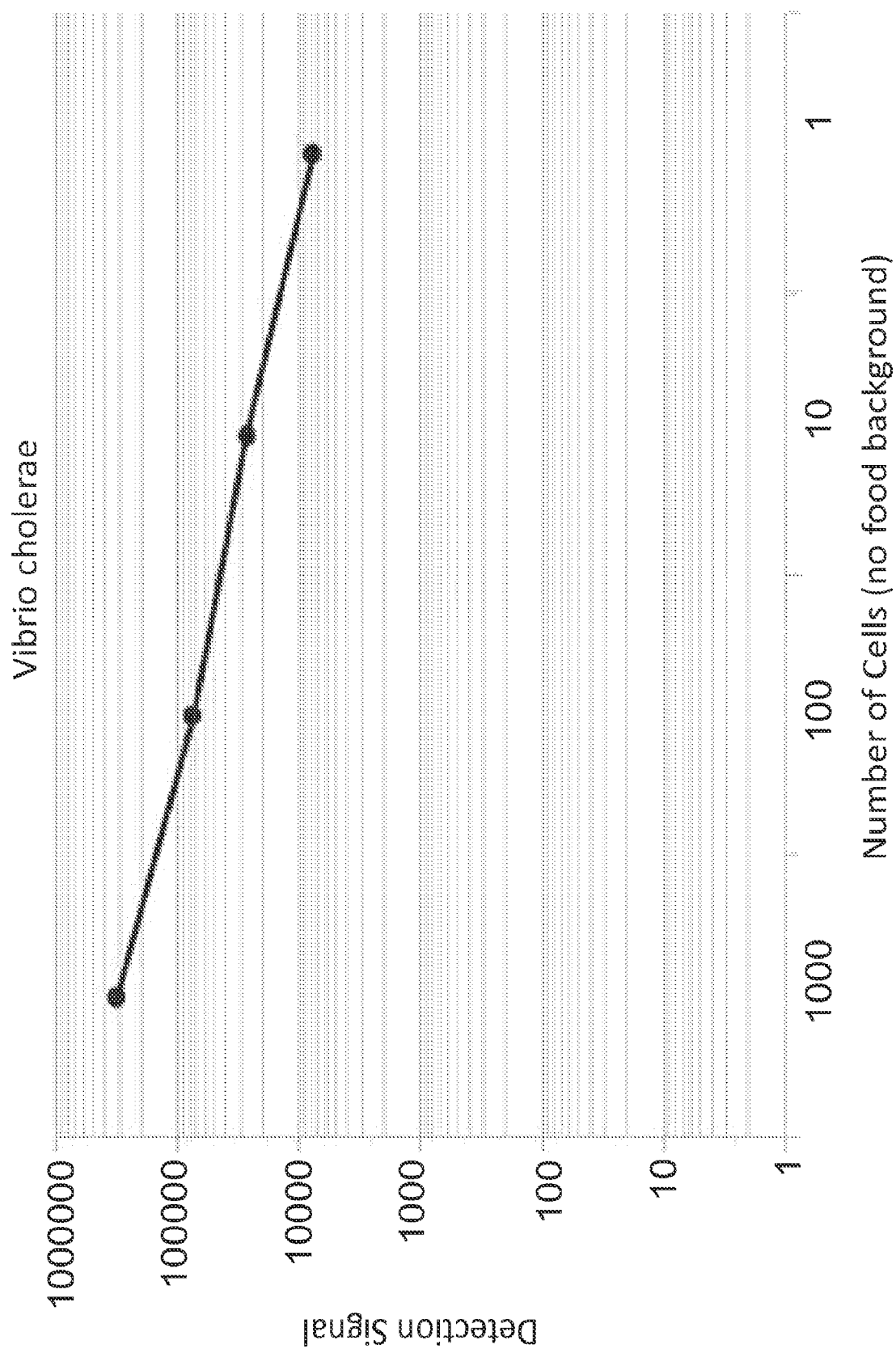
Figure 6G:
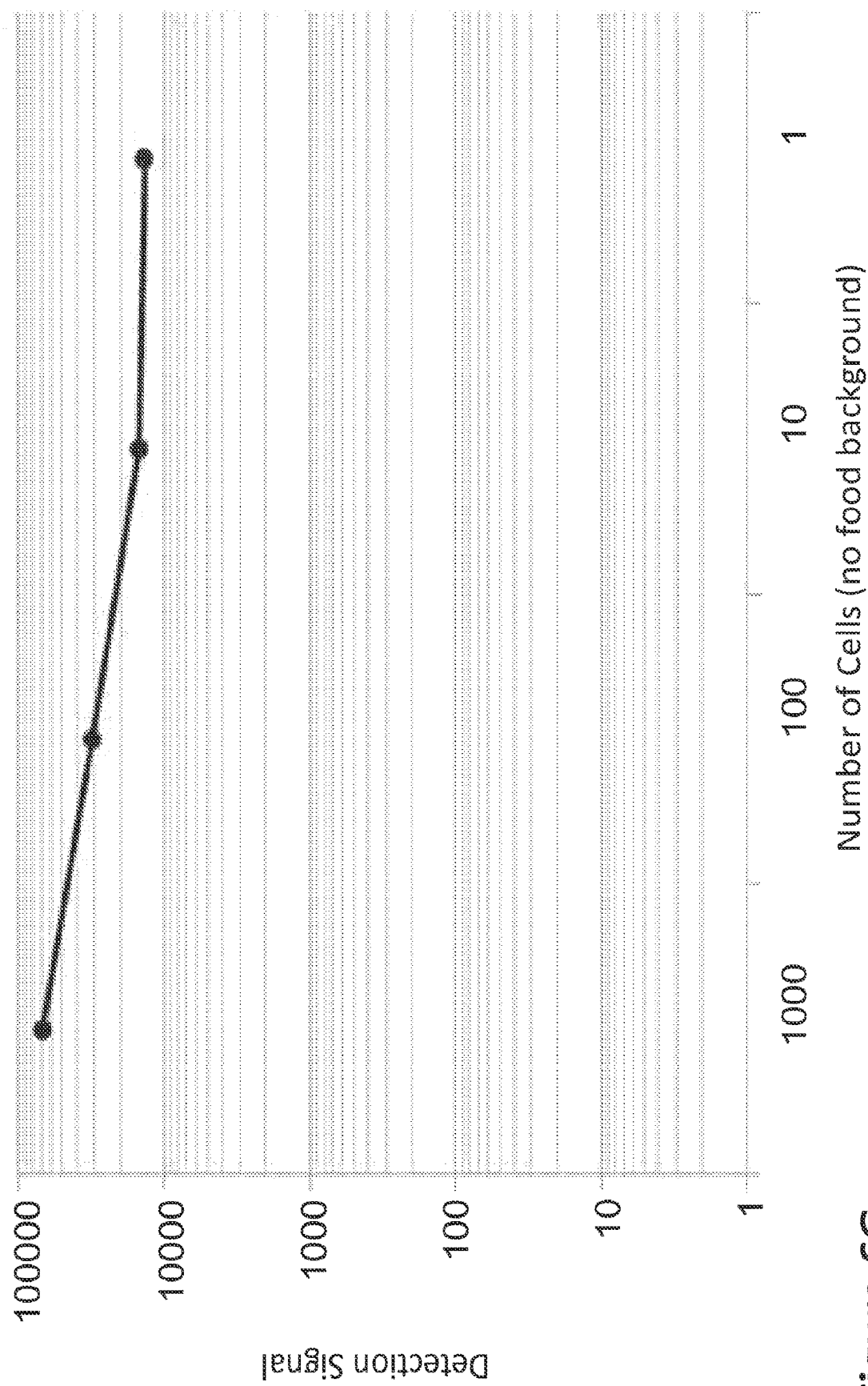
Figure 6H:
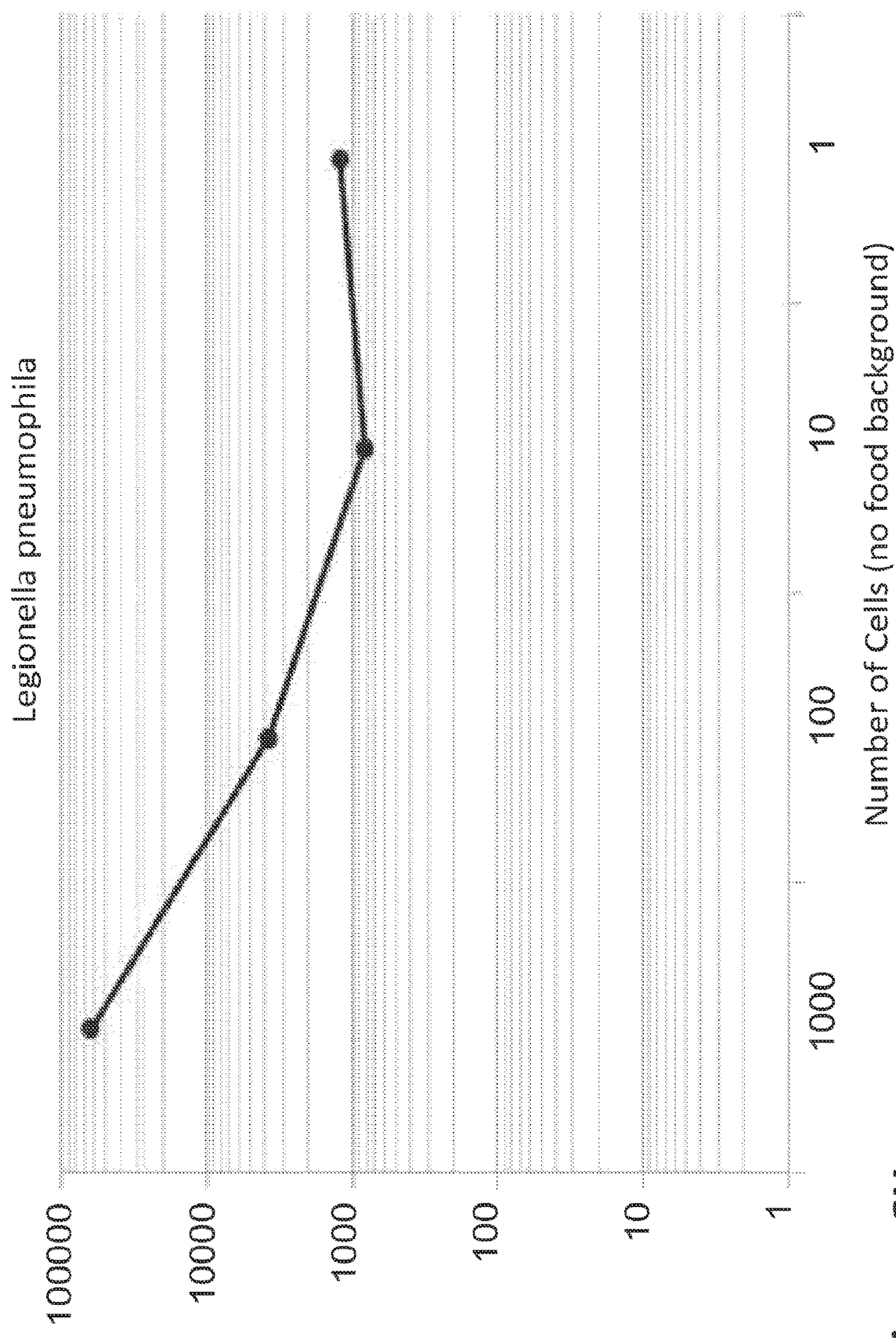

The PathoChip design goals were to cover all public NCBI viral genomes, and sequences from selected microorganisms that are pathogenic to humans, using multiple probes to independent target sites in each species' genome (FIG. 2A). The resulting collection of sequences was assembled into a metagenome of 448.9 million by containing 5206 accessions for over 4200 viruses, bacteria and eukaryotes. Agilent custom probe design algorithms built for comparative genomic hybridization applications were used to identify 5.5 million probes in the metagenome, over 3 million of which are predicted to have low risk of cross-hybridization with a human genome sequence. A subset of these probes that map to unique target regions were synthesized on PathoChip v2a microarrays, and a separate set that covers regions of sequence conservation between at least two viruses was synthesized on PathoChip v2b arrays (FIG. 2B). PathoChip v2b also included 2085 probes tiled throughout the lengths of 22 accessions for known cancer-associated organisms.

Pilot assays using Agilent reference human DNA showed median probe intensities of over 750 fluorescence units for probes to human sequences, and around 17 fluorescence units for non-human specific probes on PathoChip v2a and 120 fluorescence units for non-human conserved probes on PathoChip v2b (Table 1). These assays identified 6360 probes with fluorescence >150 that apparently hybridize to human DNA and were therefore removed from consideration for the PathoChip v3 design (FIG. 2B).

flexneri, and *Listeria monocytogenes*, were grown in pure cultures, and 2 million cells of each target organism were pooled into one stock. Aliquots of diluted stock containing 1000, 100, 10 or 1 cell of each target were used for DNA+RNA extraction, amplification, and hybridization to PathoChip v3. All probes for each target were analyzed to identify probe subsets with high sensitivity for *Legionella pneumophila, Yersinia enterocolitica, Escherichia coli, Vibrio cholerae, Clostridium perfringens, Salmonella enterica, Shigella flexneri*, and *Listeria monocytogenes* (FIGS. 5A-5I). The selected probes were summed to report a single detection signal for each of *Salmonella enterica, Listeria monocytogenes, Shigella flexneri, Clostridium perfringens, Yersinia enterocolitica, Vibrio cholerae, Escherichia coli* O157:H7, and *Legionella pneumophila* (FIGS. 6A-6H). These results indicate that the PathoChip is able to detect the presence of various target organisms with high sensitivity.

Example 4

Assay Testing in the Presence of Human and Plant Background DNA+RNA

Figure 7:
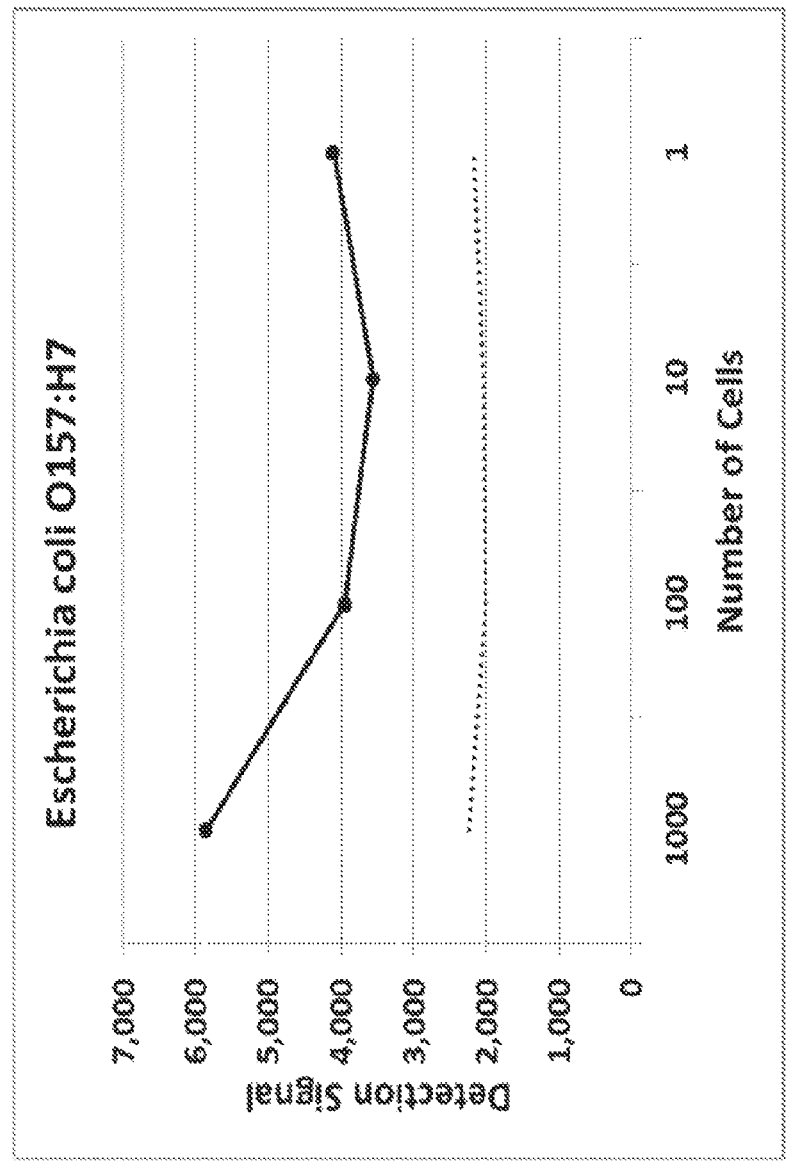
FIG. 7, comprising
Figure 7:
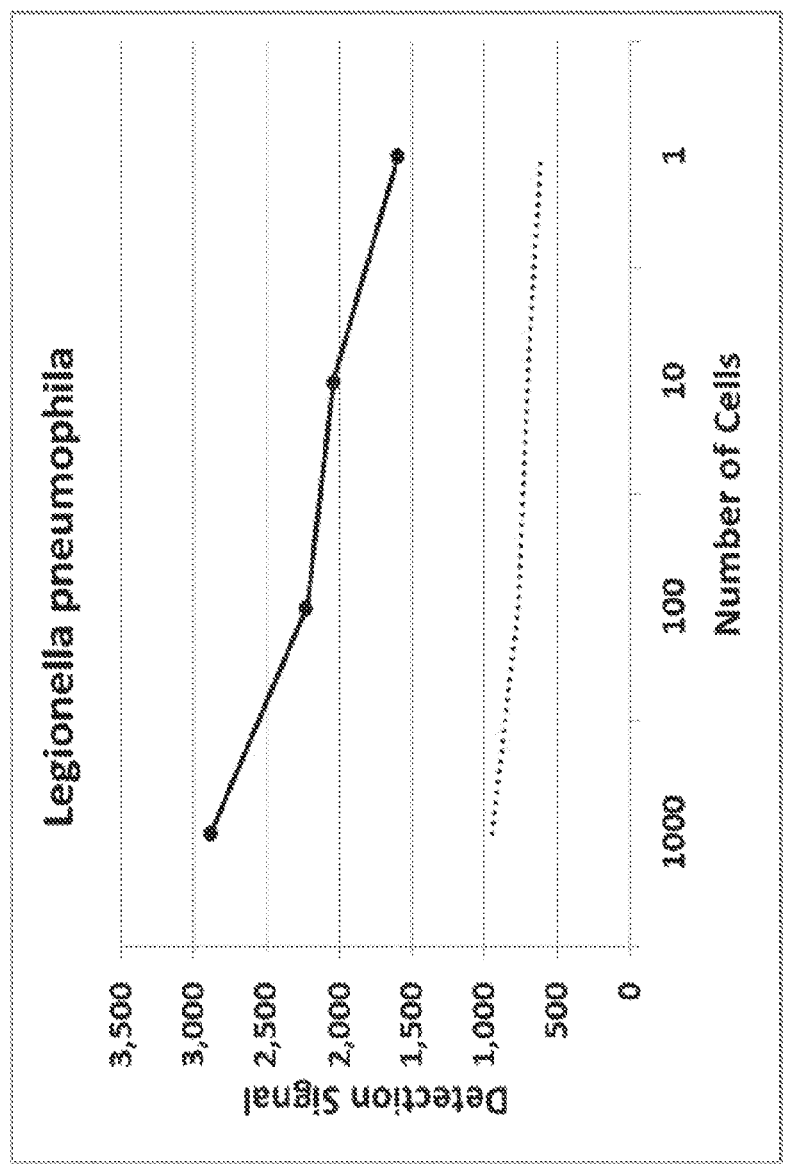
Figure 7:
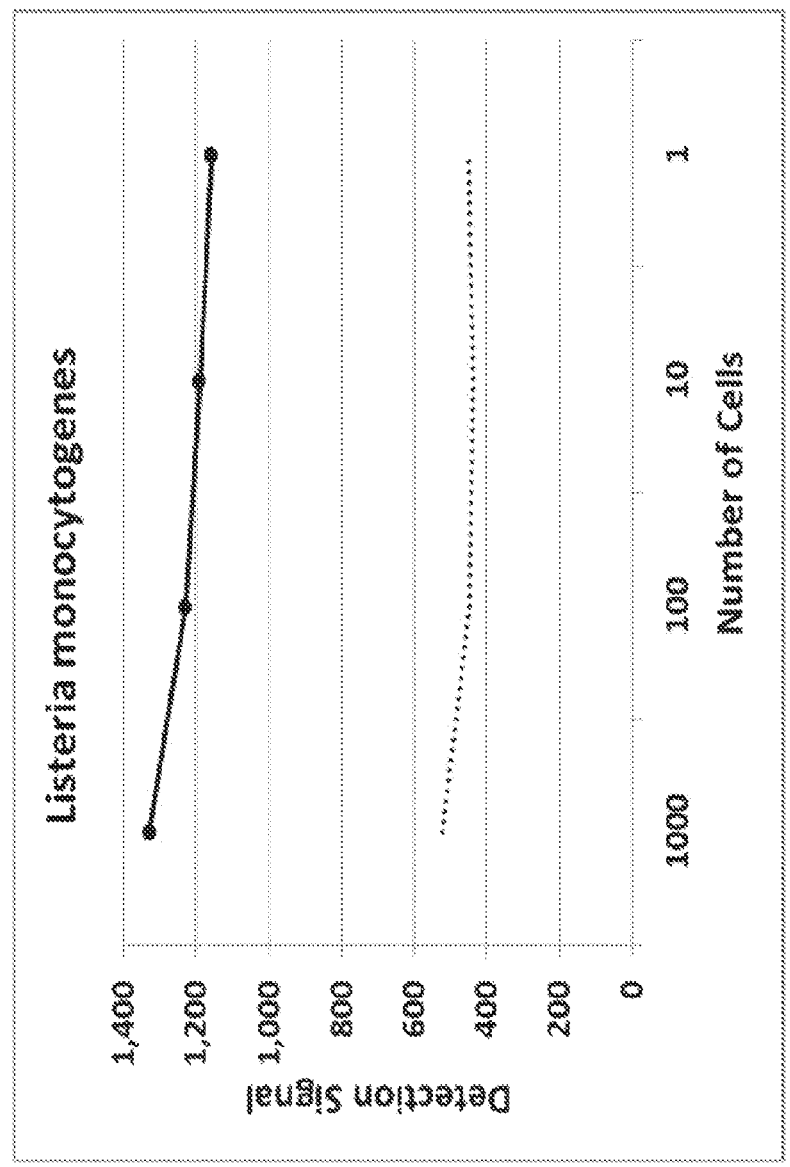
Figure 7:
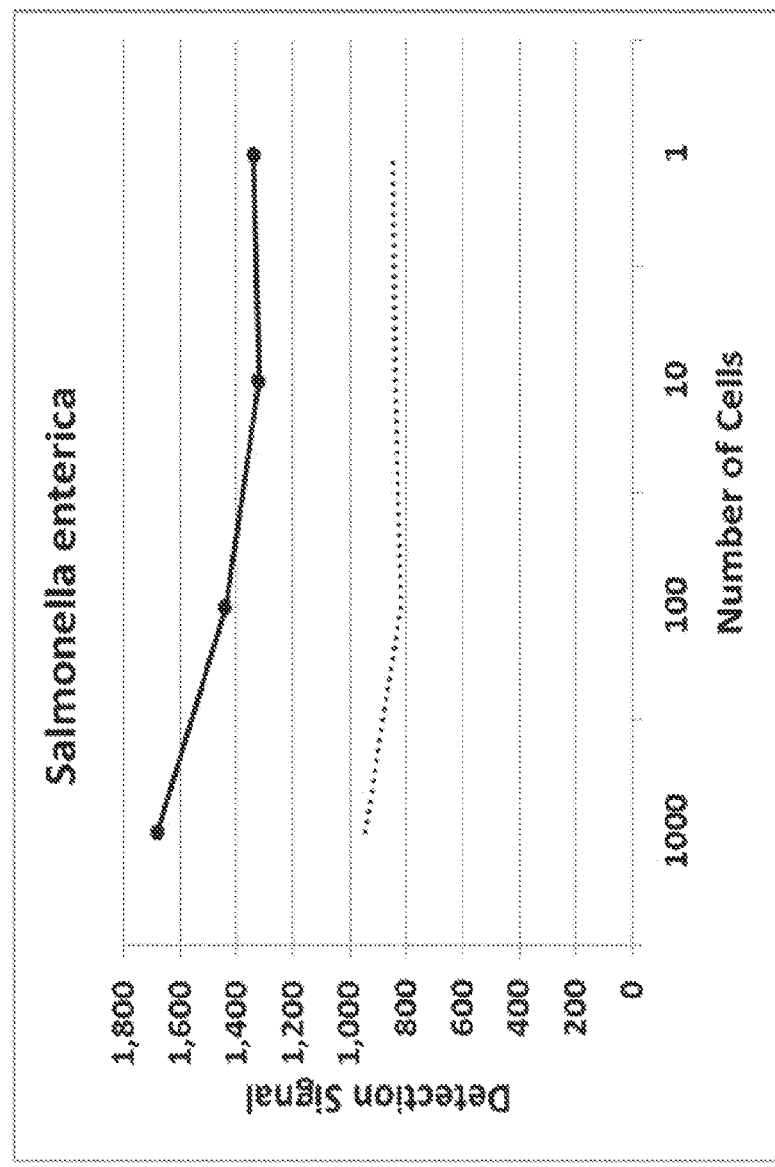
Figure 7:
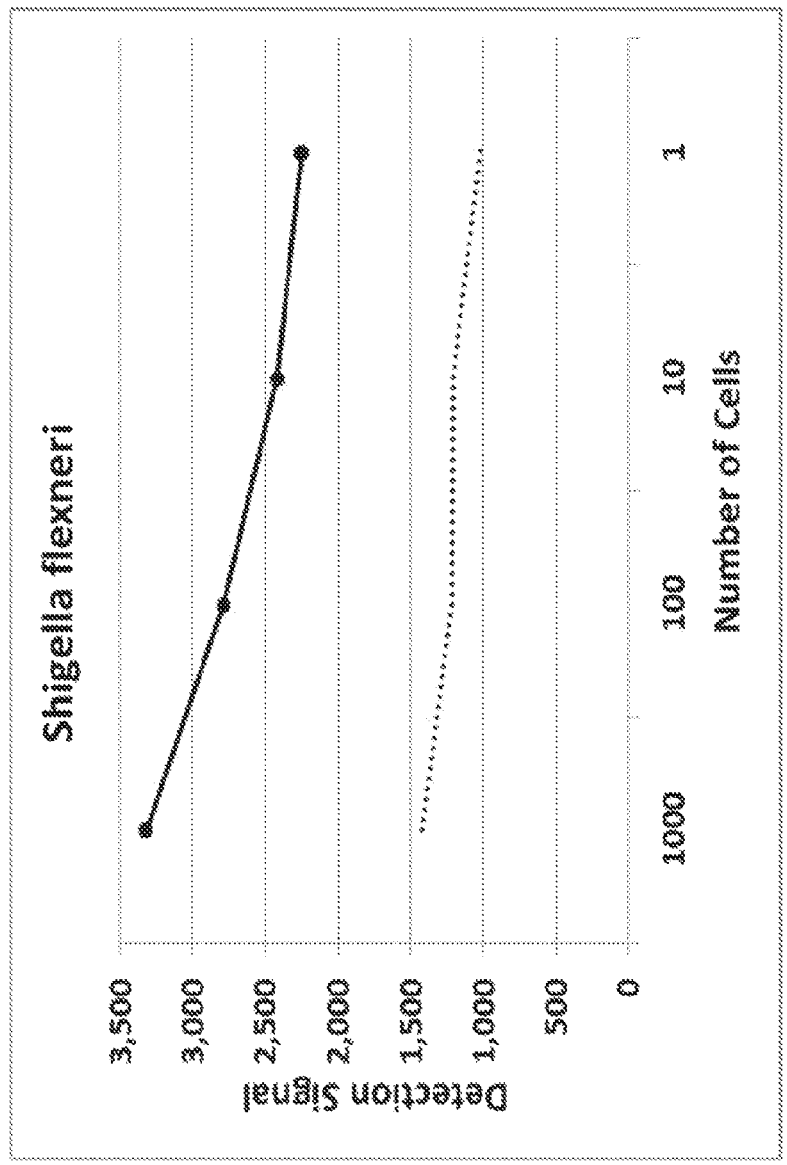
Figure 7:
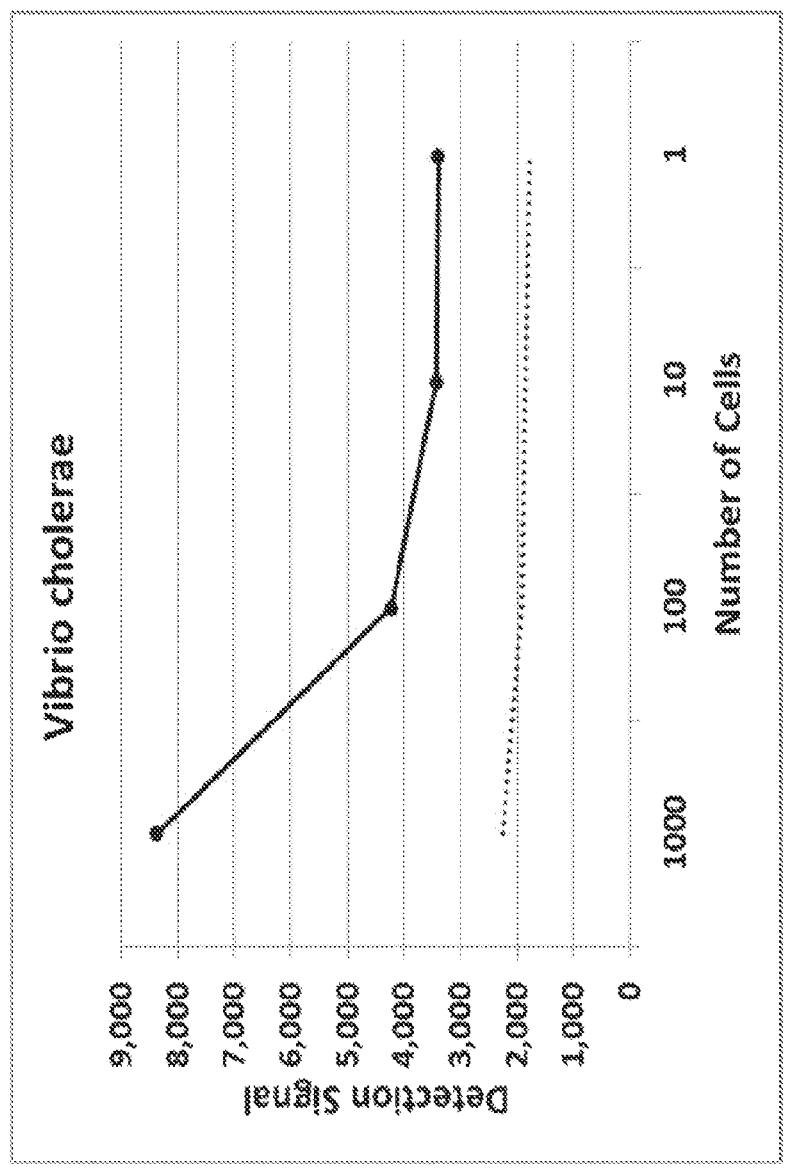
Figure 7:
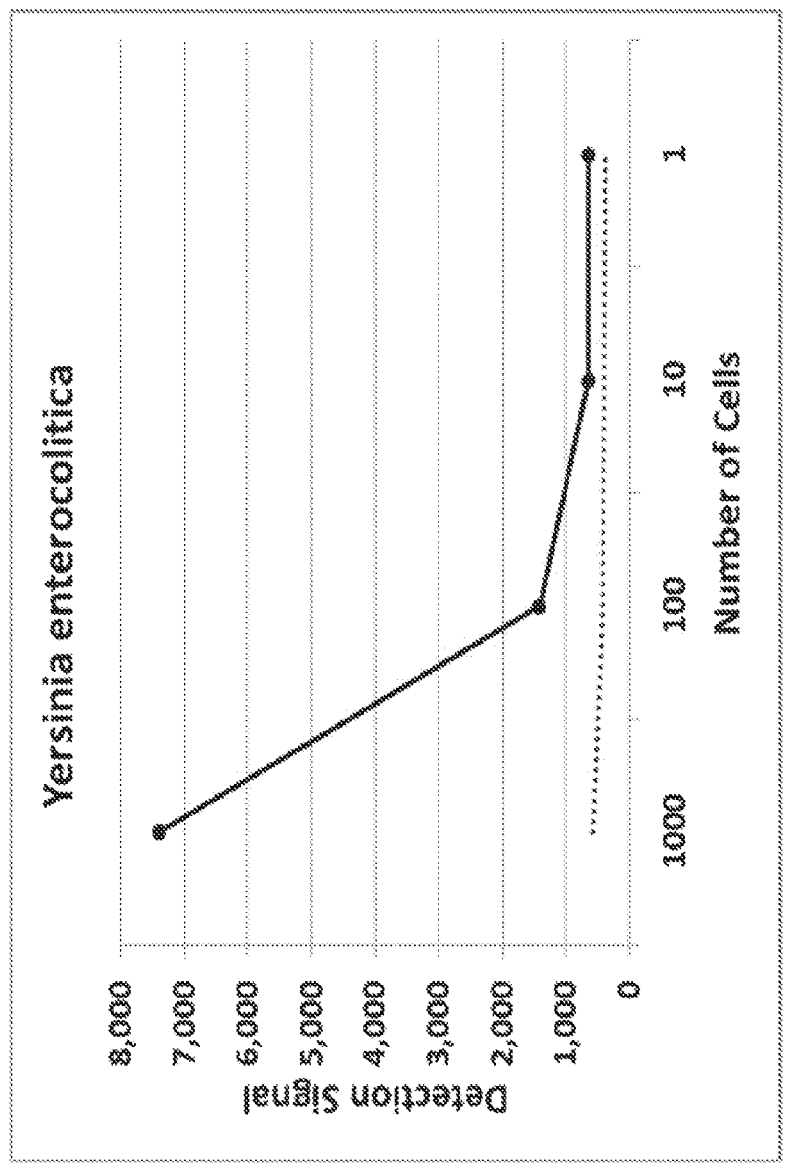
Figure 8:
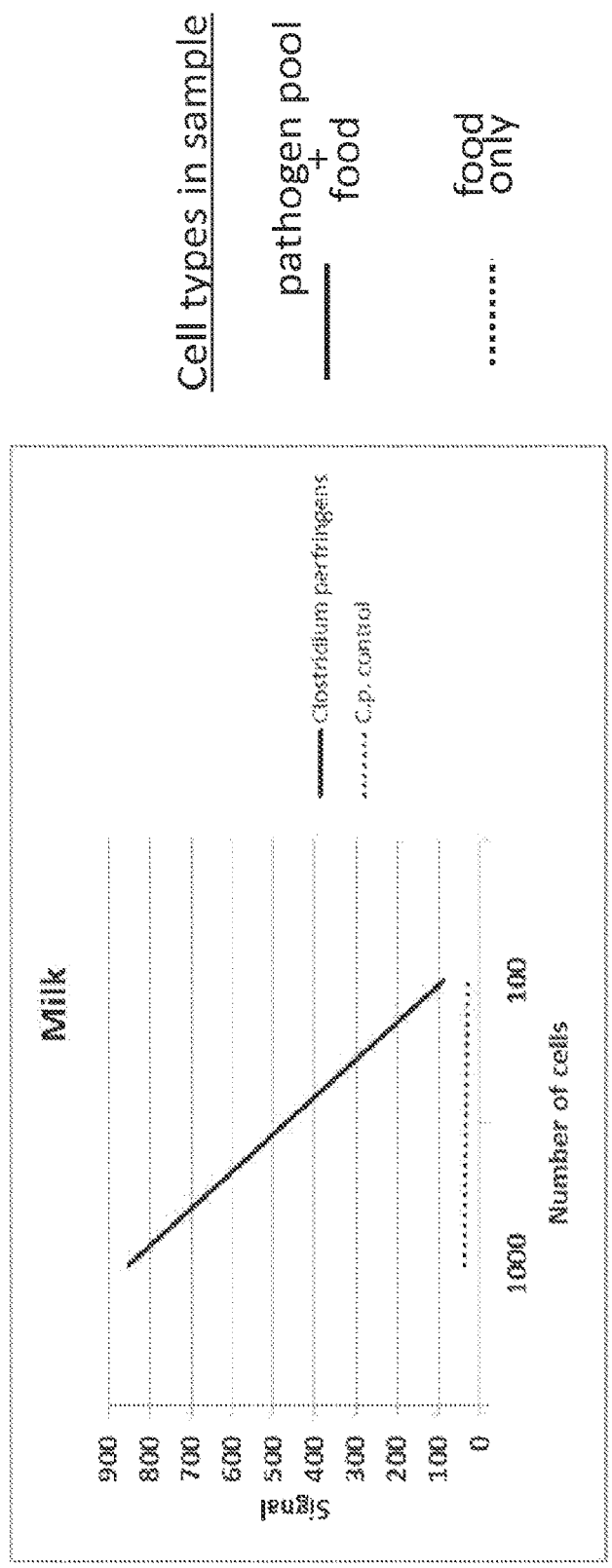
FIG. 8, comprising
Figure 8:
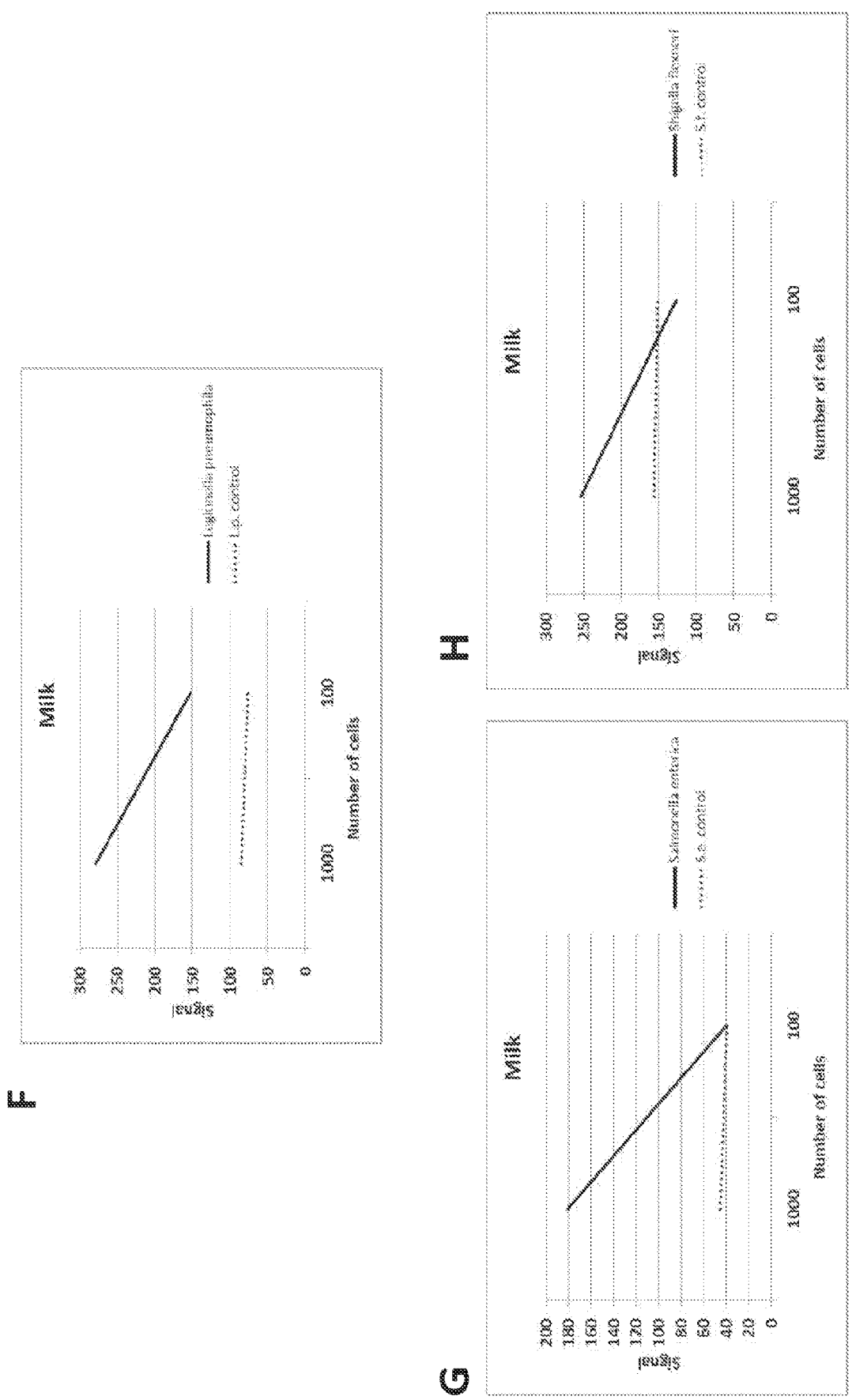
Figure 10:
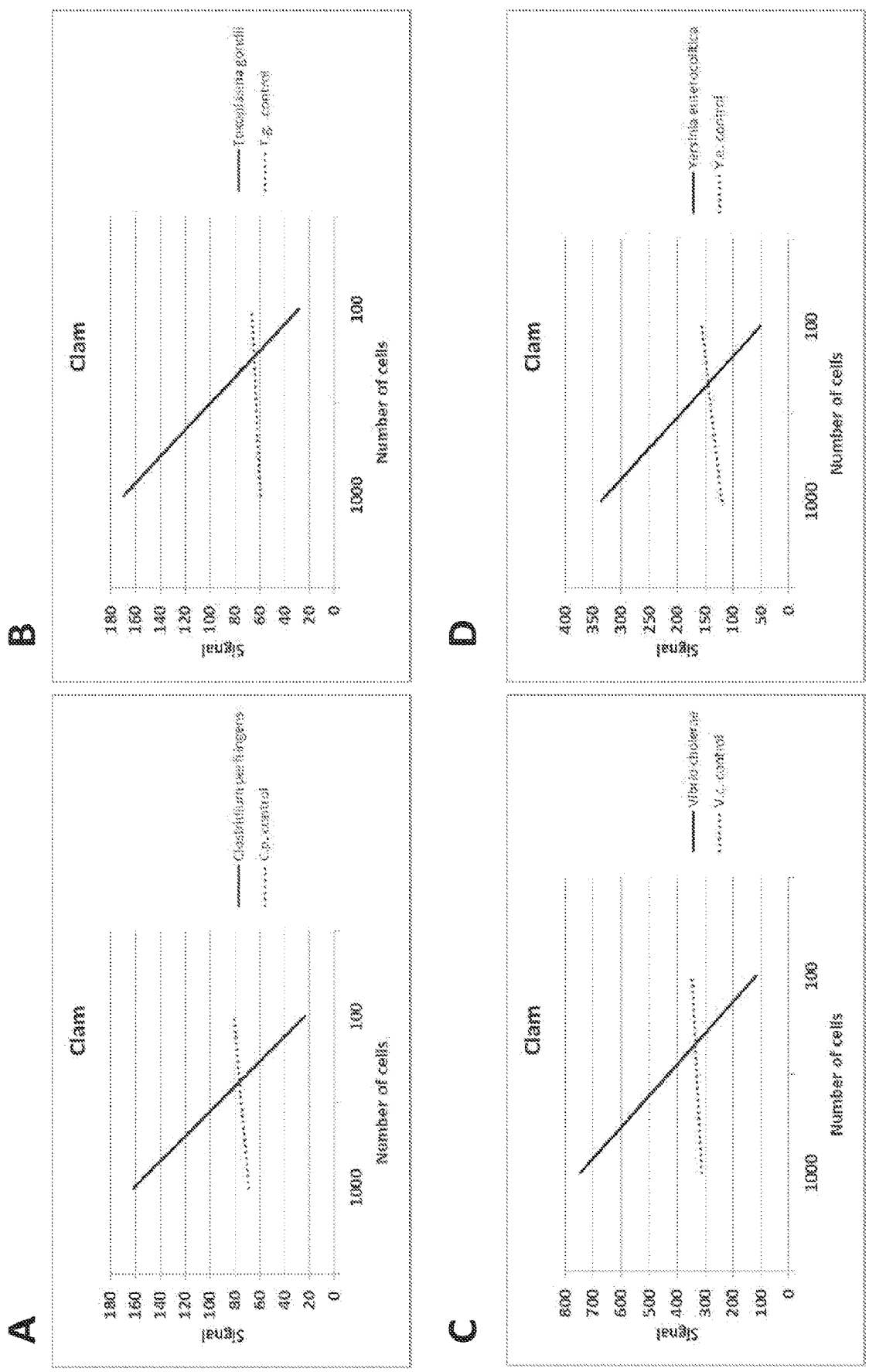
FIG. 10, comprising

PathoChip v3 was tested using mixtures of target organisms with human and lettuce cells. Aliquots of diluted bacterial pools were mixed with 100,000 human cells and 100 mg lettuce. Control samples contained human and lettuce cells only. The entire sample volume was used for nucleic acid extraction. All DNA and RNA recovered from each sample was amplified, labeled, and hybridized to PathoChip v3. Detection signal was computed as sum of selected probes for each test sample (solid line) and the control sample background (dotted line) (FIG. 7A). Detection signals were obtained for each of *Escherichia coli* O157:H7, *Legionella pneumophila, Listeria monocyto-*

TABLE 1

Probes to Human Sequences

| Experiment | PathoChip | Test (Cy3) | Xhh cross-hyb control (Cy5) | Amplification | Human probes, median Cy3 | Human probes, median Cy5 | Non-human probes, median Cy3 | Non-human probes, median Cy5 |
|---|---|---|---|---|---|---|---|---|
| 1 | v2a | Human gDNA, no Cot-1 | Human gDNA, no Cot-1 | none | 794 | 785 | 18 | 17 |
| 1 | v2b | Human gDNA, no Cot-1 | Human gDNA, no Cot-1 | none | 726 | 741 | 119 | 124 |
| 1 | v2a | Human gDNA + Cot-1 | Human gDNA + Cot-1 | none | 758 | 794 | 17 | 17 |
| 1 | v2b | Human gDNA + Cot-1 | Human gDNA + Cot-1 | none | 758 | 791 | 121 | 128 |

Example 3

Identification of Best Performing Probes for Targeted Species

Target organisms, including *Legionella pneumophila, Yersinia enterocolitica, Escherichia coli, Vibrio cholerae, Clostridium perfringens, Salmonella enterica, Shigella*

*genes, Salmonella enterica, Shigella flexneri, Vibrio cholerae*, and *Yersinia enterocolitica* cells mixed with human and lettuce cells (FIGS. 7B-7H. A small number of pathogen cells in a background of a large number of host cells can be detected, but with less absolute signal compared to pure pathogen cultures (see, FIGS. 6B-6H). The difference between test signal and host-only control signal indicates detection ability. These results indicate that the PathoChip is able to detect the presence of various target organisms with high sensitivity in the presence of background RNA and DNA.

Example 5

Assay Testing in the Presence of Food Background DNA+RNA

PathoChip v3 was tested using mixtures of target organisms and various foods. Target organisms, including *Toxoplasma gondii, Vibrio cholerae, Yersinia enterocolitica, Escherichia coli* O157:H7, *Legionella pneumophila, Salmonella enterica, Shigella flexneri*. Aliquots of diluted pathogen pool (1000 or 100 cells per species) mixed with milk (FIGS. 8A-8H), tomato (FIGS. 9A-9H), or clam (FIGS. 10A-10D). Control samples contained food only. The entire sample volume was used for nucleic acid extraction. All DNA and RNA recovered from each sample was amplified, labeled, and hybridized to PathoChip v3. Detection signal was computed as sum of selected probes for each test sample and the control sample background. These results indicate that the PathoChip is able to detect the presence of various target organisms with high sensitivity in food.

Example 6

Detection and Identification of an Unknown Infectious Agent in a Patient Sample

An important factor in the clinical management of infectious diseases lies in the establishment of the identity of the etiologic agent or pathogen responsible for the infection. A rapid and accurate diagnosis informs treatment selection and has a direct impact on patient outcome. The PathoChip and the extraction protocol used with it provide a way to detect and analyze pathogens from any type of sample, thus overcoming challenges that limit current procedures for pathogen detection.

Analysis of a patient sample using the PathoChip was able to detect a fungal agent that a hospital pathology lab was not able to identify. The patient was extremely ill when admitted to the hospital and presented symptoms of an infection. A brain sample from the patient was analyzed by querying the PathoChip with total nucleic acid isolated from the sample obtained.

Figure 11:
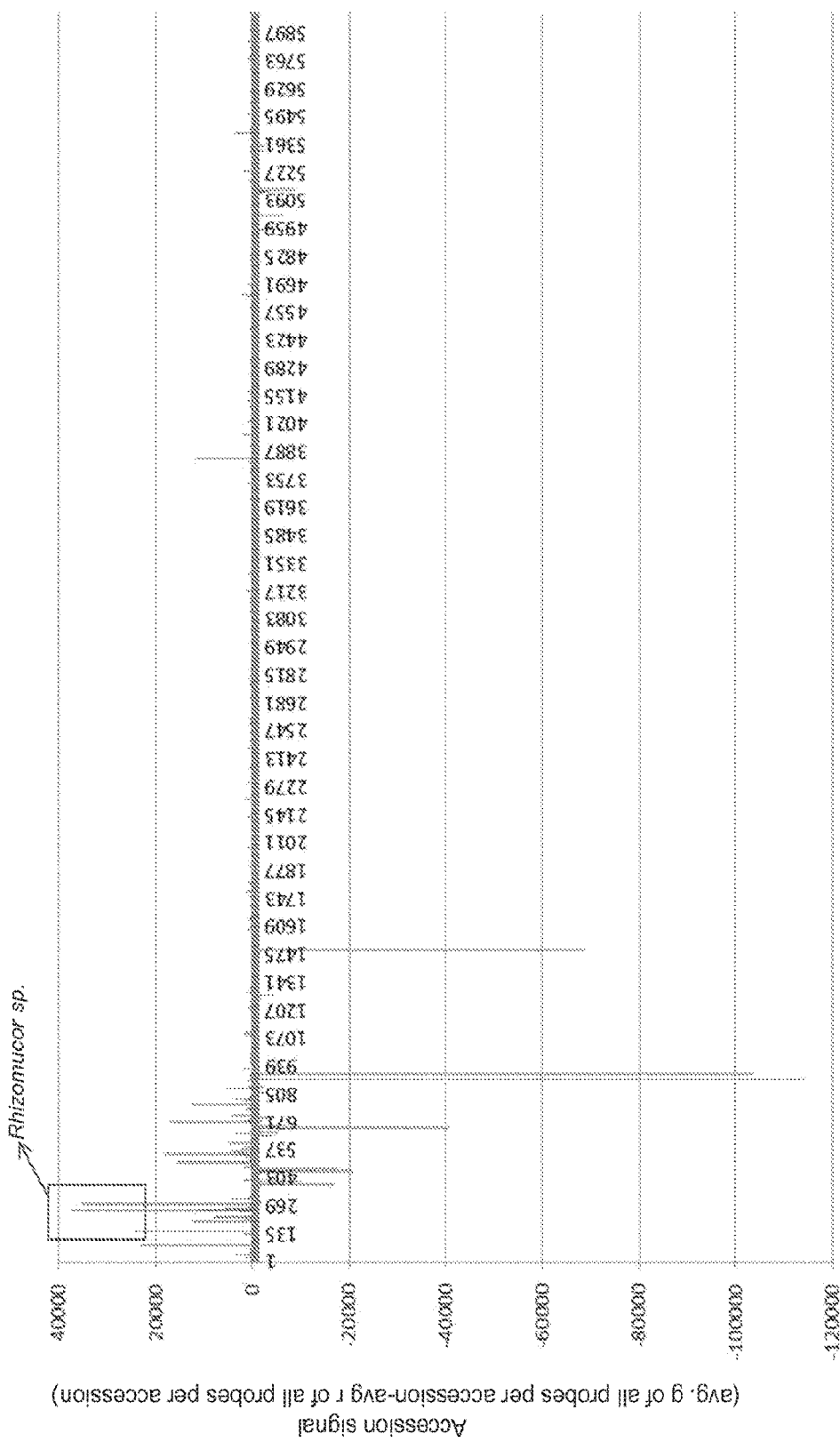
FIG. 11 is a graph depicting the accessional analysis of 60,000 probes of the PathoChip on a patient sample. Accessional analysis identified strong signal associated with fungi of the *Rhizomucor* genus in the patient sample compared to control. Accession signal is defined as average green (g) of all probes per accession-average red (r) of all probes per accession.
Figure 13:
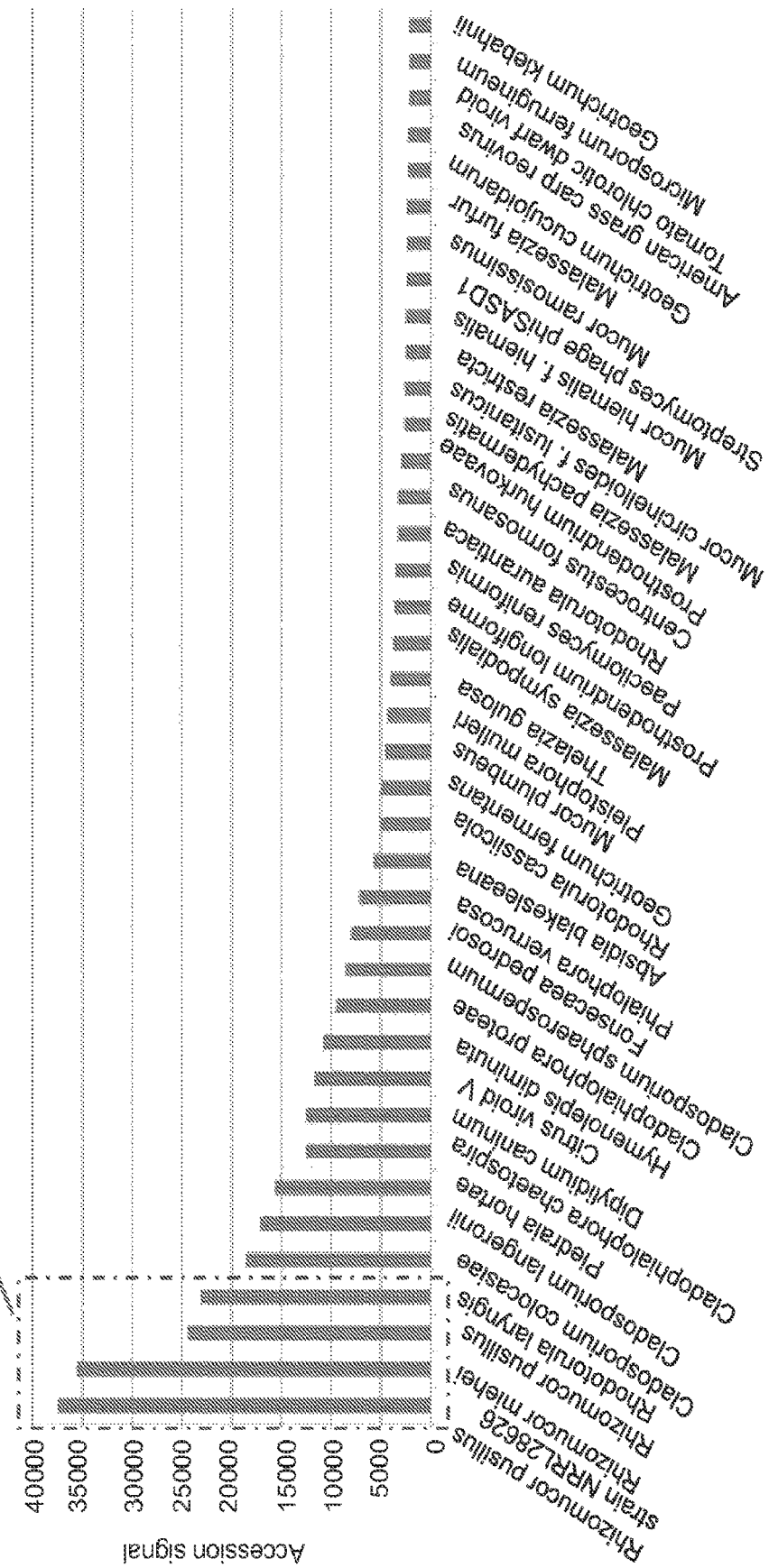
FIG. 13 is a graph showing that *Rhizomucor pusillus* strain NRRL28626 and *Rhizomucor miehel* had the most prominent signals from the screen. The top 4 pathogens in the patient sample, providing high accession signals, were fungal, including *Rhizomucor pusillus* strain NRRL28626, *Rhizomucor miehel*, *Rhizomucor pusillus*, and *Rhodotorula laryngis*.

Accessional analysis of 60,000 probes of PathoChip identified strong signal associated with fungi of the *Rhizomucor* genus (FIG. 11). Heat map data showing hybridization signal of all the probes of the accessions selected by Accession Analysis were generated (FIG. 12A). Probes that were either undetected or were also present in the control were disregarded (FIG. 13B), leaving a number of probes indicating fungal hybridization signals (FIG. 12B). Indeed, the top 2 pathogens providing high accession signals were *Rhizomucor pusillus* strain NRRL28626 and *Rhizomucor miehel* (FIG. 13). The other pathogens having high accession signals were *Rhizomucor pusillus* and *Rhodotorula laryngis*, although the accession signals were substantially lower compared to the top 2 pathogens. As both *Rhizomucor pusillus* strain NRRL28626 and *Rhizomucor miehel* had the most prominent signals from the screen, these 2 agents were identified as the pathogens. Interestingly, two different species of this fungus were able to be identified and distinguished using the PathoChip, demonstrating the power of the technology. Thus, the PathoChip was shown to be useful as a clinical assay by identifying 2 related fungi associated with this type of infection. Based on this diagnosis, an antifungal treatment regimen could be selected for the patient.

Identification of the infectious agent was achieved in about 36 hours with conservative estimates in hybridization to prevent signal loss. It is expected that an optimized protocol can substantially reduce the time to detection within 24 hours and no longer than 48 hours. This demonstration clearly shows the ability of the PathoChip to identify an unknown agent in a patient sample which was not even possible in a clinical pathology lab of a major metropolitan hospital.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents, publications, and accession numbers mentioned in this specification are herein incorporated by reference to the same extent as if each independent patent, publication, and accession number was specifically and individually indicated to be incorporated by reference.

What is claimed is:

1. A method of detecting one or more target nucleic acid molecules in a sample, comprising the use of a set of probes, the set of probes made by a method comprising:
   generating a metagenome in silico by compiling individual genomes, genes and partial sequences present in the sample into a local database and masking low complexity sequences, wherein the metagenome comprises a plurality of nucleic acid sequences;
   comparing each sequence in the metagenome against all others; and
   selecting nucleic acid probes that specifically target a unique nucleic acid sequence in the metagenome,
   wherein each unique target nucleic acid sequence is a 250-300 bp region with no more than 50 contiguous nucleotides having 70% or greater sequence homology to any other sequence in the metagenome or to the human genome;
   wherein the set of probes comprises at least 60,000 probes specific for pathogens selected from the group consisting of viral, bacterial, fungal, helminth, and protozoan pathogens;
   the method comprising hybridizing one or more sample nucleic acid molecules to the set of probes, wherein the sample nucleic acid molecules are labeled with a detectable moiety; and
   detecting a signal from the hybridizing of the nucleic acid probe with the sample nucleic acid molecule labeled with the detectable moiety, as compared to a reference.

2. The method of claim 1, wherein the sample nucleic acid molecules are selected from the group consisting of DNA and RNA.

3. The method of claim 1, wherein the sample nucleic acid molecules are from a plurality of organisms or pathogens.

4. The method of claim 3, wherein the plurality of pathogens comprise two or more pathogens selected from the group consisting of viral, bacterial, fungal, helminth, and protozoan pathogens.

5. The method of claim 4, comprising about 40, 50, 60, 70, 80, 90, 100, 200, 300, 400, 500, 600, 700, 800, 900, 1000, 2000, 3000 or more pathogens.

6. A method of detecting one or more target nucleic acid molecules in a sample, comprising the use of a set of probes, the set of probes made by a method comprising:

generating a metagenome in silico by compiling individual genomes, genes and partial sequences present in the sample into a local database, and concatenating the individual genomes, genes and partial sequences into a single metagenome, wherein the metagenome comprises a plurality of nucleic acid sequences;

comparing each sequence in the metagenome against all others; and selecting nucleic acid probes that specifically target a unique nucleic acid sequence in the metagenome, wherein each unique target nucleic acid sequence is a 250-300 bp region with no more than 50 contiguous nucleotides having 70% or greater sequence homology to any other sequence in the metagenome or to the human genome;

wherein the set of probes comprises at least 60,000 probes specific for pathogens selected from the group consisting of viral, bacterial, fungal, helminth, and protozoan pathogens;

the method comprising hybridizing one or more sample nucleic acid molecules to the set of probes, wherein the sample nucleic acid molecules are labeled with a detectable moiety; and detecting a signal from the hybridizing of the nucleic acid probe with the sample nucleic acid molecule labeled with the detectable moiety, as compared to a reference.

* * * * *